US012780799B2

(12) United States Patent
Yang et al.

(10) Patent No.: US 12,780,799 B2
(45) Date of Patent: Nov. 3, 2026

(54) SULFUR-CONTAINING ISOINDOLINE DERIVATIVE, AND PREPARATION METHOD THEREFOR AND MEDICAL USE THEREOF

(71) Applicants: JIANGSU HENGRUI PHARMACEUTICALS CO., LTD., Lianyungang (CN); SHANGHAI HENGRUI PHARMACEUTICAL CO., LTD., Shanghai (CN)

(72) Inventors: Fanglong Yang, Shanghai (CN); Minqiang Jia, Shanghai (CN); Gang Chen, Shanghai (CN); Peihua Guo, Shanghai (CN); Limin Zhang, Shanghai (CN); Feng He, Shanghai (CN); Weikang Tao, Shanghai (CN)

(73) Assignees: JIANGSU HENGRUI PHARMACEUTICALS CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 747 days.

(21) Appl. No.: 18/017,388

(22) PCT Filed: Jul. 20, 2021

(86) PCT No.: PCT/CN2021/107297

§ 371 (c)(1),
(2) Date: Jan. 20, 2023

(87) PCT Pub. No.: WO2022/017365

PCT Pub. Date: Jan. 27, 2022

(65) Prior Publication Data

US 2023/0257366 A1 Aug. 17, 2023

(30) Foreign Application Priority Data

Jul. 20, 2020 (CN) ........................ 202010696995.5
Aug. 6, 2020 (CN) ........................ 202010783483.2
Nov. 5, 2020 (CN) ........................ 202011223930.5
Apr. 16, 2021 (CN) ........................ 202110410441.9

(51) Int. Cl.
*C07D 401/14* (2006.01)
*A61P 35/00* (2006.01)

(52) U.S. Cl.
CPC ............ *C07D 401/14* (2013.01); *A61P 35/00* (2018.01)

(58) Field of Classification Search
CPC ............................... C07D 401/14; A61P 35/00
See application file for complete search history.

(56) References Cited

U.S. PATENT DOCUMENTS

2011/0196150 A1* 8/2011 Man ........................ A61P 17/00 544/131
2019/0361005 A1 11/2019 Anton et al.
2020/0216418 A1* 7/2020 Artman, III ......... C07D 401/14
2023/0270742 A1* 8/2023 Agrawal ............. A61K 9/4858 514/253.09

FOREIGN PATENT DOCUMENTS

CN 101679380 A 3/2010
CN 102822165 A 12/2012
CN 109415336 A 3/2019
WO 2008/115516 A2 9/2008
WO 2011/100380 A1 8/2011
WO 2019/014100 A1 1/2019
WO 2019/226770 A1 11/2019
WO 2020/064002 A1 4/2020
WO 2021/055756 A1 3/2021

OTHER PUBLICATIONS

Thornber, Chemical Society Reviews, 4, 1979 (Year: 1979).*
Gaikwad, American Journal of PharmTech Research, 2012, 2, 4 (Year: 2012).*
Hansen, Journal of Medicinal Chemistry, 2020, 63, 6648-6676, Published: Mar. 4, 2020 (Year: 2020).*

* cited by examiner

*Primary Examiner* — Andrew D Kosar
*Assistant Examiner* — Phillip Matthew Rzeczycki
(74) *Attorney, Agent, or Firm* — Morgan, Lewis & Bockius LLP

(57) ABSTRACT

The present application relates to a sulfur-containing isoindoline derivative, and a preparation method therefor and medical use thereof. In particular, the present disclosure relates to a sulfur-containing isoindoline derivative as represented by general formula (I), a preparation method therefor, a pharmaceutical composition containing the derivative, and use thereof as a therapeutic agent, particularly use thereof as a Cereblon modulator in the field of treatment of multiple myeloma.

(I)

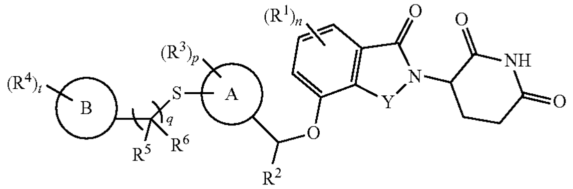

4 Claims, 1 Drawing Sheet

SULFUR-CONTAINING ISOINDOLINE DERIVATIVE, AND PREPARATION METHOD THEREFOR AND MEDICAL USE THEREOF

CROSS-REFERENCE TO RELATED APPLICATIONS

The present application is a national stage application of International Patent Application No. PCT/CN2021/107297, filed Jul. 20, 2021, which claims the benefit of and priority to Chinese Patent application Ser. No. 202010696995.5 filed on Jul. 20, 2020, Chinese Patent Application No. 202010783483.2 filed on Aug. 6, 2020, Chinese Patent Application No. 202011223930.5 filed on Nov. 5, 2020, and Chinese Patent Application No. 202110410441.9 filed on Apr. 16, 2021, each of which is incorporated herein by reference in their entirety.

TECHNICAL FIELD

The present disclosure belongs to the field of pharmaceutics, and relates to a sulfur-containing isoindoline derivative, a preparation method therefor and pharmaceutical use thereof. In particular, the present disclosure relates to a sulfur-containing isoindoline derivative of general formula (I), a preparation method therefor, a pharmaceutical composition comprising the derivative, and use of the derivative as a Cereblon modulator in the field of treatment of multiple myeloma.

BACKGROUND

Multiple myeloma (MM) is a malignant tumor, the main symptoms of which include hypercalcemia, renal injury, anemia, and bone disease. MM is the second most common hematological malignancy following non-Hodgkin's lymphoma, with an annual incidence of 4-6 per 100,000 people worldwide and 1.6 per 100,000 people in China. The current treatment methods are mainly drug therapy and autologous stem cell transplantation.

At present, there are four main classes of drugs widely used in clinical practice, which are alidomide immunomodulator, proteasome inhibitors, hormones and monoclonal antibodies. The drugs in clinical research stage include diabody, ADC, CAR-T, etc. Those drugs have different mechanisms of action, and they can often achieve better efficacy when used in combination. In clinical practice, dual, triple or even quadruple therapy is generally adopted, usually a combination therapy of an immunomodulator, a proteasome inhibitor and a hormone, sometimes with an additional antibody. Lenalidomide is the most commonly used immunomodulator, and is used in first-line therapy, maintenance therapy after stem cell transplantation, and second-line and third-line therapies after relapse. The drug reached $9.7 billion in sales in 2018/2019. In addition, the overall MINI market is considerable and growing rapidly due to longer patient survival, and correspondingly longer duration of medication after continuous improvements and refinements in the diagnosis and treatment of MM. The MINI market is expected to reach a scale of $33 billion in 2022, with the largest proportion still being immunomodulators such as lenalidomide.

The mechanism of action of immunomodulators (IMiD) for treating MINI is mainly that IMiD drugs can activate the E3 ligase activity of CRBN after binding to Cereblon (CRBN) protein to selectively bind to transcription factors Ikaros (IKZF1) and Aiolos (IKZF3), thereby resulting in rapid ubiquitination and degradation of Ikaros and Aiolos. Downregulation of Ikaros/Aiolos results in downregulation of c-Myc, followed by the downregulation of IRF4, ultimately resulting in inhibition of growth and apoptosis of myeloma cells. In addition, IKZF3 can also inhibit the transcription of cytokines IL2 and TNF in T/NK cells. After the degradation of IKZF3, this inhibition can be relieved, and the release of these cytokines is promoted, so that an immunomodulatory effect is achieved. Clinical trials have also shown that the clinical benefit of IMiD drugs correlates with the expression level of CRBN. It was found that the inhibitory activity of lenalidomide for cell growth was lost and drug resistance was developed after CRBN was knocked down in lenalidomide-sensitive cell lines (OPM2 and KMS18), which indicates that the level of CRBN knockdown correlates with the degree of drug resistance. In a cell proliferation experiment, after the expression level of CRBN in cells (U266-CRBN60 and U266-CRBN75) was reduced, the inhibitory activity of both lenalidomide and pomalidomide for cell growth is reduced.

Currently, the IMiD drugs that have been approved for marketing include thalidomide, lenalidomide and pomalidomide, all from Celgene (now incorporated by BMS). For those three compounds, the binding forces to CRBN are increased sequentially, so the clinical doses are reduced sequentially. The primary indication for the three compounds is MINI, and there are other indications for thalidomide and lenalidomide (especially lenalidomide), such as myelodysplastic syndrome (MDS). In terms of side effects, lenalidomide and pomalidomide are similar in performance, with significant myelosuppressive effect caused by target-related toxicity; thalidomide has some other side effects such as sedation, constipation, and neurological side effects.

The adipimide moiety of all IMiDs binds to a hydrophobic pocket defined by the three tryptophan residues in CRBN (referred to as "thalidomide binding pocket"). In contrast, the phthalimide/isoindolone ring is exposed to the solvent and alters the molecular surface of CRBN, thereby modulating substrate recognition. Different IMiDs result in significant modification of the surface of CRBN molecules and different preferences for substrate recognition. Thus, modifications of IMiDs may lead to degradation of other transcription factors, causing unwanted toxic and side effects. This mode of action of IMiDs is also known as molecular glue, which vividly expresses the bonding effect of this small molecule on two protein substrates.

Since the median survival for multiple myeloma is now more than five years, the prolonged survival leads to a high proportion of resistance to currently available drugs such as lenalidomide and pomalidomide in most patients, which seriously reduces the therapeutic effect of such drugs. Therefore, it is contemplated to develop more active drug molecules to overcome the problem of drug resistance whilst minimizing the toxic and side effects of such compounds.

Disclosed patent applications for Cereblon regulators include WO2008115516A2, WO2011100380A1, WO2019226770A1, WO2019014100A1, WO2020064002A1, etc.

SUMMARY

The present disclosure is intended to provide a compound of general formula (I) or a tautomer, mesomer, racemate, enantiomer or diastereomer thereof or a mixture thereof, or a pharmaceutically acceptable salt thereof, (I)

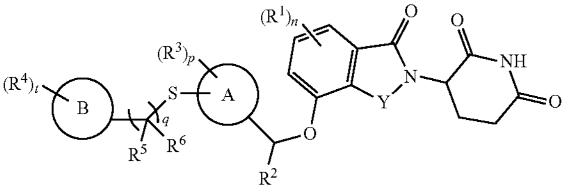

wherein:

ring A is aryl or heteroaryl;

ring B is cycloalkyl or heterocyclyl;

Y is $CH_2$ or C(O);

$R^1$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro and hydroxy;

$R^2$ is selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^3$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro and hydroxy;

$R^4$ is selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^5$ and $R^6$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

n is 0, 1, 2 or 3;

p is 0, 1, 2, 3 or 4;

q is 0, 1 or 2; and t is 0, 1, 2 or 3.

In some preferred embodiments of the present disclosure, provided is the compound of general formula (I) or the tautomer, mesomer, racemate, enantiomer or diastereomer thereof or the mixture thereof, or the pharmaceutically acceptable salt thereof, which is a compound of general formula (I-1) or a tautomer, mesomer, racemate, enantiomer or diastereomer thereof or a mixture thereof, or a pharmaceutically acceptable salt thereof:

(I-1)

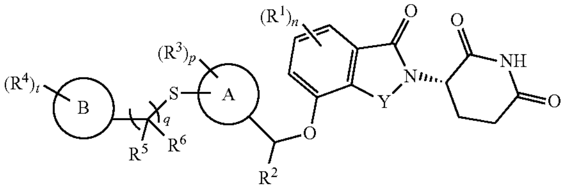

wherein:

ring A, ring B, Y, $R^1$ to $R^6$, n, p, q and t are as defined in general formula (I).

In some preferred embodiments of the present disclosure, provided is the compound of general formula (I) or the tautomer, mesomer, racemate, enantiomer or diastereomer thereof or the mixture thereof, or the pharmaceutically acceptable salt thereof, which is a compound of general formula (I-2) or a tautomer, mesomer, racemate, enantiomer or diastereomer thereof or a mixture thereof, or a pharmaceutically acceptable salt thereof:

(I-2)

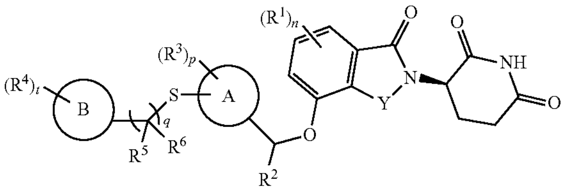

wherein:

ring A, ring B, Y, $R^1$ to $R^6$, n, p, q and t are as defined in general formula (I).

In some preferred embodiments of the present disclosure, provided is the compound of general formula (I) or the tautomer, mesomer, racemate, enantiomer or diastereomer thereof or the mixture thereof, or the pharmaceutically acceptable salt thereof, which is a compound of general formula (II) or a tautomer, mesomer, racemate, enantiomer or diastereomer thereof or a mixture thereof, or a pharmaceutically acceptable salt thereof:

(II)

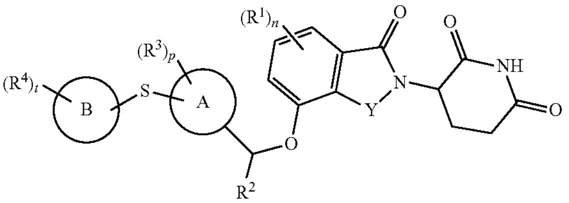

wherein:

ring A, ring B, Y, $R^1$ to $R^4$, n, p and t are as defined in general formula (I).

In some preferred embodiments of the present disclosure, provided is the compound of general formula (I) or (II) or the tautomer, mesomer, racemate, enantiomer or diastereomer thereof or the mixture thereof, or the pharmaceutically acceptable salt thereof, which is a compound of general formula (II-1) or (II-2) or a tautomer, mesomer, racemate, enantiomer or diastereomer thereof or a mixture thereof, or a pharmaceutically acceptable salt thereof:

(II-1)

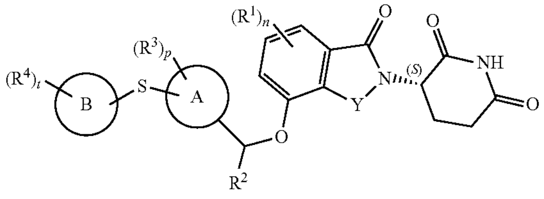

or (II-2)

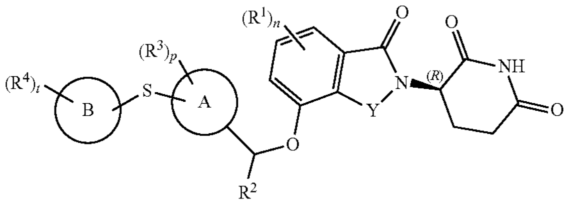

wherein:

ring A, ring B, Y, $R^1$ to $R^4$, n, p and t are as defined in general formula (II).

In some embodiments of the present disclosure, provided is the compound of general formula (I), general formula (I-1), general formula (I-2), general formula (II), general formula (II-1) or general formula (II-2) or the tautomer, mesomer, racemate, enantiomer or diastereomer thereof or the mixture thereof, or the pharmaceutically acceptable salt thereof, wherein ring A is phenyl or 5- to 6-membered heteroaryl; preferably selected from the group consisting of phenyl, pyridinyl and pyrimidinyl.

In some embodiments of the present disclosure, provided is the compound of general formula (I), general formula (I-1), general formula (I-2), general formula (II), general formula (II-1) or general formula (II-2) or the tautomer, mesomer, racemate, enantiomer or diastereomer thereof or the mixture thereof, or the pharmaceutically acceptable salt thereof, wherein

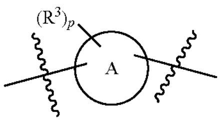

is selected from the group consisting of

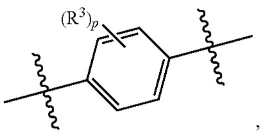

,

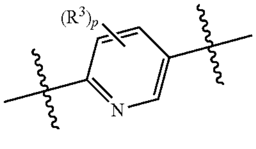

and

-continued

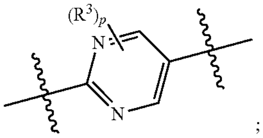

;

and $R^3$ and p are as defined in general formula (I).

In some embodiments of the present disclosure, provided is the compound of general formula (I), general formula (I-1), general formula (I-2), general formula (II), general formula (II-1) or general formula (II-2) or the tautomer, mesomer, racemate, enantiomer or diastereomer thereof or the mixture thereof, or the pharmaceutically acceptable salt thereof, wherein ring B is 3- to 8-membered heterocyclyl; preferably, ring B is selected from the group consisting of piperidinyl, pyrrolidinyl and azetidinyl; more preferably, ring B is 6-membered heterocyclyl; and most preferably, ring B is piperidinyl.

In some embodiments of the present disclosure, provided is the compound of general formula (I), general formula (I-1), general formula (I-2), general formula (II), general formula (II-1) or general formula (II-2) or the tautomer, mesomer, racemate, enantiomer, or diastereomer thereof or the mixture thereof, or the pharmaceutically acceptable salt thereof, wherein

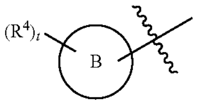

is

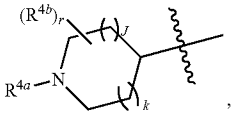

,

J is 0 or 1, and k is 0 or 1; preferably,

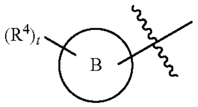

is

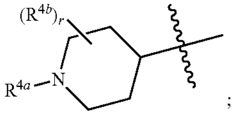

;

$R^{4a}$ and $R^{4b}$ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl; and r is 0, 1 or 2.

In some preferred embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, which is a compound of general formula (IIG) or a tautomer, mesomer, racemate, enantiomer or diastereomer thereof or a mixture thereof, or a pharmaceutically acceptable salt thereof:

(IIG)

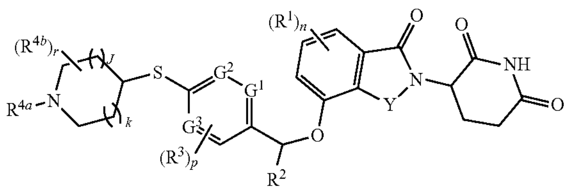

wherein:

$G^1$, $G^2$ and $G^3$ are identical or different and are each independently a carbon atom or a nitrogen atom;

$R^{4a}$ and $R^{4b}$ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

r is 0, 1 or 2;

J is 0 or 1;

k is 0 or 1; and

Y, $R^1$ to $R^3$, n and p are as defined in general formula (I).

In some preferred embodiments of the present disclosure, provided is the compound of general formula (I), general formula (I-1), general formula (II), general formula (II-1) or general formula (IIG) or the tautomer, mesomer, racemate, enantiomer or diastereomer thereof or the mixture thereof, or the pharmaceutically acceptable salt thereof, which is a compound of general formula (IIG-1) or a tautomer, mesomer, racemate, enantiomer or diastereomer thereof or a mixture thereof, or a pharmaceutically acceptable salt thereof:

(IIG-1)

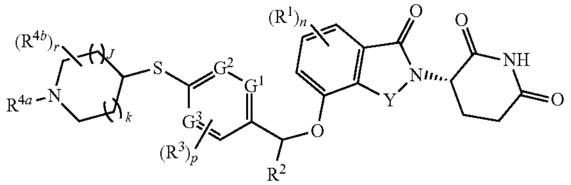

wherein:

$G^1$, $G^2$ and $G^3$ are identical or different and are each independently a carbon atom or a nitrogen atom;

$R^{4a}$ and $R^{4b}$ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

r is 0, 1 or 2;

J is 0 or 1;

k is 0 or 1; and

Y, $R^1$ to $R^3$, n and p are as defined in general formula (I).

In some preferred embodiments of the present disclosure, provided is the compound of general formula (I), general formula (I-2), general formula (II), general formula (II-2) or general formula (IIG) or the tautomer, mesomer, racemate, enantiomer or diastereomer thereof or the mixture thereof, or the pharmaceutically acceptable salt thereof, which is a compound of general formula (IIG-2) or a tautomer, mesomer, racemate, enantiomer or diastereomer thereof or a mixture thereof, or a pharmaceutically acceptable salt thereof:

(IIG-2)

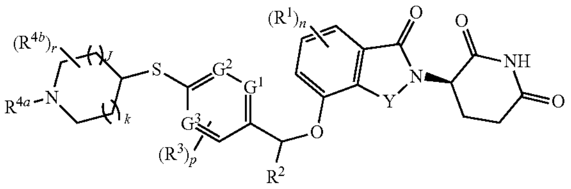

wherein:

$G^1$, $G^2$ and $G^3$ are identical or different and are each independently a carbon atom or a nitrogen atom;

$R^{4a}$ and $R^{4b}$ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

r is 0, 1 or 2;

J is 0 or 1;

k is 0 or 1; and

Y, $R^1$ to $R^3$, n and p are as defined in general formula (I).

In some preferred embodiments of the present disclosure, provided is the compound of general formula (IIG), general formula (IIG-1) or general formula (IIG-2) or the tautomer, mesomer, racemate, enantiomer or diastereomer thereof or the mixture thereof, or the pharmaceutically acceptable salt thereof, wherein $G^2$ is a nitrogen atom, and $G^1$ and $G^3$ are carbon atoms; or $G^1$ is a nitrogen atom, $G^2$ and $G^3$ are carbon atoms; or $G^1$, $G^2$ and $G^3$ are all carbon atoms; or $G^2$ and $G^3$ are both nitrogen atoms, and $G^1$ is a carbon atom.

In some preferred embodiments of the present disclosure, provided is the compound of general formula (I), general formula (II) or general formula (IIG) or the tautomer, mesomer, racemate, enantiomer or diastereomer thereof or the mixture thereof, or the pharmaceutically acceptable salt thereof, which is a compound of general formula (III) or a tautomer, mesomer, racemate, enantiomer or diastereomer thereof or a mixture thereof, or a pharmaceutically acceptable salt thereof:

(III)

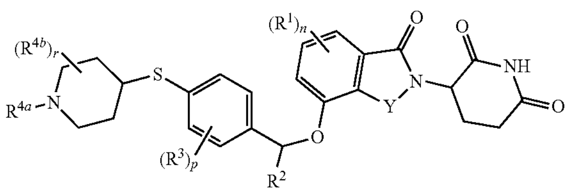

wherein:

$R^{4a}$ and $R^{4b}$ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

r is 0, 1 or 2;

Y, $R^1$ to $R^3$, n and p are as defined in general formula (I).

In some preferred embodiments of the present disclosure, provided is the compound of general formula (I), general formula (I-1), general formula (II), general formula (II-1), general formula (IIG), general formula (IIG-1) or general formula (III) or the tautomer, mesomer, racemate, enantiomer or diastereomer thereof or the mixture thereof, or the pharmaceutically acceptable salt thereof, which is a compound of general formula (III-1) or a tautomer, mesomer, racemate, enantiomer or diastereomer thereof or a mixture thereof, or a pharmaceutically acceptable salt thereof:

(III-1)

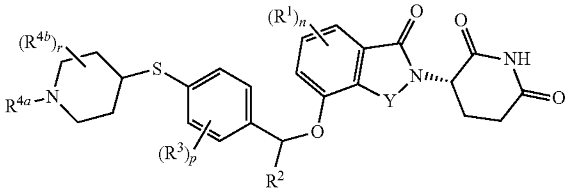

wherein:

Y, $R^1$ to $R^3$, $R^{4a}$, $R^{4b}$, r, n and p are as defined in general formula (III).

In some preferred embodiments of the present disclosure, provided is the compound of general formula (I), general formula (I-2), general formula (II), general formula (II-2), general formula (IIG), general formula (IIG-2) or general formula (III) or the tautomer, mesomer, racemate, enantiomer or diastereomer thereof or the mixture thereof, or the pharmaceutically acceptable salt thereof, which is a compound of general formula (III-2) or a tautomer, mesomer, racemate, enantiomer or diastereomer thereof or a mixture thereof, or a pharmaceutically acceptable salt thereof:

(III-2)

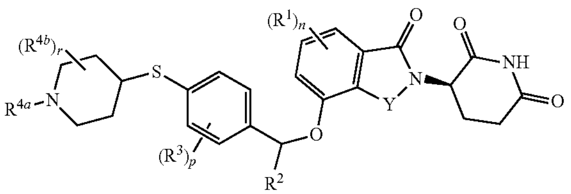

wherein:

Y, $R^1$ to $R^3$, $R^{4a}$, $R^{4b}$, r, n and p are as defined in general formula (III).

In some preferred embodiments of the present disclosure, provided is the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or formula (III-2) or the tautomer, mesomer, racemate, enantiomer or diastereomer thereof or the mixture thereof, or the pharmaceutically acceptable salt thereof, wherein Y is $CH_2$.

In some preferred embodiments of the present disclosure, provided is the compound of general formula (I), general formula (I-1), general formula (I-2), general formula (II), general formula (II-1) or formula (II-2) or the tautomer, mesomer, racemate, enantiomer or diastereomer thereof or the mixture thereof, or the pharmaceutically acceptable salt thereof, wherein $R^4$ are identical or different and are each independently selected from the group consisting of a hydrogen atom, halogen, $C_{1-6}$ alkyl, 3- to 8-membered cycloalkyl, 3- to 8-membered heterocyclyl, 6- to 10-membered aryl, and 5- to 10-membered heteroaryl, wherein the 3- to 8-membered cycloalkyl, 3- to 8-membered heterocyclyl, 6- to 10-membered aryl, and 5- to 10-membered heteroaryl are each independently and optionally substituted with one or more substituents selected from the group consisting of halogen, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano, amino, nitro, hydroxy and $C_{1-6}$ hydroxyalkyl.

In some preferred embodiments of the present disclosure, provided is the compound of general formula (IIG), general formula (IIG-1), general formula (IIG-2), general formula (III), general formula (III-1) or general formula (III-2) or the tautomer, mesomer, racemate, enantiomer or diastereomer thereof or the mixture thereof, or the pharmaceutically acceptable salt thereof, wherein $R^{4a}$ is selected from the group consisting of 3- to 8-membered cycloalkyl, 3- to 8-membered heterocyclyl, 6- to 10-membered aryl, and 5- to 10-membered heteroaryl, wherein the 3- to 8-membered cycloalkyl, 3- to 8-membered heterocyclyl, 6- to 10-membered aryl, and 5- to 10-membered heteroaryl are each independently and optionally substituted with one or more substituents selected from the group consisting of halogen, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano, amino, nitro, hydroxy, and $C_{1-6}$ hydroxyalkyl; and $R^{4b}$ are identical or different and are each independently selected from the group consisting of a hydrogen atom, halogen, $C_{1-6}$ alkyl and 3- to 8-membered cycloalkyl; preferably, $R^{4a}$ is

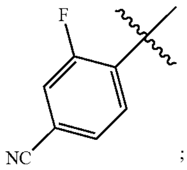 [SMILES: *c1ccc(C#N)cc1F]

;

and $R^{4b}$ is a hydrogen atom.

In some preferred embodiments of the present disclosure, provided is the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or the tautomer, mesomer, racemate, enantiomer or diastereomer thereof or the mixture thereof, or the pharmaceutically acceptable salt thereof, wherein $R^1$ are identical or different and are each independently selected from the group consisting of a hydrogen atom, halogen, and $C_{1-6}$ alkyl; preferably, $R^1$ is a hydrogen atom.

In some embodiments of the present disclosure, provided is the compound of general formula (I), general formula (I-1), general formula (I-2), general formula (II), general formula (II-1), general formula (II-2), general formula (IIG), general formula (IIG-1), formula (IIG-2), general formula (III), general formula (III-1) or general formula (III-2) or the tautomer, mesomer, racemate, enantiomer or diastereomer thereof or the mixture thereof, or the pharmaceutically acceptable salt thereof, wherein $R^2$ is selected from the group consisting of a hydrogen atom, $C_{1-6}$ alkyl, and 3- to 8-membered cycloalkyl; preferably, $R^2$ is a hydrogen atom.

In some embodiments of the present disclosure, provided is the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or the tautomer, mesomer, racemate, enantiomer or diastereomer thereof or the mixture thereof, or the pharmaceutically acceptable salt thereof, wherein $R^3$ are identical or different and are each independently selected from the group consisting of a hydrogen atom, halogen, and $C_{1-6}$ alkyl.

In some embodiments of the present disclosure, provided is the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or the tautomer, mesomer, racemate, enantiomer or diastereomer thereof or the mixture thereof, or the pharmaceutically acceptable salt thereof, wherein $R^3$ are identical or different and are each independently selected from the group consisting of a hydrogen atom and halogen; preferably a hydrogen atom.

In some embodiments of the present disclosure, provided is the compound of general formula (I), general formula (I-1) or general formula (I-2) or the tautomer, mesomer, racemate, enantiomer or diastereomer thereof or the mixture thereof, or the pharmaceutically acceptable salt thereof, wherein q is 0 or 1; preferably, q is 0.

In some embodiments of the present disclosure, provided is the compound of general formula (I), general formula (I-1), general formula (I-2), general formula (II), genera formula (II-1), general formula (II-2), general formula (IIG), general formula (IIG-1), general formula (IIG-2), general formula (III), general formula (III-1) or general formula (III-2) or the tautomer, mesomer, racemate, enantiomer or diastereomer thereof or the mixture thereof, or the pharmaceutically acceptable salt thereof, wherein n is 0 or 1.

In some embodiments of the present disclosure, provided is the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or formula (III-2) or the tautomer, mesomer, racemate, enantiomer or diastereomer thereof or the mixture thereof, or the pharmaceutically acceptable salt thereof, wherein p is 0, 1 or 2.

In some embodiments of the present disclosure, provided is the compound of general formula (I), general formula (I-1), general formula (I-2), general formula (II), general formula (II-1) or general formula (II-2) or the tautomer, mesomer, racemate, enantiomer or diastereomer thereof or the mixture thereof, or the pharmaceutically acceptable salt thereof, wherein t is 0, 1 or 2.

In some embodiments of the present disclosure, provided is the compound of general formula (IIG), general formula (IIG-1), general formula (IIG-2), general formula (III), general formula (III-1) or general formula (III-2) or the tautomer, mesomer, racemate, enantiomer or diastereomer thereof or the mixture thereof, or the pharmaceutically acceptable salt thereof, wherein r is 0 or 1.

In some embodiments of the present disclosure, provided is the compound of general formula (III), general formula (III-1) or general formula (III-2) or the tautomer, mesomer, racemate, enantiomer or diastereomer thereof or the mixture thereof, or the pharmaceutically acceptable salt thereof, wherein: Y is $CH_2$; $R^1$ are identical or different and are each independently selected from the group consisting of a hydrogen atom, halogen and $C_{1-6}$ alkyl; $R^2$ is a hydrogen atom; $R^3$ are identical or different and are each independently a hydrogen atom or halogen; $R^{4a}$ is

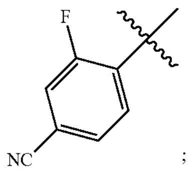 [SMILES: *c1ccc(C#N)cc1F]

;

$R^{4b}$ is a hydrogen atom; n is 0 or 1; p is 0 or 1; and r is 1.

TABLE A
| Typical compounds of the present disclosure include, but are not limited to: | |
|---|---|
| Example No. | Structure and name of compound |
| 1 | 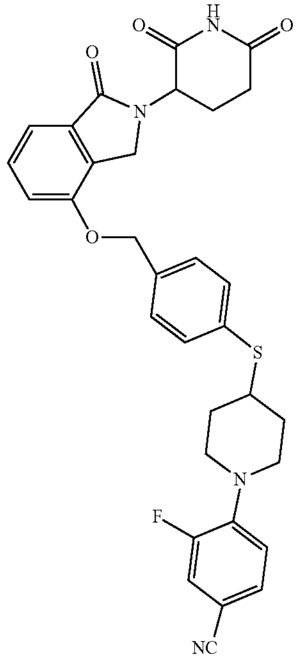 1 4-(4-((4-(((2-(2,6-dioxopiperidin-3-yl)-1-oxoisoindolin-4-yl)oxy)methyl) phenyl)thio)piperidin-1-yl)-3-fluorobenzonitrile 1 |
| 2 | 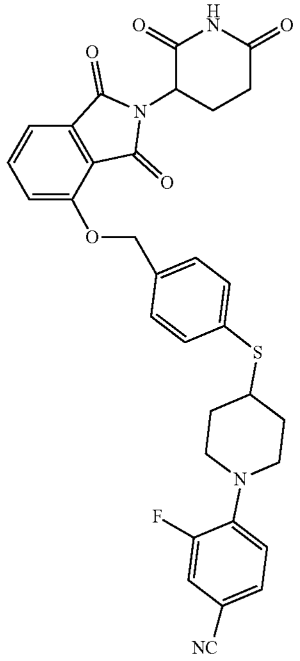 2 4-(4-((4-(((2-(2,6-dioxopiperidin-3-yl)-1,3-dioxoisoindolin-4-yl)oxy) methyl)phenyl)thio)piperidin-1-yl)-3-fluorobenzonitrile 2 |

TABLE A-continued
| Example No. | Structure and name of compound |
|---|---|
| | Typical compounds of the present disclosure include, but are not limited to: |
| 2-1 | 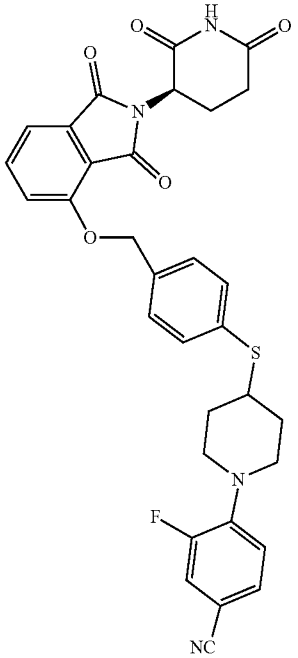 2-1 (R)-4-(4-((4-(((2-(2,6-dioxopiperidin-3-yl)-1,3-dioxoisoindolin-4-yl) oxy)methyl)phenyl)thio)piperidin-1-yl)-3-fluorobenzonitrile 2-1 |
| 2-2 | 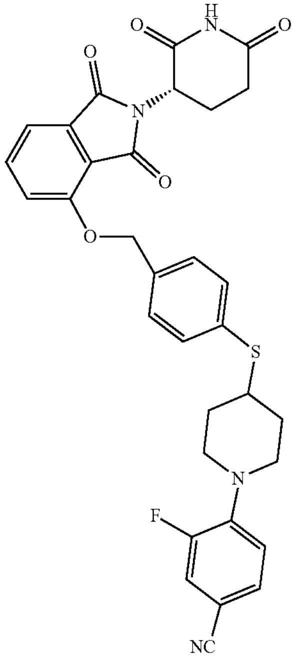 2-2 (S)-4-(4-((4-(((2-(2,6-dioxopiperidin-3-yl)-1,3-dioxoisoindolin-4-yl) oxy)methyl)phenyl)thio)piperidin-1-yl)-3-fluorobenzonitrile 2-2 |

TABLE A-continued
| Typical compounds of the present disclosure include, but are not limited to: | |
|---|---|
| Example No. | Structure and name of compound |
| 3 | 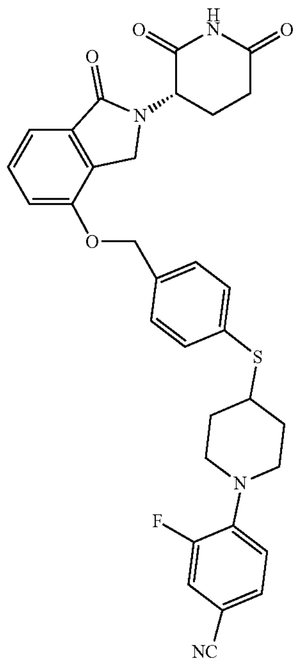 3 (S)-4-(4-((4-(((2-(2,6-dioxopiperidin-3-yl)-1-oxoisoindolin-4-yl)oxy) methyl)phenyl)thio)piperidin-1-yl)-3-fluorobenzonitrile 3 |
| 3' | 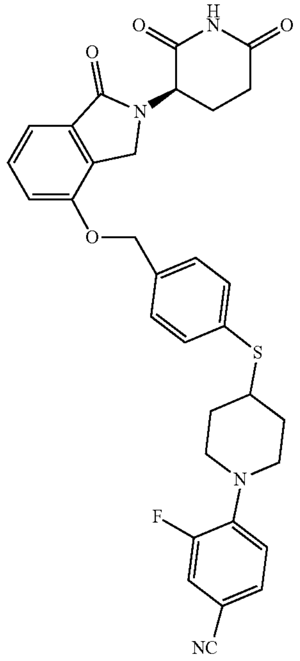 3' (R)-4-(4-((4-(((2-(2,6-dioxopiperidin-3-yl)-1-oxoisoindolin-4-yl)oxy) methyl)phenyl)thio)piperidin-1-yl)-3-fluorobenzonitrile 3' |

TABLE A-continued
| Typical compounds of the present disclosure include, but are not limited to: | |
|---|---|
| Example No. | Structure and name of compound |
| 4 | 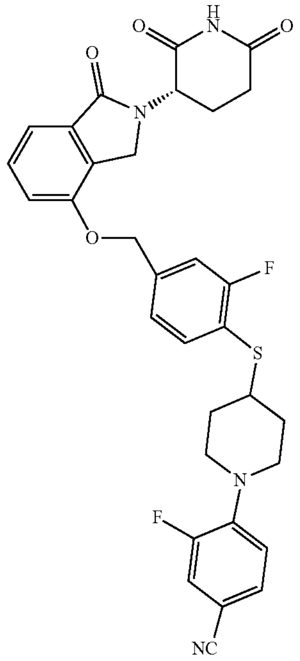 4 (S)-4-(4-((4-(((2-(2,6-dioxopiperidin-3-yl)-1-oxoisoindolin-4-yl)oxy) methyl)-2-fluorophenyl)thio)piperidin-1-yl)-3-fluorobenzonitrile 4 |
| 4' | 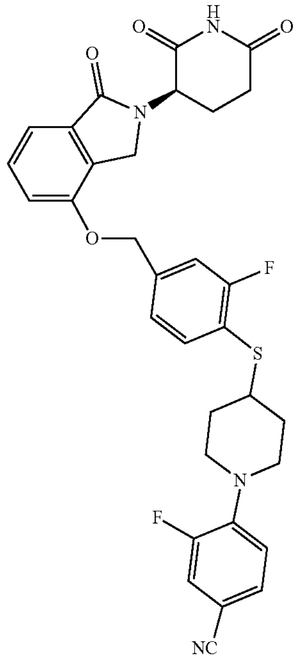 4′ (R)-4-(4-((4-(((2-(2,6-dioxopiperidin-3-yl)-1-oxoisoindolin-4-yl)oxy) methyl)-2-fluorophenyl)thio)piperidin-1-yl)-3-fluorobenzonitrile 4' |

TABLE A-continued

| Typical compounds of the present disclosure include, but are not limited to: | |
|---|---|
| Example No. | Structure and name of compound |
| 4'a | 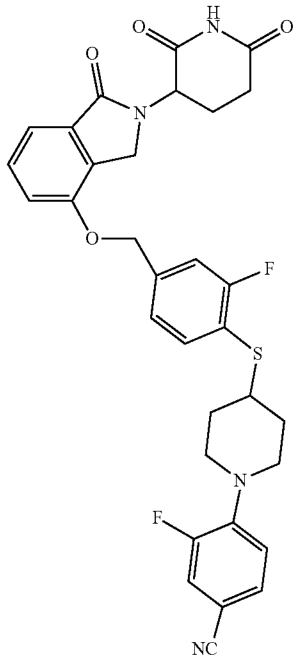<br>4'a<br>4-(4-((4-(((2-(2,6-dioxopiperidin-3-yl)-1-oxoisoindolin-4-yl)oxy)methyl)-2-fluorophenyl)thio)piperidin-1-yl)-3-fluorobenzonitrile 4'a |
| 5 | 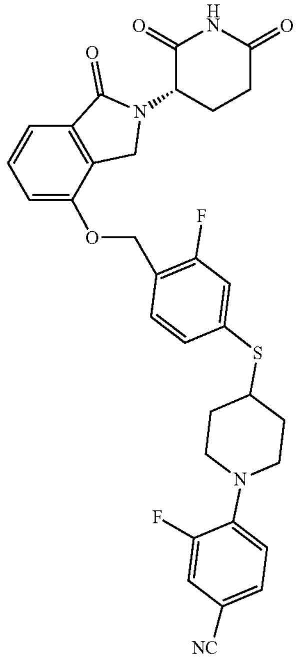<br>5<br>(S)-4-(4-((4-(((2-(2,6-dioxopiperidin-3-yl)-1-oxoisoindolin-4-yl)oxy)methyl)-3-fluorophenyl)thio)piperidin-1-yl)-3-fluorobenzonitrile 5 |

TABLE A-continued
| Example No. | Structure and name of compound |
| --- | --- |
| | Typical compounds of the present disclosure include, but are not limited to: |
| 5' | 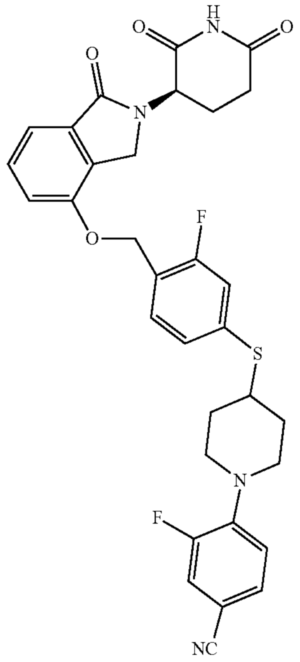 5' (R)-4-(4-((4-(((2-(2,6-dioxopiperidin-3-yl)-1-oxoisoindolin-4-yl)oxy) methyl)-3-fluorophenyl)thio)piperidin-1-yl)-3-fluorobenzonitrile 5' |
| 5'a | 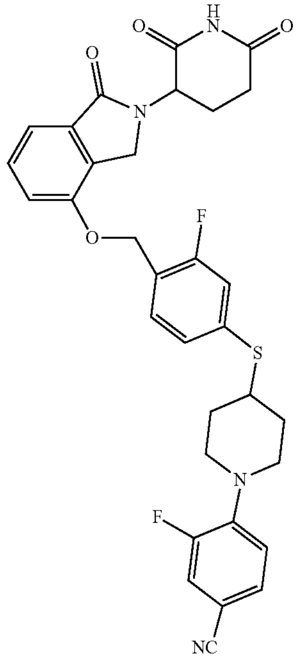 5'a 4-(4-((4-(((2-(2,6-dioxopiperidin-3-yl)-1-oxoisoindolin-4-yl)oxy)methyl)-3-fluorophenyl)thio)piperidin-1-yl)-3-fluorobenzonitrile 5'a |

TABLE A-continued
| Typical compounds of the present disclosure include, but are not limited to: | |
|---|---|
| Example No. | Structure and name of compound |
| 6 | 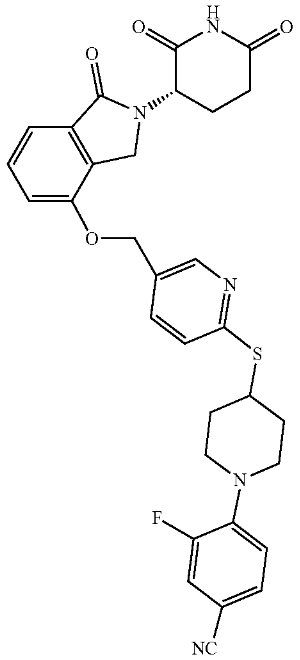<br>6<br>(S)-4-(4-((5-(((2-(2,6-dioxopiperidin-3-yl)-1-oxoisoindolin-4-yl)oxy) methyl)pyridin-2-yl)thio)piperidin-1-yl)-3-fluorobenzonitrile 6 |
| 6' | 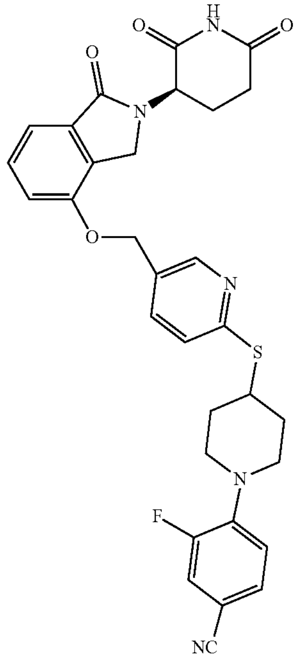<br>6'<br>(R)-4-(4-((5-(((2-(2,6-dioxopiperidin-3-yl)-1-oxoisoindolin-4-yl)oxy) methyl)pyridin-2-yl)thio)piperidin-1-yl)-3-fluorobenzonitrile 6' |

TABLE A-continued
| Typical compounds of the present disclosure include, but are not limited to: | |
|---|---|
| Example No. | Structure and name of compound |
| 6'a | 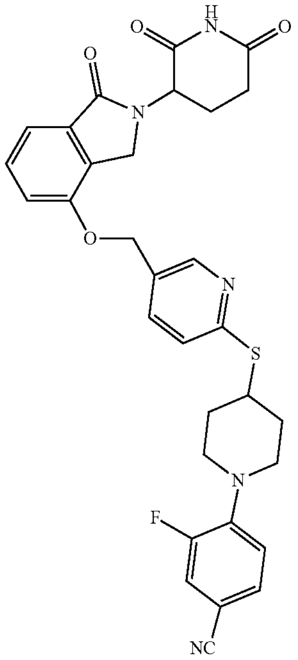 6'a 4-(4-((5-(((2-(2,6-dioxopiperidin-3-yl)-1-oxoisoindolin-4-yl)oxy)methyl)pyridin-2-yl)thio)piperidin-1-yl)-3-fluorobenzonitrile 6'a |
| 7 | 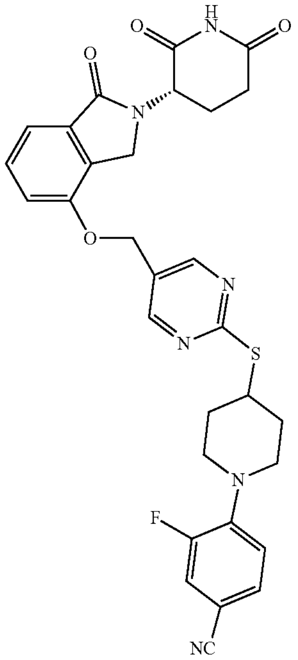 7 (S)-4-(4-((5-(((2-(2,6-dioxopiperidin-3-yl)-1-oxoisoindolin-4-yl)oxy)methyl)pyrimidin-2-yl)thio)piperidin-1-yl)-3-fluorobenzonitrile 7 |

TABLE A-continued
| Typical compounds of the present disclosure include, but are not limited to: | |
|---|---|
| Example No. | Structure and name of compound |
| 7' | 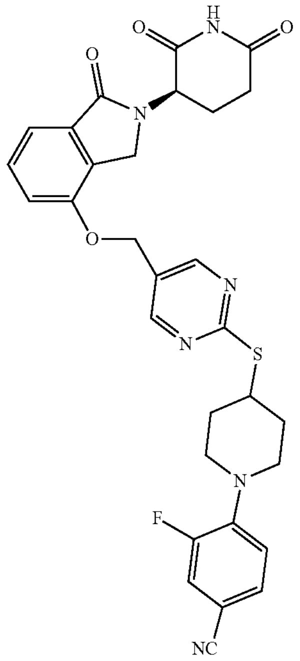 7' (R)-4-(4-((5-(((2-(2,6-dioxopiperidin-3-yl)-1-oxoisoindolin-4-yl)oxy) methyl)pyrimidin-2-yl)thio)piperidin-1-yl)-3-fluorobenzonitrile 7' |
| 7'a | 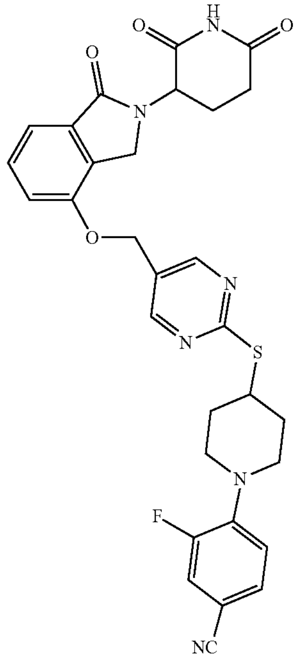 7'a 4-(4-((5-(((2-(2,6-dioxopiperidin-3-yl)-1-oxoisoindolin-4-yl)oxy)methyl) pyrimidin-2-yl)thio)piperidin-1-yl)-3-fluorobenzonitrile 7'a |

TABLE A-continued
| Example No. | Structure and name of compound |
| --- | --- |
| | Typical compounds of the present disclosure include, but are not limited to: |
| 8 | 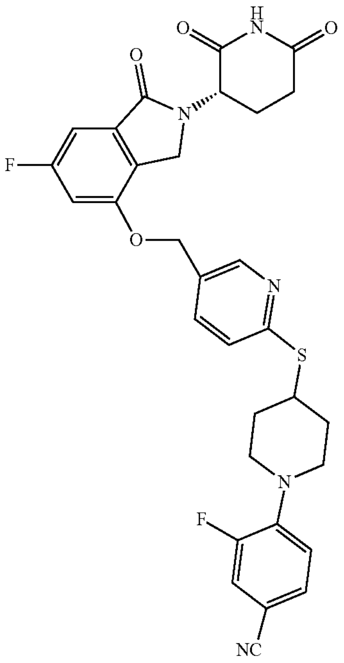 8 (S)-4-(4-((5-(((2-(2,6-dioxopiperidin-3-yl)-6-fluoro-1-oxoisoindolin-4-yl)oxy)methyl)pyridin-2-yl)thio)piperidin-1-yl)-3-fluorobenzonitrile 8 |
| 8' | 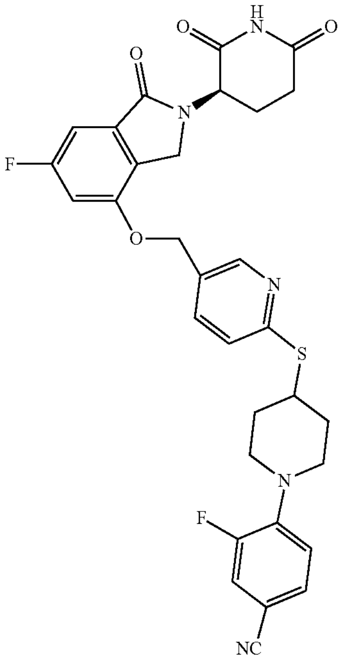 8′ (R)-4-(4-((5-(((2-(2,6-dioxopiperidin-3-yl)-6-fluoro-1-oxoisoindolin-4-yl)oxy)methyl)pyridin-2-yl)thio)piperidin-1-yl)-3-fluorobenzonitrile 8' |

TABLE A-continued
| Example No. | Structure and name of compound |
|---|---|
| | Typical compounds of the present disclosure include, but are not limited to: |
| 8'a | 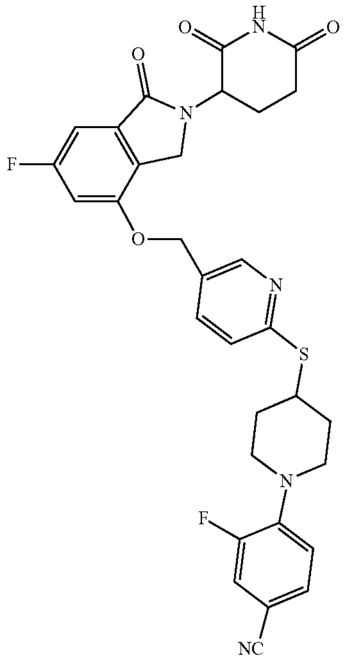 8'a 4-(4-((5-(((2-(2,6-dioxopiperidin-3-yl)-6-fluoro-1-oxoisoindolin-4-yl)oxy)methyl)pyridin-2-yl)thio)piperidin-1-yl)-3-fluorobenzonitrile 8'a |
| 9 | 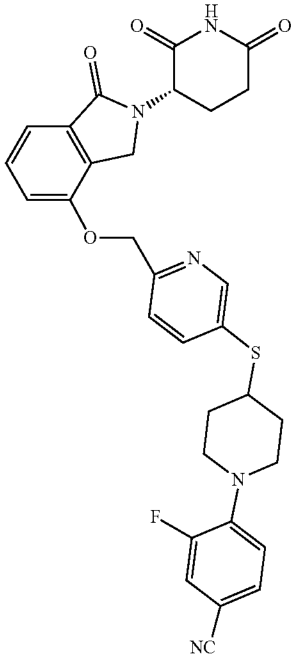 9 (S)-4-(4-((6-(((2-(2,6-dioxopiperidin-3-yl)-1-oxoisoindolin-4-yl)oxy)methyl)pyridin-3-yl)thio)piperidin-1-yl)-3-fluorobenzonitrile 9 |

TABLE A-continued
| Typical compounds of the present disclosure include, but are not limited to: | |
|---|---|
| Example No. | Structure and name of compound |
| 9' | 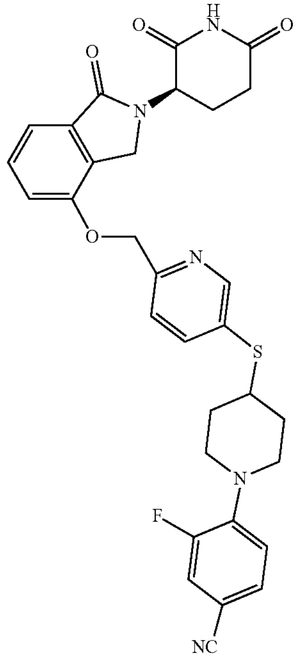 9' (R)-4-(4-((6-(((2-(2,6-dioxopiperidin-3-yl)-1-oxoisoindolin-4-yl)oxy)methyl)pyridin-3-yl)thio)piperidin-1-yl)-3-fluorobenzonitrile 9' |
| 9'a | 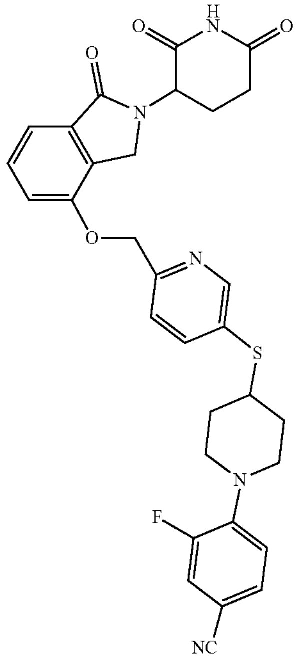 9'a 4-(4-((6-(((2-(2,6-dioxopiperidin-3-yl)-1-oxoisoindolin-4-yl)oxy)methyl)pyridin-3-yl)thio)piperidin-1-yl)-3-fluorobenzonitrile 9'a |

TABLE A-continued

| Typical compounds of the present disclosure include, but are not limited to: | |
|---|---|
| Example No. | Structure and name of compound |
| 10 | 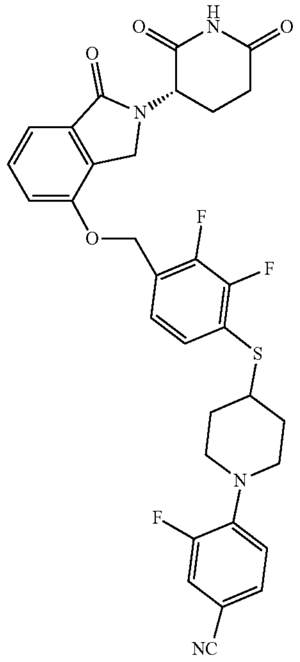<br>10<br>(S)-4-(4-((4-(((2-(2,6-dioxopiperidin-3-yl)-1-oxoisoindolin-4-yl)oxy) methyl)-2,3-difluorophenyl)thio)piperidin-1-yl)-3-fluorobenzonitrile 10 |
| 10' | 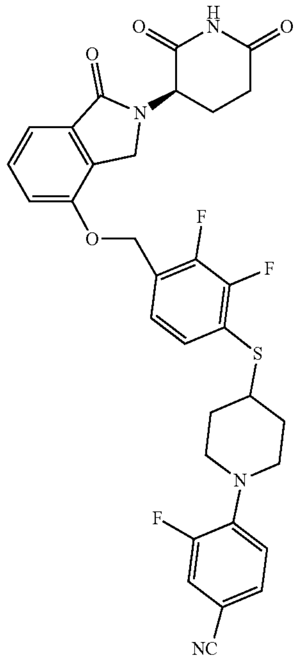<br>10'<br>(R)-4-(4-((4-(((2-(2,6-dioxopiperidin-3-yl)-1-oxoisoindolin-4-yl)oxy) methyl)-2,3-difluorophenyl)thio)piperidin-1-yl)-3-fluorobenzonitrile 10' |

TABLE A-continued

| Typical compounds of the present disclosure include, but are not limited to: | |
|---|---|
| Example No. | Structure and name of compound |
| 10'a | 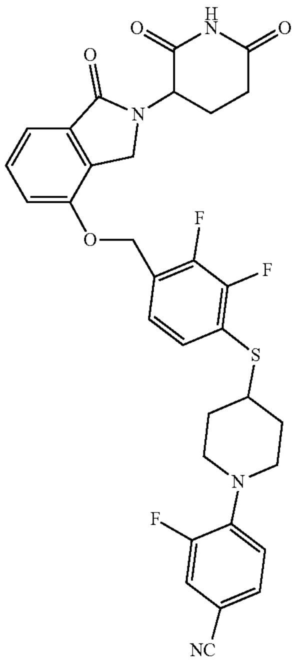<br>10'a<br>4-(4-((4-(((2-(2,6-dioxopiperidin-3-yl)-1-oxoisoindolin-4-yl)oxy)methyl)-2,3-difluorophenyl)thio)piperidin-1-yl)-3-fluorobenzonitrile 10'a |
| 11 | 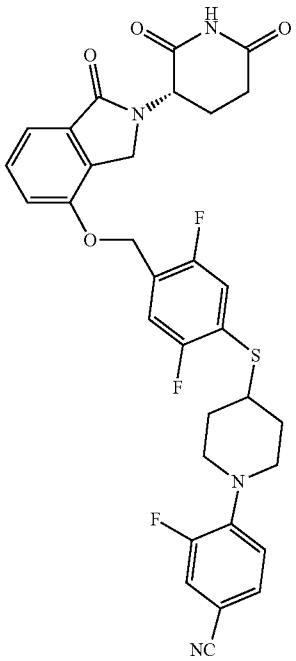<br>11<br>(S)-4-(4-((4-(((2-(2,6-dioxopiperidin-3-yl)-1-oxoisoindolin-4-yl)oxy) methyl)-2,5-difluorophenyl)thio)piperidin-1-yl)-3-fluorobenzonitrile 11 |

TABLE A-continued

| Typical compounds of the present disclosure include, but are not limited to: | |
|---|---|
| Example No. | Structure and name of compound |
| 11' | 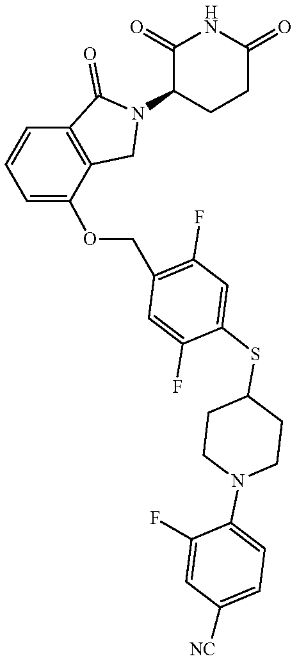<br>11'<br>(R)-4-(4-((4-(((2-(2,6-dioxopiperidin-3-yl)-1-oxoisoindolin-4-yl)oxy) methyl)-2,5-difluorophenyl)thio)piperidin-1-yl)-3-fluorobenzonitrile 11' |
| 11'a | 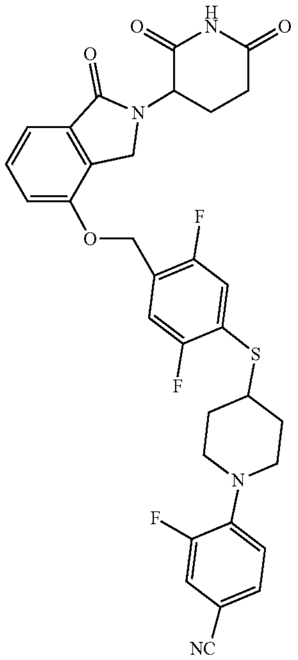<br>11'a<br>4-(4-((4-(((2-(2,6-dioxopiperidin-3-yl)-1-oxoisoindolin-4-yl)oxy)methyl)-2,5-difluorophenyl)thio)piperidin-1-yl)-3-fluorobenzonitrile 11'a |

TABLE A-continued
| Typical compounds of the present disclosure include, but are not limited to: | |
|---|---|
| Example No. | Structure and name of compound |
| 12 | 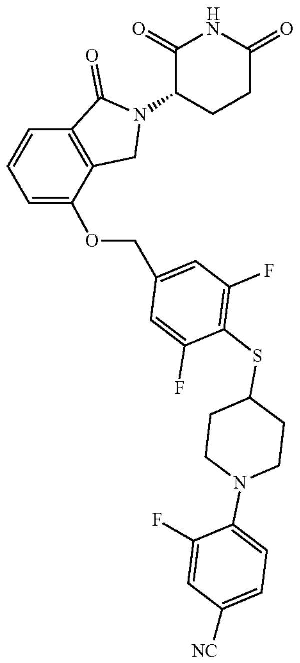 12 (S)-4-(4-((4-(((2-(2,6-dioxopiperidin-3-yl)-1-oxoisoindolin-4-yl)oxy) methyl)-2,6-difluorophenyl)thio)piperidin-1-yl)-3-fluorobenzonitrile 12 |
| 12' | 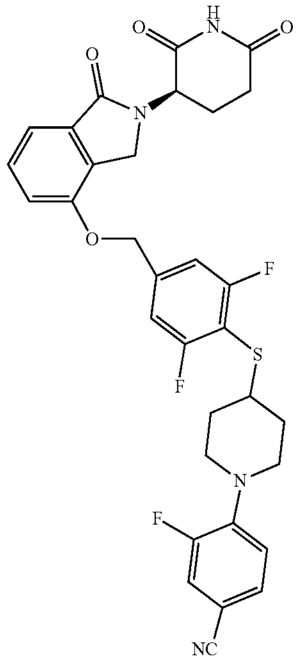 12' (R)-4-(4-((4-(((2-(2,6-dioxopiperidin-3-yl)-1-oxoisoindolin-4-yl)oxy) methyl)-2,6-difluorophenyl)thio)piperidin-1-yl)-3-fluorobenzonitrile 12' |

TABLE A-continued
| Typical compounds of the present disclosure include, but are not limited to: | |
|---|---|
| Example No. | Structure and name of compound |
| 12'a | 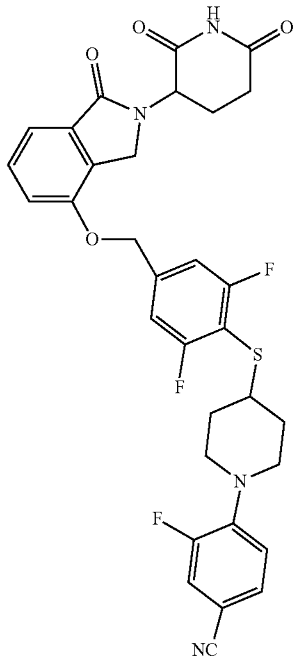 12'a 4-(4-((4-(((2-(2,6-dioxopiperidin-3-yl)-1-oxoisoindolin-4-yl)oxy)methyl)-2,6-difluorophenyl)thio)piperidin-1-yl)-3-fluorobenzonitrile 12'a |
| 13 | 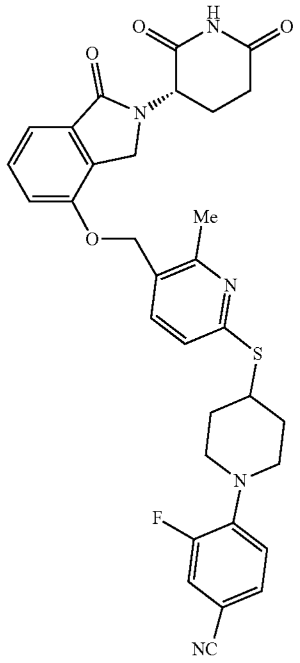 13 (S)-4-(4-((5-(((2-(2,6-dioxopiperidin-3-yl)-1-oxoisoindolin-4-yl)oxy)methyl)-6-methylpyridin-2-yl)thio)piperidin-1-yl)-3-fluorobenzonitrile 13 |

TABLE A-continued

| Typical compounds of the present disclosure include, but are not limited to: | |
|---|---|
| Example No. | Structure and name of compound |
| 13' | 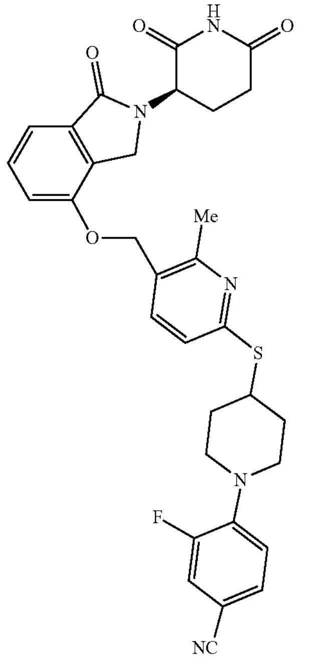<br>13'<br>(R)-4-(4-((5-(((2-(2,6-dioxopiperidin-3-yl)-1-oxoisoindolin-4-yl)oxy) methyl)-6-methylpyridin-2-yl)thio)piperidin-1-yl)-3-fluorobenzonitrile 13' |
| 13'a | 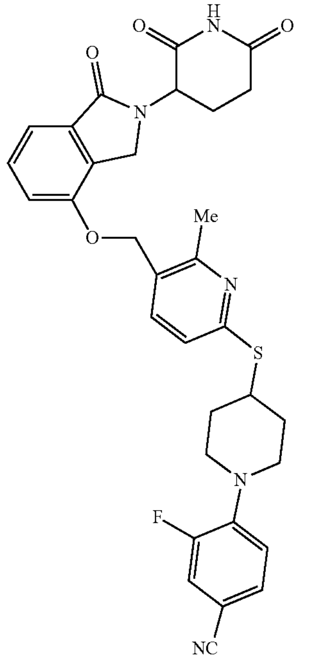<br>13'a<br>4-(4-((5-(((2-(2,6-dioxopiperidin-3-yl)-1-oxoisoindolin-4-yl)oxy)methyl)-6-methylpyridin-2-yl)thio)piperidin-1-yl)-3-fluorobenzonitrile 13'a |

TABLE A-continued
| Example No. | Structure and name of compound |
|---|---|
| | Typical compounds of the present disclosure include, but are not limited to: |
| 14 | 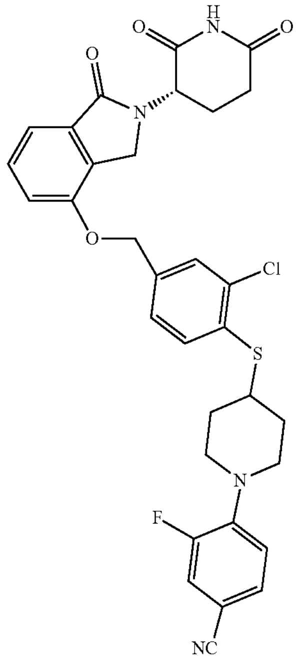 14 (S)-4-(4-((2-chloro-4-(((2-(2,6-dioxopiperidin-3-yl)-1-oxoisoindolin-4-yl)oxy)methyl)phenyl)thio)piperidin-1-yl)-3-fluorobenzonitrile 14 |
| 14' | 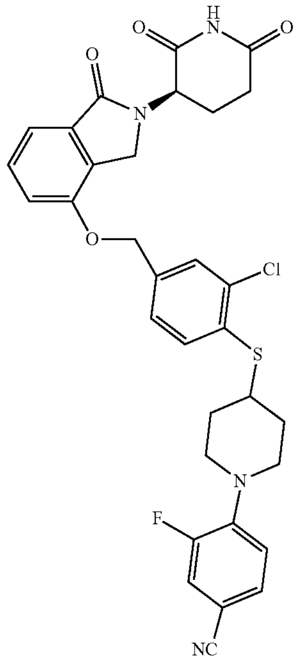 14′ (R)-4-(4-((2-chloro-4-(((2-(2,6-dioxopiperidin-3-yl)-1-oxoisoindolin-4-yl)oxy)methyl)phenyl)thio)piperidin-1-yl)-3-fluorobenzonitrile 14' |

TABLE A-continued
| Typical compounds of the present disclosure include, but are not limited to: | |
|---|---|
| Example No. | Structure and name of compound |
| 14'a | 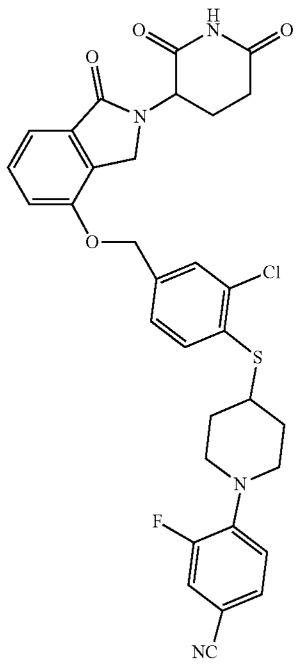 14'a 4-(4-((2-chloro-4-(((2-(2,6-dioxopiperidin-3-yl)-1-oxoisoindolin-4-yl)oxy)methyl)phenyl)thio)piperidin-1-yl)-3-fluorobenzonitrile 14'a |
| 15 | 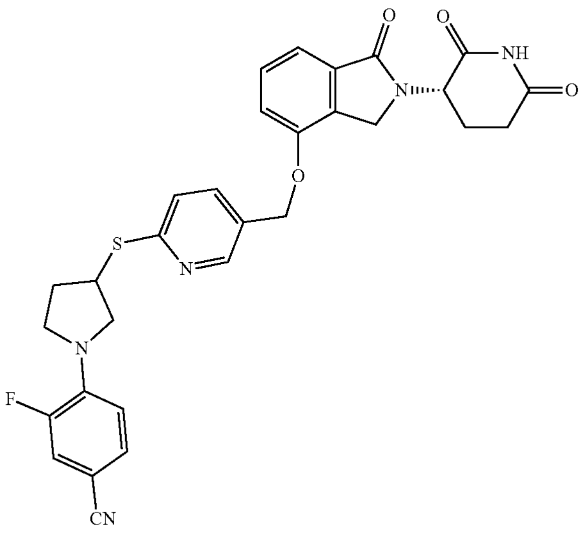 15 (S)-4-(3-((5-(((2-((S)-2,6-dioxopiperidin-3-yl)-1-oxoisoindolin-4-yl)oxy)methyl)pyridin-2-yl)thio)pyrrolidin-1-yl)-3-fluorobenzonitrile 15 |

TABLE A-continued

| Typical compounds of the present disclosure include, but are not limited to: | |
|---|---|
| Example No. | Structure and name of compound |
| 15' | 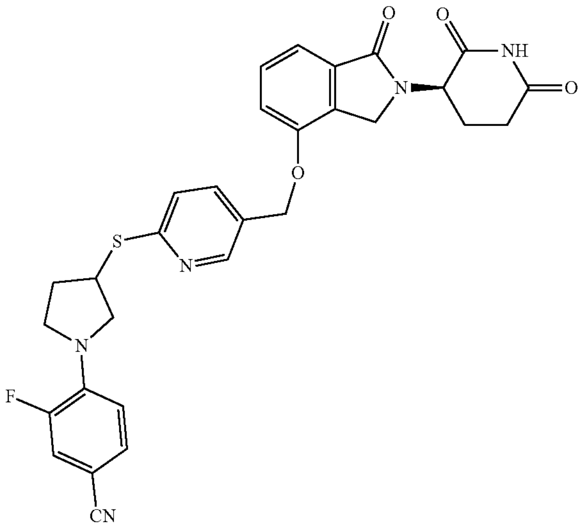<br>15'<br>(R)-4-(3-((5-(((2-((S)-2,6-dioxopiperidin-3-yl)-1-oxoisoindolin-4-yl)oxy)methyl)pyridin-2-yl)thio)pyrrolidin-1-yl)-3-fluorobenzonitrile 15' |
| 15'a | 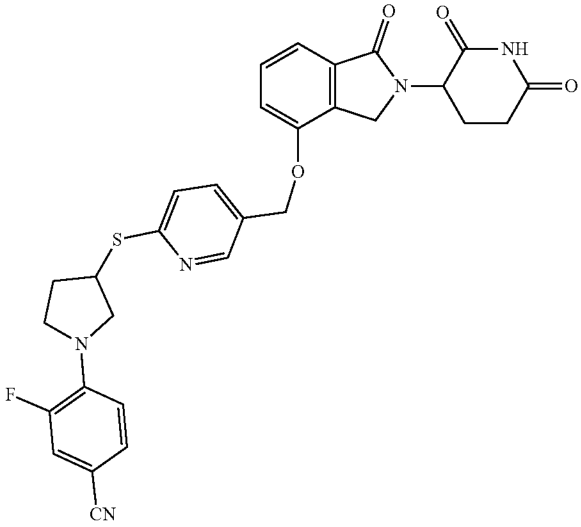<br>15'a<br>4-(3-((5-(((2-((S)-2,6-dioxopiperidin-3-yl)-1-oxoisoindolin-4-yl)oxy)methyl)pyridin-2-yl)thio)pyrrolidin-1-yl)-3-fluorobenzonitrile 15'a |

TABLE A-continued
| Typical compounds of the present disclosure include, but are not limited to: | |
|---|---|
| Example No. | Structure and name of compound |
| 16 | 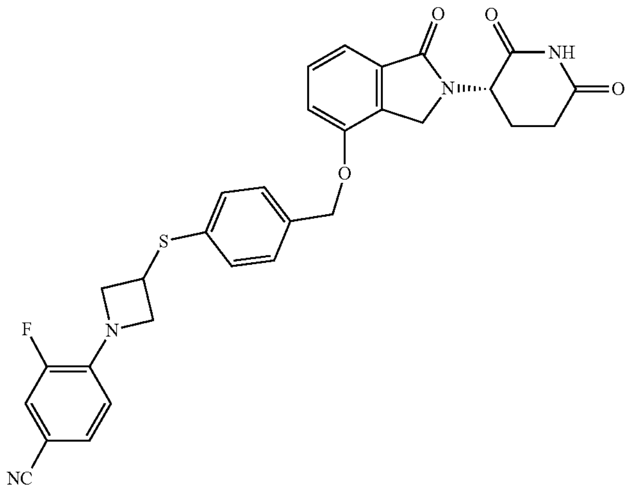 16 (S)-4-(3-((4-(((2-(2,6-dioxopiperidin-3-yl)-1-oxoisoindolin-4-yl)oxy) methyl)phenyl)thio)azetidin-1-yl)-3-fluorobenzonitrile 16 |
| 16' | 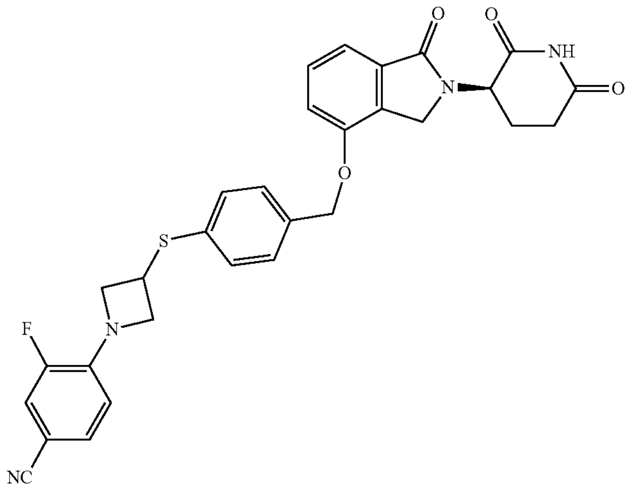 16' (R)-4-(3-((4-(((2-(2,6-dioxopiperidin-3-yl)-1-oxoisoindolin-4-yl)oxy) methyl)phenyl)thio)azetidin-1-yl)-3-fluorobenzonitrile 16' |

TABLE A-continued
| Typical compounds of the present disclosure include, but are not limited to: | |
|---|---|
| Example No. | Structure and name of compound |
| 16'a | 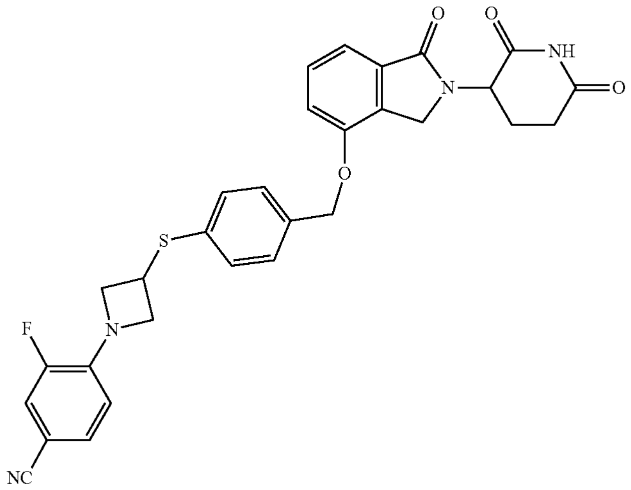<br>16'a<br>4-(3-((4-(((2-(2,6-dioxopiperidin-3-yl)-1-oxoisoindolin-4-yl)oxy) methyl)phenyl)thio)azetidin-1-yl)-3-fluorobenzonitrile 16'a |
| 17 | 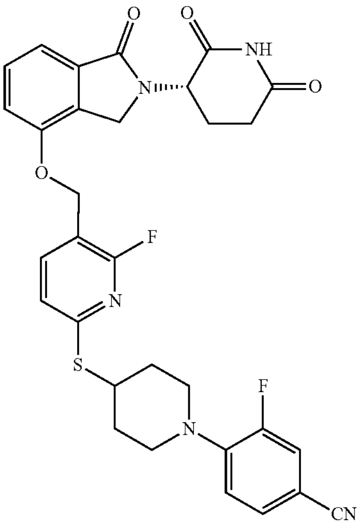<br>17<br>(S)-4-(4-((5-(((2-(2,6-dioxopiperidin-3-yl)-1-oxoisoindolin-4-yl)oxy) methyl)-6-fluoropyridin-2-yl)thio)piperidin-1-yl)-3-fluorobenzonitrile 17 |

TABLE A-continued
| Typical compounds of the present disclosure include, but are not limited to: | |
|---|---|
| Example No. | Structure and name of compound |
| 17' | 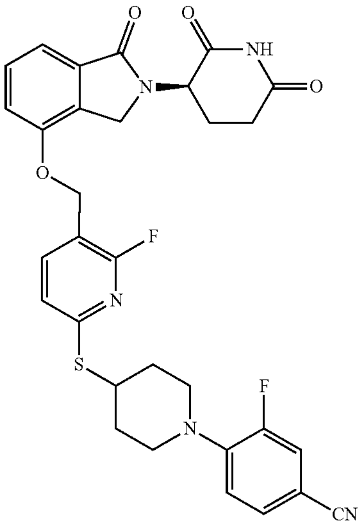 17' (R)-4-(4-((5-(((2-(2,6-dioxopiperidin-3-yl)-1-oxoisoindolin-4-yl)oxy) methyl)-6-fluoropyridin-2-yl)thio)piperidin-1-yl)-3-fluorobenzonitrile 17' |
| 17'a | 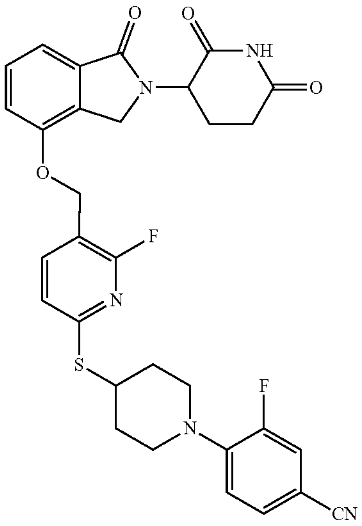 17'a 4-(4-((5-(((2-(2,6-dioxopiperidin-3-yl)-1-oxoisoindolin-4-yl)oxy) methyl)-6-fluoropyridin-2-yl)thio)piperidin-1-yl)-3-fluorobenzonitrile 17'a |

TABLE A-continued

| Typical compounds of the present disclosure include, but are not limited to: | |
|---|---|
| Example No. | Structure and name of compound |
| 18 | 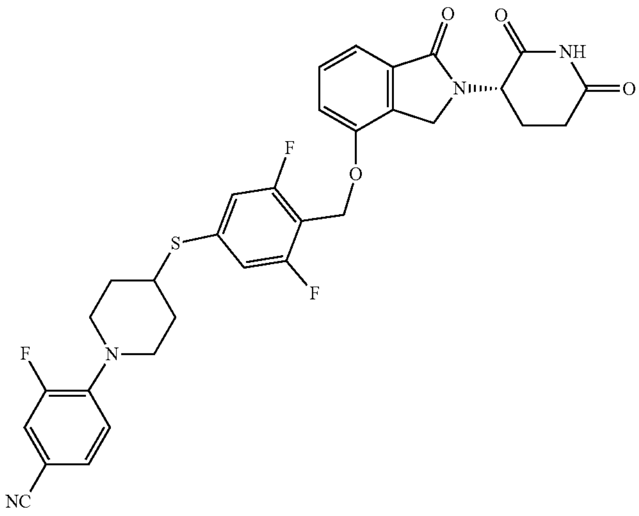<br>18<br>(S)-4-(4-((4-(((2-(2,6-dioxopiperidin-3-yl)-1-oxoisoindolin-4-yl)oxy) methyl)-3,5-difluorophenyl)thio)piperidin-1-yl)-3-fluorobenzonitrile 18 |
| 18' | 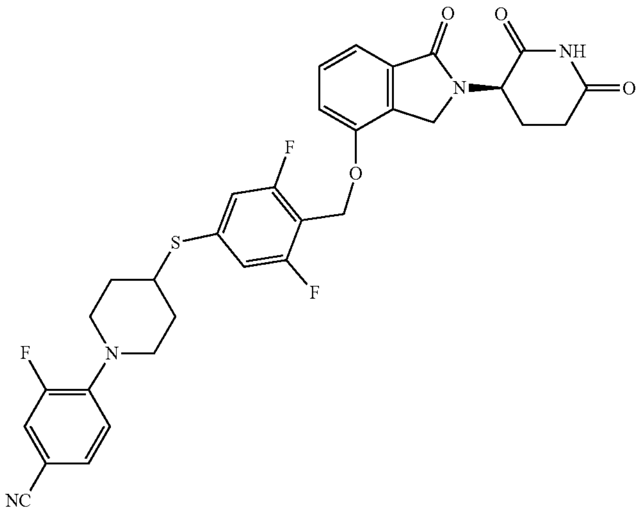<br>18'<br>(R)-4-(4-((4-(((2-(2,6-dioxopiperidin-3-yl)-1-oxoisoindolin-4-yl)oxy) methyl)-3,5-difluorophenyl)thio)piperidin-1-yl)-3-fluorobenzonitrile 18' |

TABLE A-continued

| Typical compounds of the present disclosure include, but are not limited to: | |
|---|---|
| Example No. | Structure and name of compound |
| 18'a | 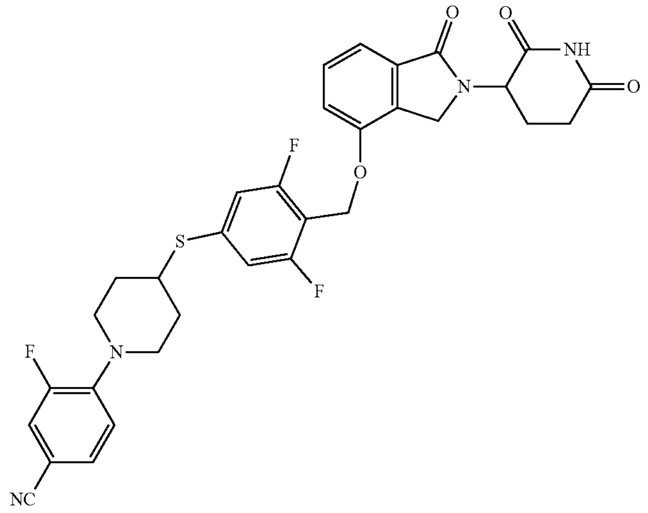<br>18'a<br>4-(4-((4-(((2-(2,6-dioxopiperidin-3-yl)-1-oxoisoindolin-4-yl)oxy) methyl)-3,5-difluorophenyl)thio)piperidin-1-yl)-3-fluorobenzonitrile 18'a |

Another aspect of the present disclosure relates to a compound of general formula (IA) or a tautomer, mesomer, racemate, enantiomer or diastereomer thereof or a mixture thereof, or a salt thereof, (IA)

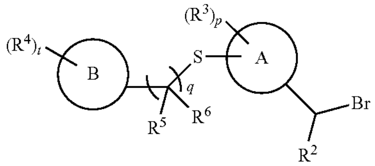

wherein:

ring A is selected from the group consisting of phenyl, pyridinyl and pyrimidinyl; preferably phenyl;

ring B is heterocyclyl; preferably 3-membered to 8-membered heterocyclyl; and more preferably piperidinyl, pyrrolidinyl or azetidinyl; and $R^2$ to $R^6$, p, q and t are as defined in general formula (I).

Another aspect of the present disclosure relates to a compound of general formula (IIA) or a tautomer, mesomer, racemate, enantiomer or diastereomer thereof or a mixture thereof, or a salt thereof, (IIA)

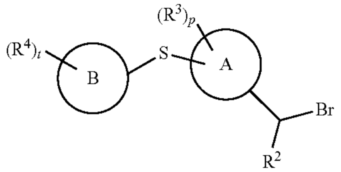

wherein:

ring A is selected from the group consisting of phenyl, pyridinyl and pyrimidinyl; preferably phenyl;

ring B is heterocyclyl; preferably 3-membered to 8-membered heterocyclyl; and more preferably piperidinyl, pyrrolidinyl or azetidinyl; and $R^2$ to $R^4$, p and t are as defined in general formula (II).

Another aspect of the present disclosure relates to a compound of general formula (IIGA) or a tautomer, mesomer, racemate, enantiomer or diastereomer thereof or a mixture thereof, or a salt thereof, (IIGA)

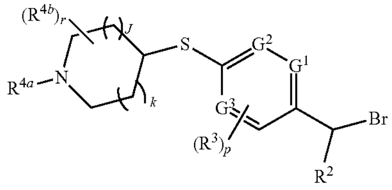

wherein:

$G^1$, $G^2$, $G^3$, $R^2$, $R^3$, $R^{4a}$, $R^{4b}$, J, k, p and r are as defined in general formula (IIG).

Another aspect of the present disclosure relates to a compound of general formula (IIIA) or a tautomer, mesomer, racemate, enantiomer or diastereomer thereof or a mixture thereof, or a salt thereof, (IIIA)

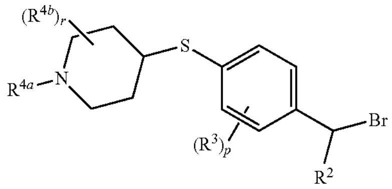

wherein:

$R^2$, $R^3$, $R^{4a}$, $R^{4b}$, p and r are as defined in general formula (III).

Typical intermediate compounds of the present disclosure include, but are not limited to:

| Example No. | Structure and name of compound | |
|---|---|---|
| 1f | 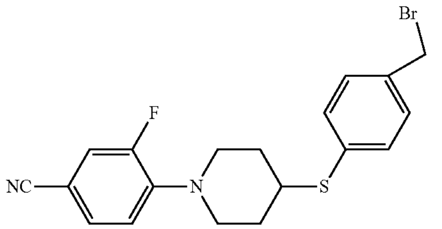 [SMILES: N#Cc1ccc(N2CCC(Sc3ccc(CBr)cc3)CC2)c(F)c1]<br>4-(4-((4-(bromomethyl)phenyl)thio)piperidin-1-yl)-3-fluorobenzonitrile 1f | 1f |
| 4f | 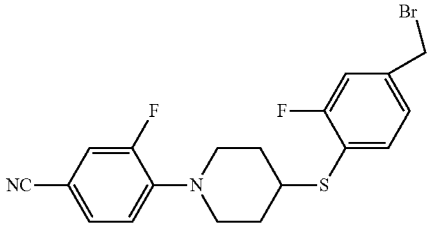 [SMILES: N#Cc1ccc(N2CCC(Sc3ccc(CBr)cc3F)CC2)c(F)c1]<br>4-(4-((4-(bromomethyl)-2-fluorophenyl)thio)piperidin-1-yl)-3-fluorobenzo nitrile 4f | 4f |
| | 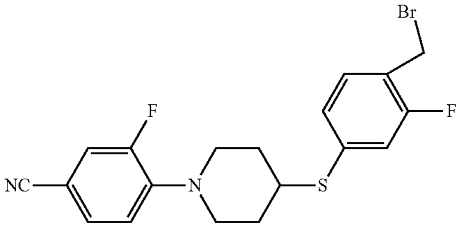 [SMILES: N#Cc1ccc(N2CCC(Sc3ccc(CBr)c(F)c3)CC2)c(F)c1]<br>4-(4-((4-(bromomethyl)-3-fluorophenyl)thio)piperidin-1-yl)-3-fluorobenzo nitrile | |
| 6f | 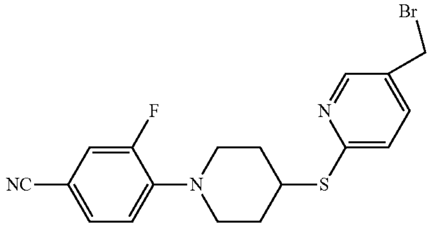<br>4-(4-((5-(bromomethyl)pyridin-2-yl)thio)piperidin-1-yl)-3-fluorobenzonitrile | 6f |
| | 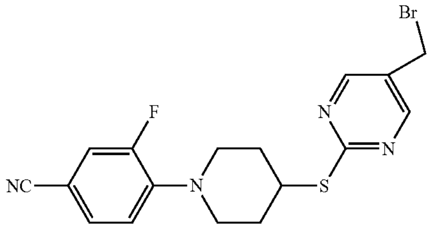 [SMILES: N#Cc1ccc(N2CCC(Sc3ncc(CBr)cn3)CC2)c(F)c1]<br>4-(4-((5-(bromomethyl)pyrimidin-2-yl)thio)piperidin-1-yl)-3-fluorobenzonitrile | |

-continued

| Example No. | Structure and name of compound |
|---|---|
| | 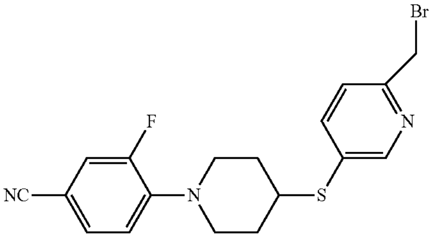 [SMILES: N#Cc1ccc(N2CCC(Sc3ccc(CBr)nc3)CC2)c(F)c1] 4-(4-((6-(bromomethyl)pyridin-3-yl)thio)piperidin-1-yl)-3-fluorobenzonitrile |
| | 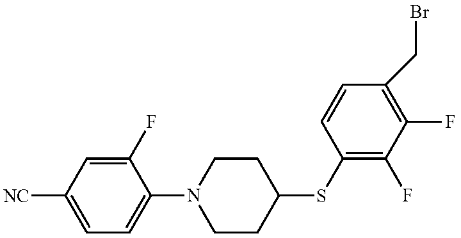 [SMILES: N#Cc1ccc(N2CCC(Sc3ccc(CBr)c(F)c3F)CC2)c(F)c1] 4-(4-((4-(bromomethyl)-2,3-difluorophenyl)thio)piperidin-1-yl)-3-fluorobenzo nitrile |
| | 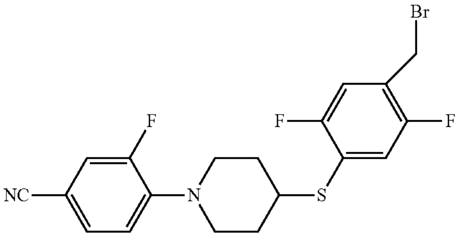 [SMILES: N#Cc1ccc(N2CCC(Sc3cc(F)c(CBr)cc3F)CC2)c(F)c1] 4-(4-((4-(bromomethyl)-2,5-difluorophenyl)thio)piperidin-1-yl)-3-fluorobenzo nitrile |
| | 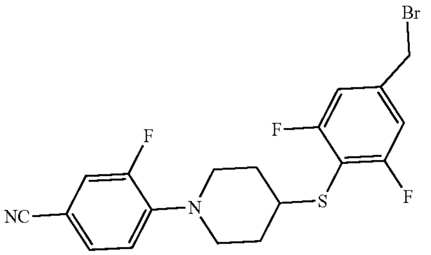 [SMILES: N#Cc1ccc(N2CCC(Sc3c(F)cc(CBr)cc3F)CC2)c(F)c1] 4-(4-((4-(bromomethyl)-2,6-difluorophenyl)thio)piperidin-1-yl)-3-fluorobenzo nitrile |
| | 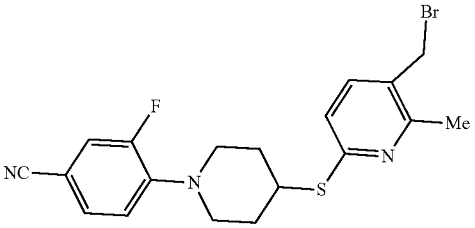 [SMILES: Cc1nc(SC2CCN(c3ccc(C#N)cc3F)CC2)ccc1CBr] 4-(4-((5-(bromomethyl)-6-methylpyridin-2-yl)thio)piperidin-1-yl)-3-fluoro benzonitrile |

-continued
| Example No. | Structure and name of compound |
|---|---|
| | 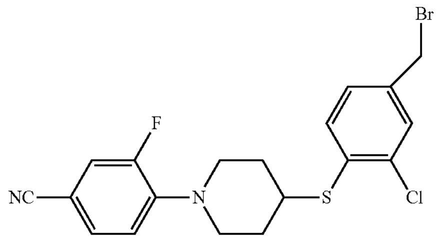 [SMILES: N#Cc1ccc(N2CCC(Sc3ccc(CBr)cc3Cl)CC2)c(F)c1]<br>4-(4-((4-(bromomethyl)-2-chlorophenyl)thio)piperidin-1-yl)-3-fluorobenzo nitrile |
| | 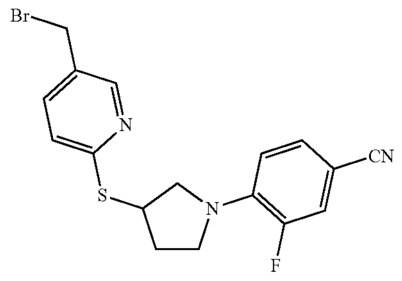 [SMILES: N#Cc1ccc(N2CCC(Sc3ccc(CBr)cn3)C2)c(F)c1]<br>4-(3-((5-(bromomethyl)pyridin-2-yl)thio)pyrrolidin-1-yl)-3-fluorobenzonitrile |
| | 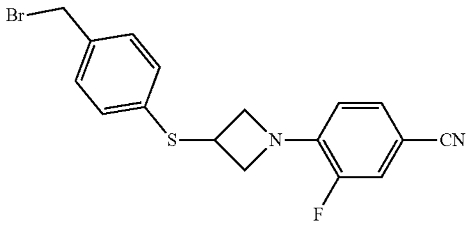 [SMILES: N#Cc1ccc(N2CC(Sc3ccc(CBr)cc3)C2)c(F)c1]<br>4-(3-((4-(bromomethyl)phenyl)thio)azetidin-1-yl)-3-fluorobenzonitrile |
| 17f | 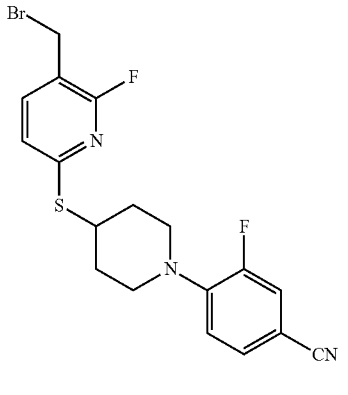 [SMILES: N#Cc1ccc(N2CCC(Sc3ccc(CBr)c(F)n3)CC2)c(F)c1]<br>4-(4-((5-(bromomethyl)-6-fluoropyridin-2-yl)thio)piperidin-1-yl)-3-fluorobenzo nitrile 17f |

-continued

| Example No. | Structure and name of compound |
|---|---|
| | 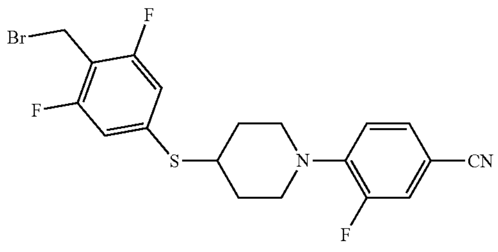 [SMILES: N#Cc1ccc(N2CCC(Sc3cc(F)c(CBr)c(F)c3)CC2)c(F)c1] 4-(4-((4-(bromomethyl)-3,5-difluorophenyl)thio)piperidin-1-yl)-3-fluorobenzonitrile |

Another aspect of the present disclosure relates to a compound of general formula (IC) or a tautomer, mesomer, racemate, enantiomer or diastereomer thereof or a mixture thereof, or a salt thereof, (IC)

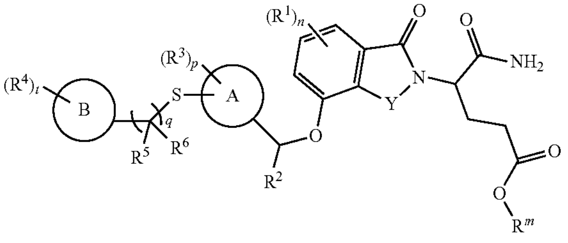

wherein:

$R^m$ is $C_{1-6}$ alkyl; preferably tert-butyl; and ring A, ring B, Y, $R^1$ to $R^6$, n, p, q and t are as defined in general formula (I).

Another aspect of the present disclosure relates to a compound of general formula (I-1C) or a tautomer, mesomer, racemate, enantiomer or diastereomer thereof or a mixture thereof, or a salt thereof, (I-1C)

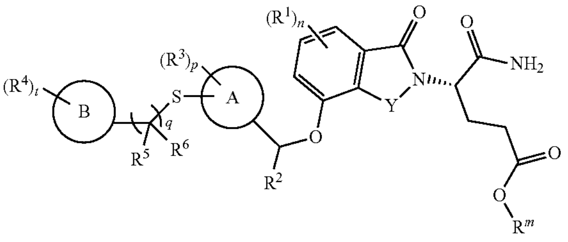

wherein:

$R^m$ is $C_{1-6}$ alkyl; preferably tert-butyl; and ring A, ring B, Y, $R^1$ to $R^6$, n, p, q and t are as defined in general formula (I-1).

Another aspect of the present disclosure relates to a compound of general formula (IIC) or a tautomer, mesomer, racemate, enantiomer or diastereomer thereof or a mixture thereof, or a salt thereof, (IIC)

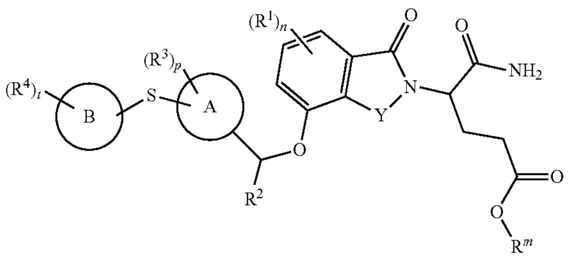

wherein:

$R^m$ is $C_{1-6}$ alkyl; preferably tert-butyl; and ring A, ring B, Y, $R^1$ to $R^4$, n, p and t are as defined in general formula (II).

Another aspect of the present disclosure relates to a compound of general formula (II-1C) or a tautomer, mesomer, racemate, enantiomer or diastereomer thereof or a mixture thereof, or a salt thereof, (II-1C)

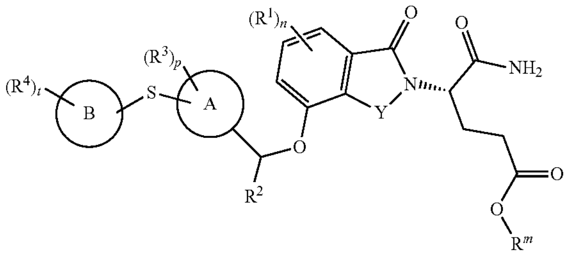

wherein:

$R^m$ is $C_{1-6}$ alkyl; preferably tert-butyl; and ring A, ring B, Y, $R^1$ to $R^4$, n, p and t are as defined in general formula (II-1).

Another aspect of the present disclosure relates to a compound of general formula (IIGC) or a tautomer, mesomer, racemate, enantiomer or diastereomer thereof or a mixture thereof, or a salt thereof, (IIGC)

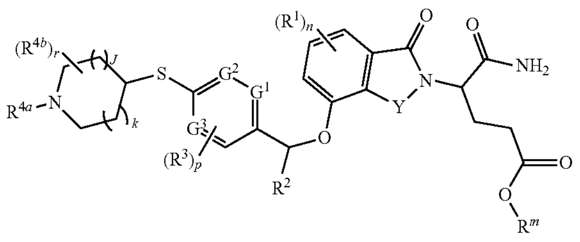

wherein:

$R^m$ is $C_{1-6}$ alkyl; preferably tert-butyl; and $G^1$, $G^2$, $G^3$, Y, $R^1$ to $R^3$, $R^{4a}$, $R^{4b}$, J, k, r, n and p are as defined in general formula (IIG).

Another aspect of the present disclosure relates to a compound of general formula (IIGC-1) or a tautomer, mesomer, racemate, enantiomer or diastereomer thereof or a mixture thereof, or a salt thereof, (IIGC-1)

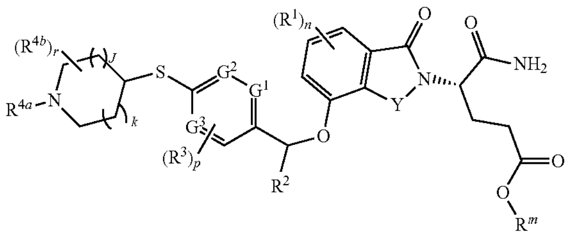

wherein:

$R^m$ is $C_{1-6}$ alkyl; preferably tert-butyl; and $G^1$, $G^2$, $G^3$, Y, $R^1$ to $R^3$, $R^{4a}$, $R^{4b}$, J, k, r, n and p are as defined in general formula (IIG-1).

Another aspect of the present disclosure relates to a compound of general formula (IIIC) or a tautomer, mesomer, racemate, enantiomer or diastereomer thereof or a mixture thereof, or a salt thereof, (IIIC)

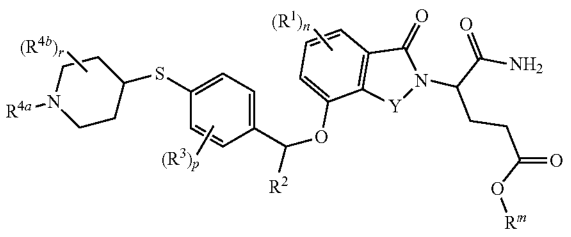

wherein:

$R^m$ is $C_{1-6}$ alkyl; preferably tert-butyl; and

Y, $R^1$ to $R^3$, $R^{4a}$, $R^{4b}$, r, n and p are as defined in general formula (III).

Another aspect of the present disclosure relates to a compound of general formula (III-1C) or a tautomer, mesomer, racemate, enantiomer or diastereomer thereof or a mixture thereof, or a salt thereof, (III-1C)

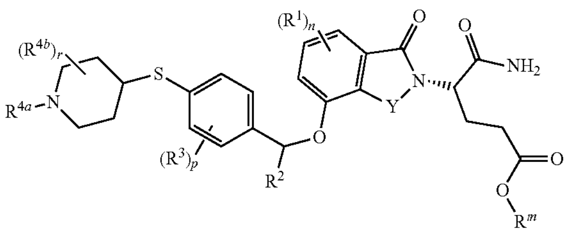

wherein:

$R^m$ is $C_{1-6}$ alkyl; preferably tert-butyl; and

Y, $R^1$ to $R^3$, $R^{4a}$, $R^{4b}$, r, n and p are as defined in general formula (III-1).

Typical intermediate compounds of the present disclosure include, but are not limited to:

| Example No. | Structure and name of compound |
|---|---|
| | 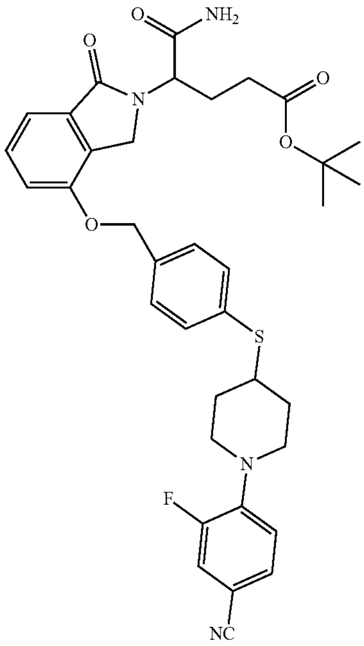 [SMILES: CC(C)(C)OC(=O)CCC(C(N)=O)N1Cc2c(OCc3ccc(SC4CCN(c5ccc(C#N)cc5F)CC4)cc3)cccc2C1=O]<br>Tert-butyl<br>5-amino-4-(4-((4-((1-(4-cyano-2-fluorophenyl)piperidin-4-yl)thio)<br>benzyl)oxy)-1-oxoisoindolin-2-yl)-5-oxopentanoate |
| 3b | 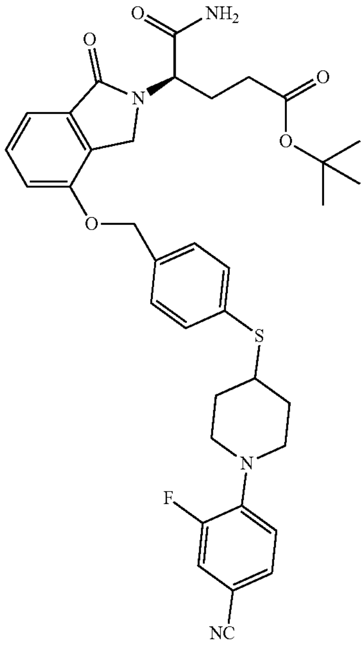 [SMILES: CC(C)(C)OC(=O)CC[C@H](C(N)=O)N1Cc2c(OCc3ccc(SC4CCN(c5ccc(C#N)cc5F)CC4)cc3)cccc2C1=O]<br>Tert-butyl<br>(S)-5-amino-4-(4-((4-((1-(4-cyano-2-fluorophenyl)piperidin-4-yl)thio)<br>benzyl)oxy)-1-oxoisoindolin-2-yl)-5-oxopentanoate 3b |
3b -continued
| Example No. | Structure and name of compound | |
|---|---|---|
| 4g | 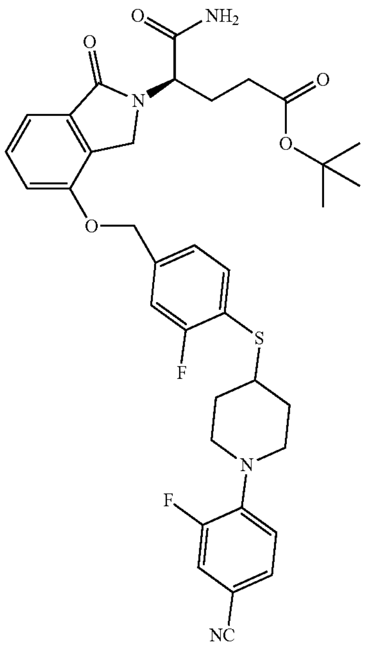 [SMILES: CC(C)(C)OC(=O)CC[C@H](C(N)=O)N1Cc2c(OCc3ccc(SC4CCN(c5ccc(C#N)cc5F)CC4)c(F)c3)cccc2C1=O] Tert-butyl (S)-5-amino-4-(4-((4-((1-(4-cyano-2-fluorophenyl)piperidin-4-yl)thio)-3-fluorobenzyl)oxy)-1-oxoisoindolin-2-yl)-5-oxopentanoate 4g | 4g |
| | 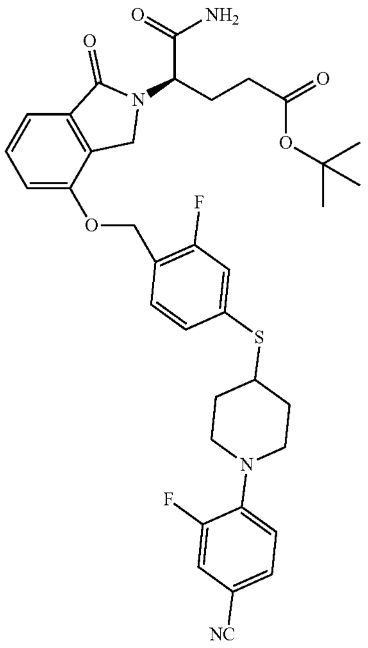 [SMILES: CC(C)(C)OC(=O)CC[C@H](C(N)=O)N1Cc2c(OCc3ccc(SC4CCN(c5ccc(C#N)cc5F)CC4)cc3F)cccc2C1=O] Tert-butyl (S)-5-amino-4-(4-((4-((1-(4-cyano-2-fluorophenyl)piperidin-4-yl)thio)-2-fluorobenzyl)oxy)-1-oxoisoindolin-2-yl)-5-oxopentanoate | |

-continued
| Example No. | Structure and name of compound |
| --- | --- |
| | 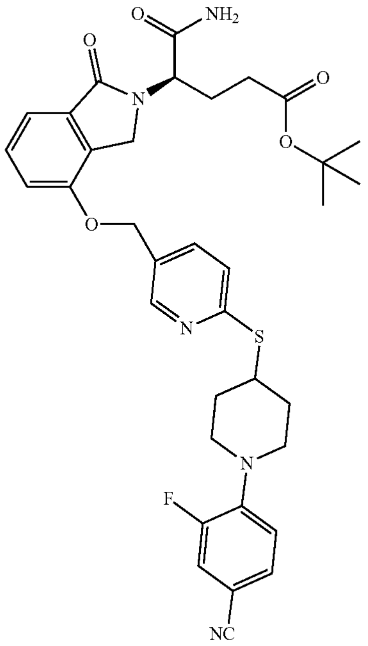 [SMILES: CC(C)(C)OC(=O)CC[C@H](C(N)=O)N1Cc2c(OCc3ccc(SC4CCN(c5ccc(C#N)cc5F)CC4)nc3)cccc2C1=O]<br>Tert-butyl<br>(S)-5-amino-4-(4-((6-((1-(4-cyano-2-fluorophenyl)piperidin-4-yl)thio)<br>pyridin-3-yl)methoxy)-1-oxoisoindolin-2-yl)-5-oxopentanoate 6g |
| | 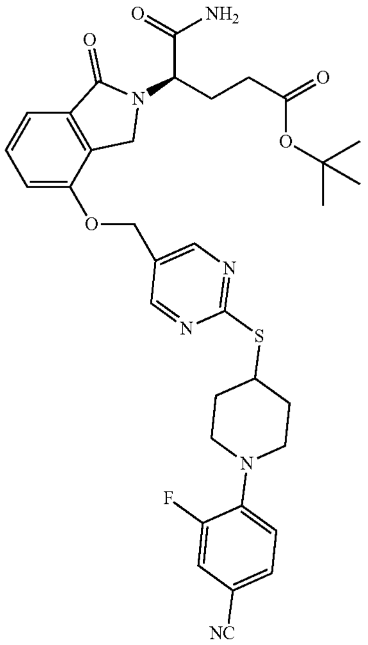 [SMILES: CC(C)(C)OC(=O)CC[C@H](C(N)=O)N1Cc2c(OCc3cnc(SC4CCN(c5ccc(C#N)cc5F)CC4)nc3)cccc2C1=O]<br>Tert-butyl<br>(S)-5-amino-4-(4-((2-((1-(4-cyano-2-fluorophenyl)piperidin-4-yl)thio)<br>pyrimidin-5-yl)methoxy)-1-oxoisoindolin-2-yl)-5-oxopentanoate |

-continued
| Example No. | Structure and name of compound |
|---|---|
| | 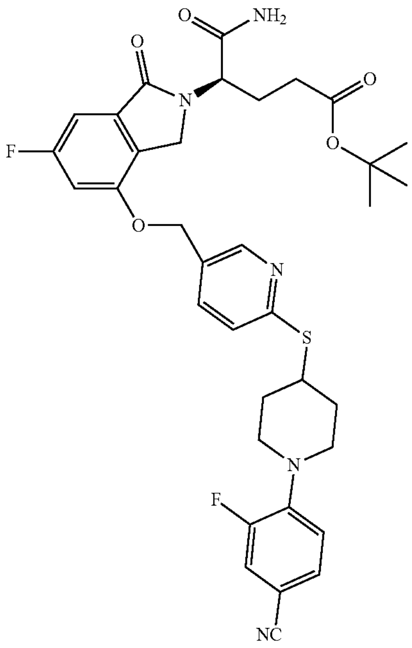 [SMILES: CC(C)(C)OC(=O)CC[C@H](C(N)=O)N1Cc2c(OCc3ccc(SC4CCN(c5ccc(C#N)cc5F)CC4)nc3)cc(F)cc2C1=O]<br>Tert-butyl (S)-5-amino-4-(4-((6-((1-(4-cyano-2-fluorophenyl)piperidin-4-yl)thio) pyridin-3-yl)methoxy)-6-fluoro-1-oxoisoindolin-2-yl)-5-oxopentanoate |
| | 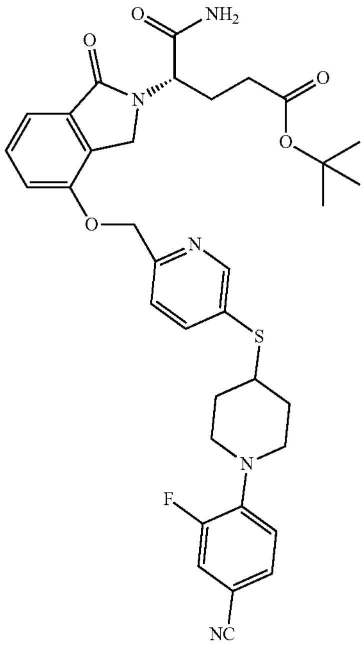 [SMILES: CC(C)(C)OC(=O)CC[C@@H](C(N)=O)N1Cc2c(OCc3ccc(SC4CCN(c5ccc(C#N)cc5F)CC4)cn3)cccc2C1=O]<br>Tert-butyl (S)-5-amino-4-(4-((5-((1-(4-cyano-2-fluorophenyl)piperidin-4-yl)thio) pyridin-2-yl)methoxy)-1-oxoisoindolin-2-yl)-5-oxopentanoate |

-continued
| Example No. | Structure and name of compound |
|---|---|
| | 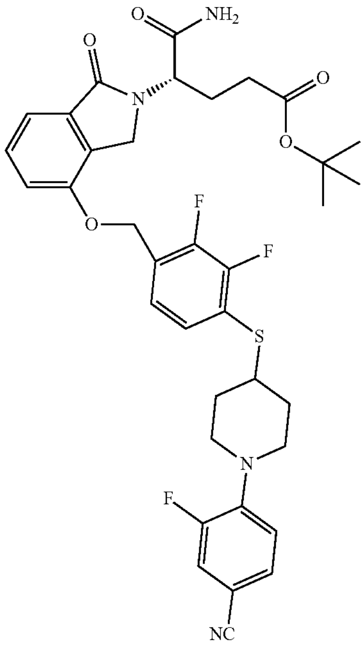 [SMILES: CC(C)(C)OC(=O)CC[C@@H](C(N)=O)N1Cc2c(OCc3ccc(SC4CCN(c5ccc(C#N)cc5F)CC4)c(F)c3F)cccc2C1=O] Tert-butyl (S)-5-amino-4-(4-((4-((1-(4-cyano-2-fluorophenyl)piperidin-4-yl)thio)-2,3-difluorobenzyl)oxy)-1-oxoisoindolin-2-yl)-5-oxopentanoate |
| | 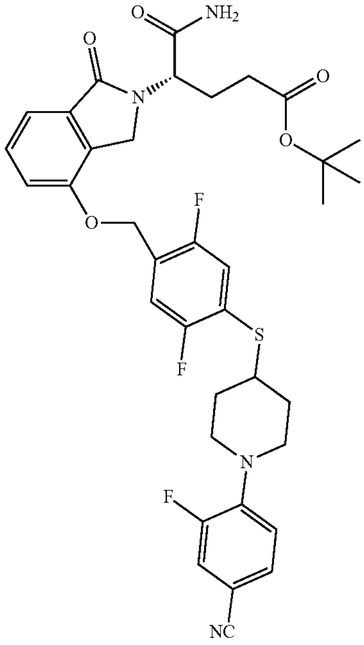 [SMILES: CC(C)(C)OC(=O)CC[C@@H](C(N)=O)N1Cc2c(OCc3cc(F)c(SC4CCN(c5ccc(C#N)cc5F)CC4)cc3F)cccc2C1=O] Tert-butyl (S)-5-amino-4-(4-((4-((1-(4-cyano-2-fluorophenyl)piperidin-4-yl)thio)-2,5-difluorobenzyl)oxy)-1-oxoisoindolin-2-yl)-5-oxopentanoate |

-continued
| Example No. | Structure and name of compound |
|---|---|
| | 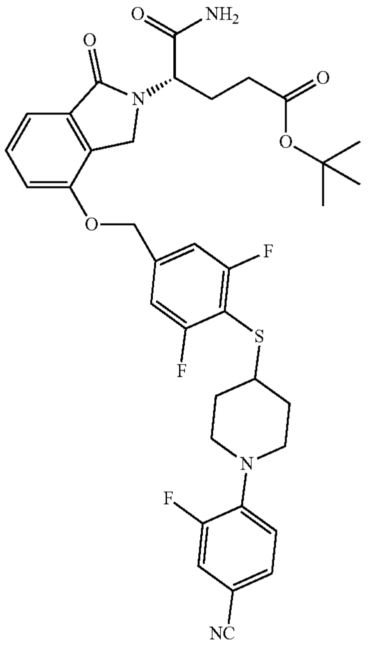 [SMILES: CC(C)(C)OC(=O)CC[C@@H](C(N)=O)N1Cc2c(OCc3cc(F)c(SC4CCN(c5ccc(C#N)cc5F)CC4)c(F)c3)cccc2C1=O]<br>Tert-butyl (S)-5-amino-4-(4-((4-((1-(4-cyano-2-fluorophenyl)piperidin-4-yl)thio)-3,5-difluorobenzyl)oxy)-1-oxoisoindolin-2-yl)-5-oxopentanoate |
| | 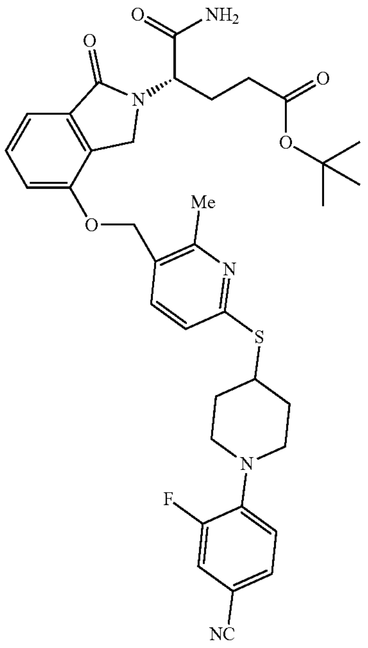 [SMILES: Cc1nc(SC2CCN(c3ccc(C#N)cc3F)CC2)ccc1COc1cccc2c1CN([C@@H](CCC(=O)OC(C)(C)C)C(N)=O)C2=O]<br>Tert-butyl (S)-5-amino-4-(4-((6-((1-(4-cyano-2-fluorophenyl)piperidin-4-yl)thio)-2-methylpyridin-3-yl)methoxy)-1-oxoisoindolin-2-yl)-5-oxopentanoate |

-continued
| Example No. | Structure and name of compound |
|---|---|
| | 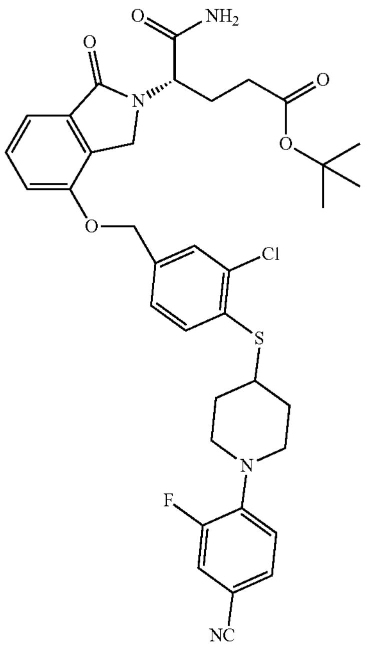 [SMILES: CC(C)(C)OC(=O)CC[C@@H](C(N)=O)N1Cc2c(OCc3ccc(SC4CCN(c5ccc(C#N)cc5F)CC4)c(Cl)c3)cccc2C1=O] Tert-butyl (S)-5-amino-4-(4-((3-chloro-4-((1-(4-cyano-2-fluorophenyl)piperidin-4-yl)thio)benzyl)oxy)-1-oxoisoindolin-2-yl)-5-oxopentanoate |
| | 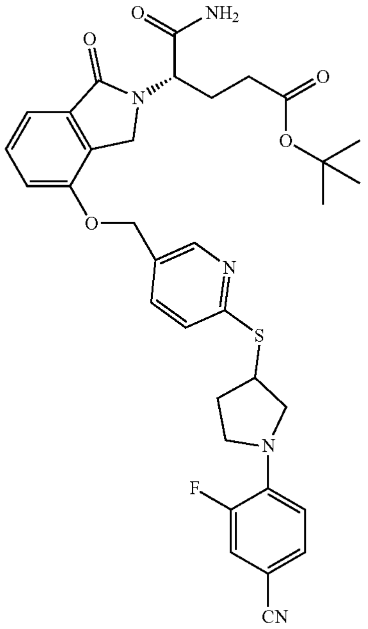 [SMILES: CC(C)(C)OC(=O)CC[C@@H](C(N)=O)N1Cc2c(OCc3ccc(SC4CCN(c5ccc(C#N)cc5F)C4)nc3)cccc2C1=O] Tert-butyl (4S)-5-amino-4-(4-((6-((1-(4-cyano-2-fluorophenyl)pyrrolidin-3-yl) thio) pyridin-3-yl)methoxy)-1-oxoisoindolin-2-yl)-5-oxopentanoate |

-continued
| Example No. | Structure and name of compound |
| --- | --- |
| | 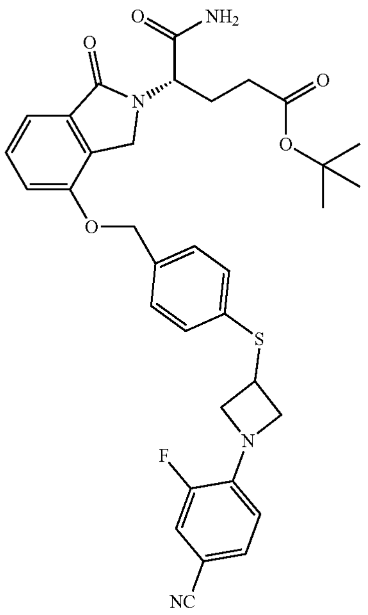 [SMILES: CC(C)(C)OC(=O)CC[C@@H](C(N)=O)N1Cc2c(OCc3ccc(SC4CN(c5ccc(C#N)cc5F)C4)cc3)cccc2C1=O]<br>Tert-butyl (S)-5-amino-4-(4-((4-((1-(4-cyano-2-fluorophenyl)azetidin-3-yl)thio) benzyl)oxy)-1-oxoisoindolin-2-yl)-5-oxopentanoate |
| 17g | 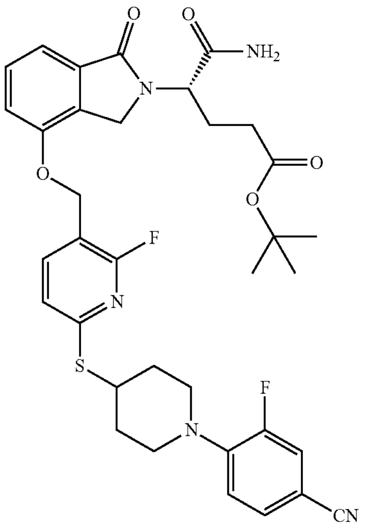 [SMILES: CC(C)(C)OC(=O)CC[C@@H](C(N)=O)N1Cc2c(OCc3ccc(SC4CCN(c5ccc(C#N)cc5F)CC4)nc3F)cccc2C1=O]<br>Tert-butyl (S)-5-amino-4-(4-((6-((1-(4-cyano-2-fluorophenyl)piperidin-4-yl)thio) -2-fluoropyridin-3-yl)methoxy)-1-oxoisoindolin-2-yl)-5-oxopentanoate<br>17g |

-continued

| Example No. | Structure and name of compound |
|---|---|
| | 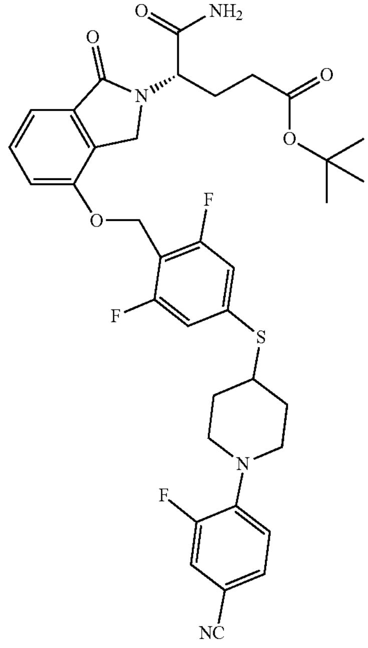 [SMILES: CC(C)(C)OC(=O)CC[C@@H](C(N)=O)N1Cc2c(OCc3c(F)cc(SC4CCN(c5ccc(C#N)cc5F)CC4)cc3F)cccc2C1=O] Tert-butyl (S)-5-amino-4-(4-((4-((1-(4-cyano-2-fluorophenyl)piperidin-4-yl)thio)-2,6-difluorobenzyl)oxy)-1-oxoisoindolin-2-yl)-5-oxopentanoate |

Another aspect of the present disclosure relates to a method for preparing a compound of general formula (I) or a tautomer, mesomer, racemate, enantiomer or diastereomer thereof or a mixture thereof, or a pharmaceutically acceptable salt thereof, which comprises:

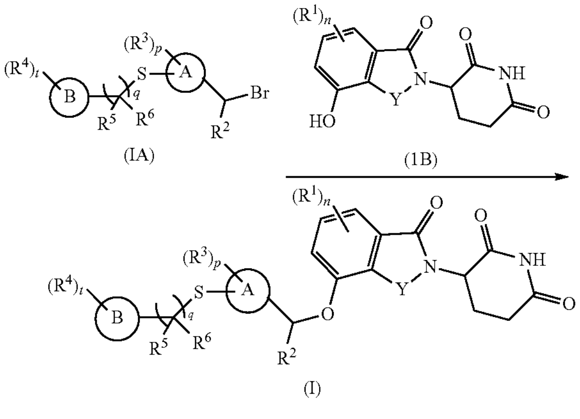

(IA) (1B) (I)

subjecting a compound of general formula (IA) and a compound of general formula (IB) to a reaction to obtain the compound of general formula (I), wherein:

ring A, ring B, Y, $R^1$ to $R^6$, n, p, q and t are as defined in general formula (I).

Another aspect of the present disclosure relates to a method for preparing a compound of general formula (I) or a tautomer, mesomer, racemate, enantiomer or diastereomer thereof or a mixture thereof, or a pharmaceutically acceptable salt thereof, which comprises:

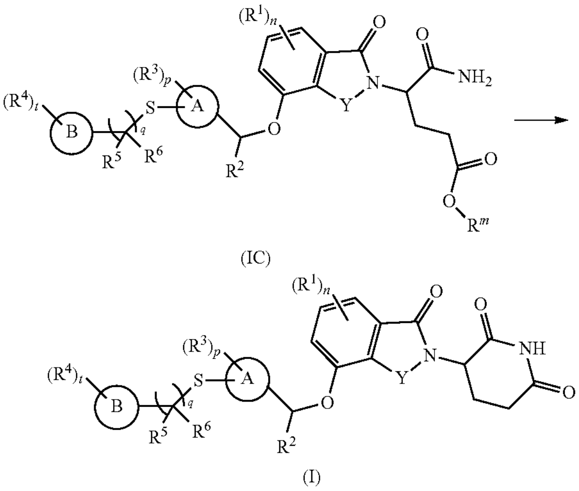

(IC) (I)

subjecting a compound of general formula (IC) to an intramolecular ring closure reaction to obtain the compound of general formula (I), wherein:

$R^m$ is $C_{1-6}$ alkyl; preferably tert-butyl; and ring A, ring B, Y, $R^1$ to $R^6$, n, p, q and t are as defined in general formula (I).

Another aspect of the present disclosure relates to a method for preparing a compound of general formula (I-1) or a tautomer, mesomer, racemate, enantiomer or diastereomer thereof or a mixture thereof, or a pharmaceutically acceptable salt thereof, which comprises:

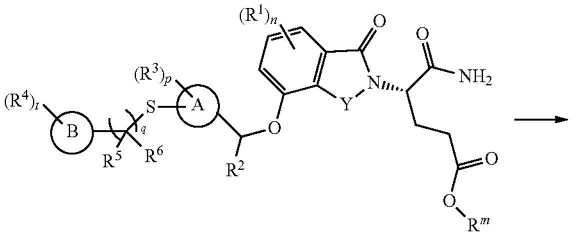

(I-1C)

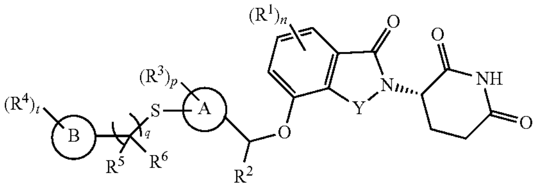

(I-1)

subjecting a compound of general formula (I-1C) to an intramolecular ring closure reaction to obtain the compound of general formula (I-1), wherein:

R''' is $C_{1-6}$ alkyl; preferably tert-butyl; and ring A, ring B, Y, $R^1$ to $R^6$, n, p, q and t are as defined in general formula (I-1).

Another aspect of the present disclosure relates to a method for preparing a compound of general formula (I-2) or a tautomer, mesomer, racemate, enantiomer or diastereomer thereof or a mixture thereof, or a pharmaceutically acceptable salt thereof, which comprises:

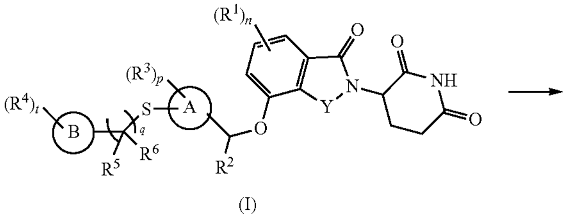

(I)

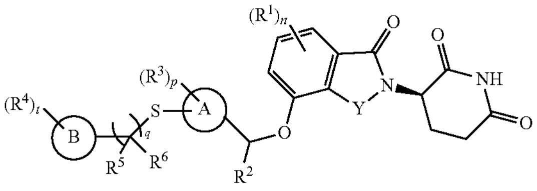

(I-2)

subjecting a compound of general formula (I) or a tautomer, mesomer, racemate, enantiomer or diastereomer thereof or a mixture thereof, or a pharmaceutically acceptable salt thereof to a preparative chiral resolution to obtain the compound of general formula (I-2) or the tautomer, mesomer, racemate, enantiomer or diastereomer thereof or the mixture thereof, or the pharmaceutically acceptable salt thereof, wherein:

R''' is $C_{1-6}$ alkyl; preferably tert-butyl; and ring A, ring B, Y, $R^1$ to $R^6$, n, p, q and t are as defined in general formula (I).

Another aspect of the present disclosure relates to a method for preparing a compound of general formula (II) or a tautomer, mesomer, racemate, enantiomer or diastereomer thereof or a mixture thereof, or a pharmaceutically acceptable salt thereof, which comprises:

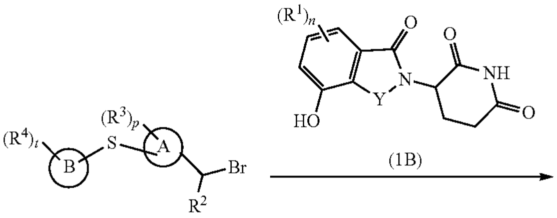

(1B)

(IIA)

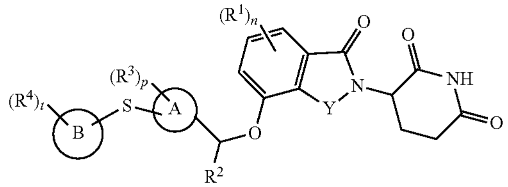

(II)

subjecting a compound of general formula (IIA) and a compound of general formula (IB) to a reaction to obtain the compound of general formula (II), wherein:

ring A, ring B, Y, $R^1$ to $R^4$, n, p and t are as defined in general formula (II).

Another aspect of the present disclosure relates to a method for preparing a compound of general formula (II) or a tautomer, mesomer, racemate, enantiomer or diastereomer thereof or a mixture thereof, or a pharmaceutically acceptable salt thereof, which comprises:

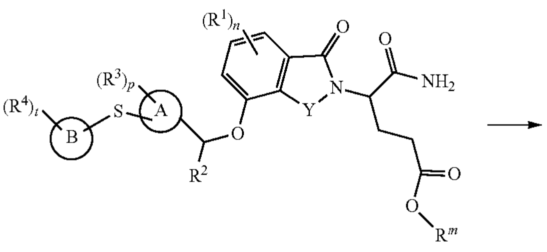

(IIC)

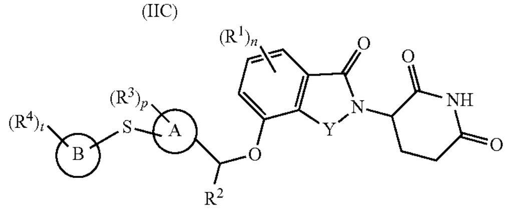

(II)

subjecting a compound of general formula (IIC) to an intramolecular ring closure reaction to obtain the compound of general formula (II), wherein:

R''' is $C_{1-6}$ alkyl; preferably tert-butyl; and ring A, ring B, Y, $R^1$ to $R^4$, n, p and t are as defined in general formula (II).

Another aspect of the present disclosure relates to a method for preparing a compound of general formula (II-1) or a tautomer, mesomer, racemate, enantiomer or diastereomer thereof or a mixture thereof, or a pharmaceutically acceptable salt thereof, which comprises:

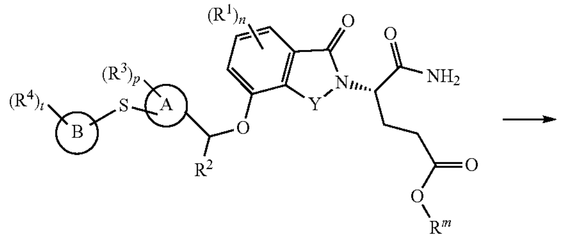

(II-1C)

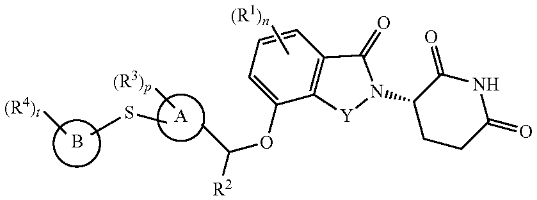

(II-1)

subjecting a compound of general formula (II-1C) to an intramolecular ring closure reaction to obtain the compound of general formula (II-1), wherein:

$R^m$ is $C_{1-6}$ alkyl; preferably tert-butyl; and ring A, ring B, Y, $R^1$ to $R^4$, n, p and t are as defined in general formula (II).

Another aspect of the present disclosure relates to a method for preparing a compound of general formula (II-2) or a tautomer, mesomer, racemate, enantiomer or diastereomer thereof or a mixture thereof, or a pharmaceutically acceptable salt thereof, which comprises:

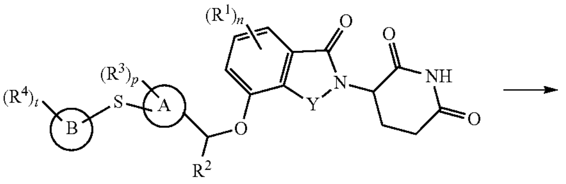

(II)

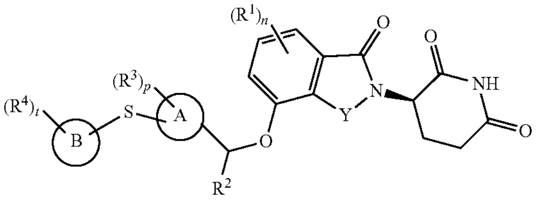

(II-2)

subjecting a compound of general formula (II) or a tautomer, mesomer, racemate, enantiomer or diastereomer thereof or a mixture thereof, or a pharmaceutically acceptable salt thereof to a preparative chiral resolution to obtain the compound of general formula (II-2) or the tautomer, mesomer, racemate, enantiomer or diastereomer thereof or the mixture thereof, or the pharmaceutically acceptable salt thereof, wherein:

$R^m$ is $C_{1-6}$ alkyl; preferably tert-butyl; and ring A, ring B, Y, $R^1$ to $R^4$, n, p and t are as defined in general formula (II).

Another aspect of the present disclosure relates to a method for preparing a compound of general formula (IIG) or a tautomer, mesomer, racemate, enantiomer or diastereomer thereof or a mixture thereof, or a pharmaceutically acceptable salt thereof, which comprises:

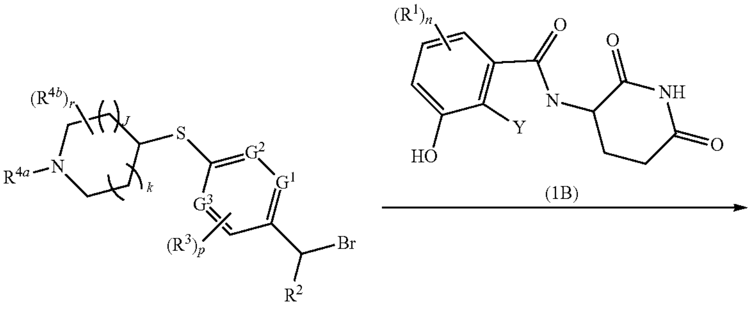

(IIGA)

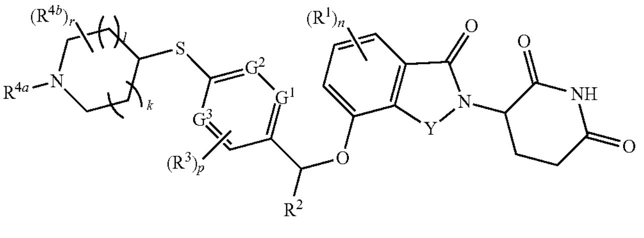

(IIG)

subjecting a compound of general formula (IIGA) and a compound of general formula (IB) to a reaction to obtain the compound of general formula (IIG), wherein:

$G^1$, $G^2$, $G^3$, Y, $R^1$ to $R^3$, $R^{4a}$, $R^{4b}$, J, k, n, p and r are as defined in general formula (IIG).

Another aspect of the present disclosure relates to a method for preparing a compound of general formula (IIG) or a tautomer, mesomer, racemate, enantiomer or diastereomer thereof or a mixture thereof, or a pharmaceutically acceptable salt thereof, which comprises:

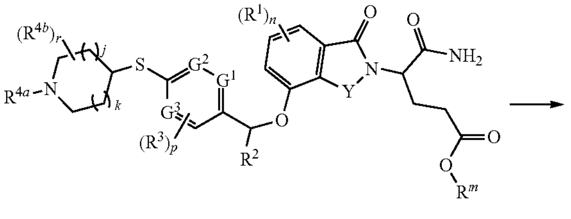

(IIGC)

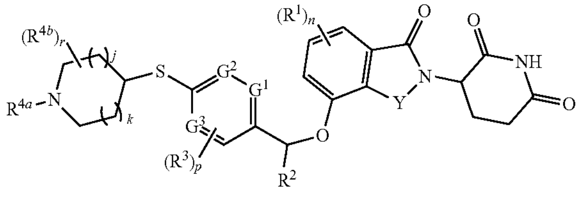

(IIG)

subjecting a compound of general formula (IIGC) to an intramolecular ring closure reaction to obtain the compound of general formula (IIG), wherein:

$R^m$ is $C_{1-6}$ alkyl; preferably tert-butyl; and $G^1$, $G^2$, $G^3$, Y, $R^1$ to $R^3$, $R^{4a}$, $R^{4b}$, J, k, n, p and r are as defined in general formula (IIG).

Another aspect of the present disclosure relates to a method for preparing a compound of general formula (IIG-1) or a tautomer, mesomer, racemate, enantiomer or diastereomer thereof or a mixture thereof, or a pharmaceutically acceptable salt thereof, which comprises:

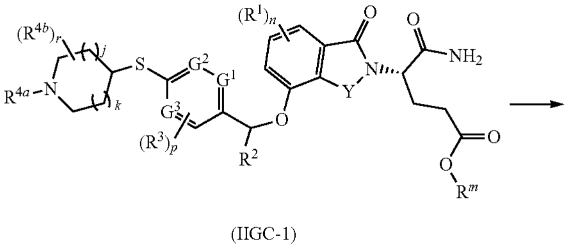

(IIGC-1)

-continued

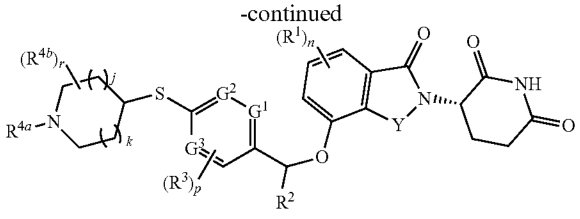

(IIG-1)

subjecting a compound of general formula (IIGC-1) to an intramolecular ring closure reaction to obtain the compound of general formula (IIG-1), wherein:

$R^m$ is $C_{1-6}$ alkyl; preferably tert-butyl; and $G^1$, $G^2$, $G^3$, Y, $R^1$ to $R^3$, $R^{4a}$, $R^{4b}$, J, k, n, p and r are as defined in general formula (IIG-1).

Another aspect of the present disclosure relates to a method for preparing a compound of general formula (IIG-2) or a tautomer, mesomer, racemate, enantiomer or diastereomer thereof or a mixture thereof, or a pharmaceutically acceptable salt thereof, which comprises:

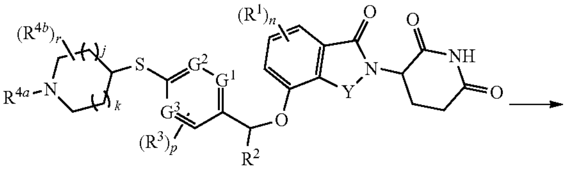

(IIG)

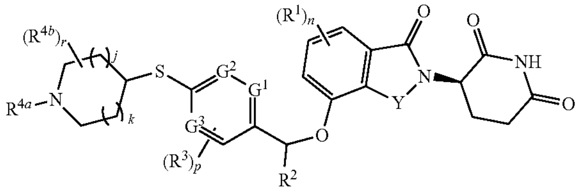

(IIG-2)

subjecting a compound of general formula (IIG) or a tautomer, mesomer, racemate, enantiomer or diastereomer thereof or a mixture thereof, or a pharmaceutically acceptable salt thereof to a preparative chiral resolution to obtain the compound of general formula (IIG-2) or the tautomer, mesomer, racemate, enantiomer or diastereomer thereof or the mixture thereof, or the pharmaceutically acceptable salt thereof, wherein:

$R^m$ is $C_{1-6}$ alkyl; preferably tert-butyl; and $G^1$, $G^2$, $G^3$, Y, $R^1$ to $R^3$, $R^{4a}$, $R^{4b}$, J, k, n, p and r are as defined in general formula (IIG).

Another aspect of the present disclosure relates to a method for preparing a compound of general formula (III) or a tautomer, mesomer, racemate, enantiomer or diastereomer thereof or a mixture thereof, or a pharmaceutically acceptable salt thereof, which comprises:

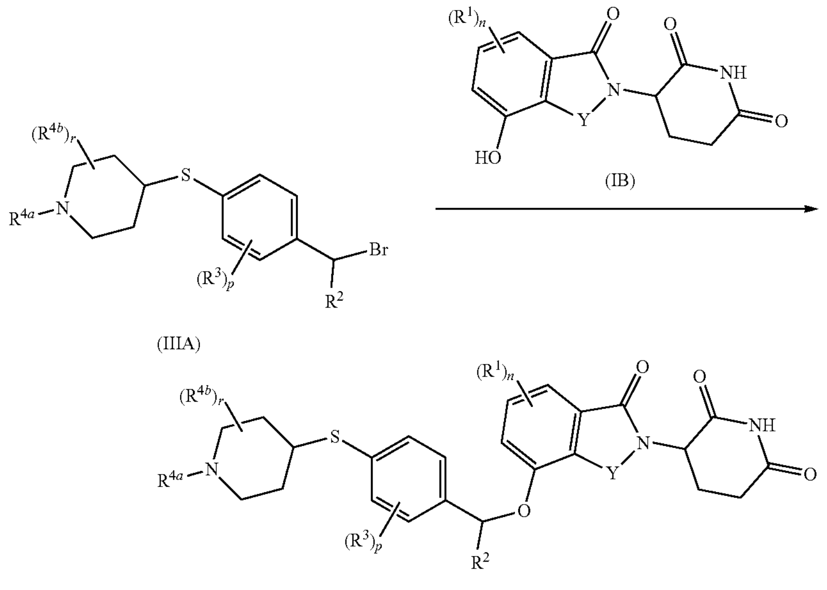

(IB)

(IIIA)

(III)

subjecting a compound of general formula (IIIA) and a compound of general formula (IB) to a reaction to obtain the compound of general formula (III), wherein:

Y, $R^1$ to $R^3$, $R^{4a}$, $R^{4b}$, n, p and r are as defined in general formula (III).

Another aspect of the present disclosure relates to a method for preparing a compound of general formula (III) or a tautomer, mesomer, racemate, enantiomer or diastereomer thereof or a mixture thereof, or a pharmaceutically acceptable salt thereof, which comprises:

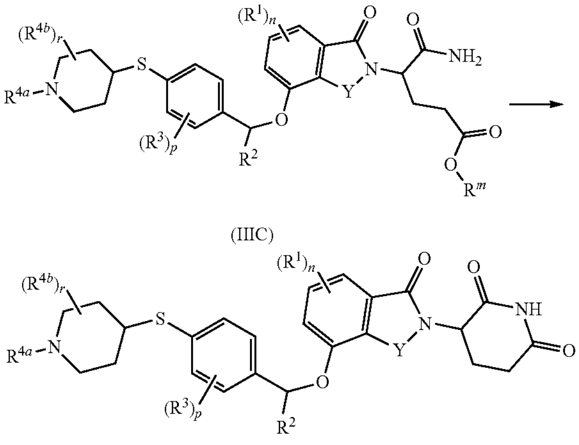

(IIIC)

(III)

subjecting a compound of general formula (IIIC) to an intramolecular ring closure reaction to obtain the compound of general formula (III), wherein:

$R^m$ is $C_{1-6}$ alkyl; preferably tert-butyl; and

Y, $R^1$ to $R^3$, $R^{4a}$, $R^{4b}$, n, p and r are as defined in general formula (III).

Another aspect of the present disclosure relates to a method for preparing a compound of general formula (III-1) or a tautomer, mesomer, racemate, enantiomer or diastereomer thereof or a mixture thereof, or a pharmaceutically acceptable salt thereof, which comprises:

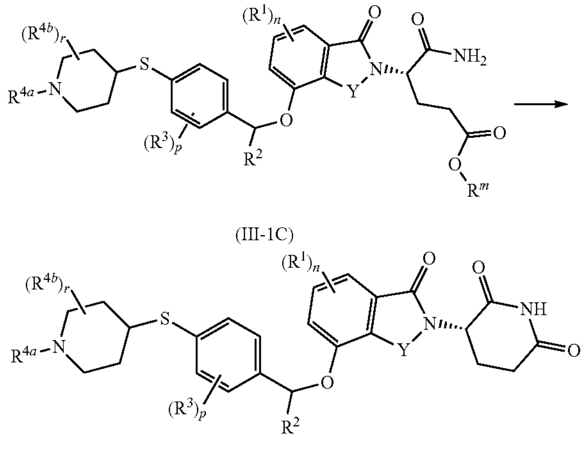

(III-1C)

(III-1)

subjecting a compound of general formula (III-1C) to an intramolecular ring closure reaction to obtain the compound of general formula (III-1), wherein:

$R^m$ is $C_{1-6}$ alkyl; preferably tert-butyl; and

Y, $R^1$ to $R^3$, $R^{4a}$, $R^{4b}$, n, p and r are as defined in general formula (III-1).

Another aspect of the present disclosure relates to a method for preparing a compound of general formula (III-2) or a tautomer, mesomer, racemate, enantiomer or diastereomer thereof or a mixture thereof, or a pharmaceutically acceptable salt thereof, which comprises:

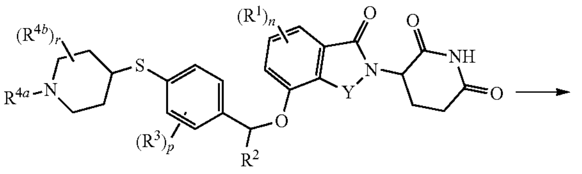

(III)

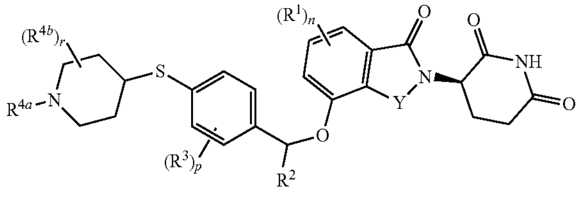

(III-2)

subjecting a compound of general formula (III) or a tautomer, mesomer, racemate, enantiomer or diastereomer thereof or a mixture thereof, or a pharmaceutically acceptable salt thereof to a preparative chiral resolution to obtain the compound of general formula (III-2) or the tautomer, mesomer, racemate, enantiomer or diastereomer thereof or the mixture thereof, or the pharmaceutically acceptable salt thereof, wherein:

$R^m$ is $C_{1-6}$ alkyl; preferably tert-butyl; and

Y, $R^1$ to $R^3$, $R^{4a}$, $R^{4b}$, n, p and r are as defined in general formula (III).

Another aspect of the present disclosure relates to a pharmaceutical composition comprising the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) of the present disclosure or the compound shown in Table A, or the tautomer, mesomer, racemate, enantiomer or diastereomer thereof or the mixture thereof, or the pharmaceutically acceptable salt thereof, and one or more pharmaceutically acceptable carriers, diluents or excipients.

The present disclosure further relates to use of the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) of the present disclosure or the compound shown in Table A, or the tautomer, mesomer, racemate, enantiomer or diastereomer thereof or the mixture thereof, or the pharmaceutically acceptable salt thereof, or the pharmaceutical composition comprising the same in preparing a medicament for the treatment and/or prevention of a CRBN protein-related disease.

The present disclosure further relates to use of the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or the compound shown in Table A, or the tautomer, mesomer, racemate, enantiomer or diastereomer thereof or the mixture thereof, or the pharmaceutically acceptable salt thereof, or the pharmaceutical composition comprising the same in preparing a medicament for the treatment and/or prevention of a cancer, an angiogenesis-related disorder, pain, macular degeneration or related syndromes, a skin disease, a pulmonary disease, an asbestos-related disease, a parasitic disease, an immunodeficiency disease, a CNS disease, a CNS injury, atherosclerosis or related disorders, sleep disorder or related disorders, an infectious disease, hemoglobinopathy or related disorders, or a TNFα-related disorder; preferably, in preparing a medicament for the treatment and/or prevention of a cancer or a CNS injury.

The present disclosure further relates to a method for treating and/or preventing a CRBN protein-related disease, which comprises administering to a patient in need thereof a therapeutically effective amount of the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or the compound shown in Table A, or the tautomer, mesomer, racemate, enantiomer or diastereomer thereof or the mixture thereof, or the pharmaceutically acceptable salt thereof, or the pharmaceutical composition comprising the same.

The present disclosure further relates to a method for treating and/or preventing a cancer, an angiogenesis-related disorder, pain, macular degeneration or related syndromes, a skin disease, a pulmonary disease, an asbestos-related disease, a parasitic disease, an immunodeficiency disease, a CNS disease, a CNS injury, atherosclerosis or related disorders, sleep disorder or related disorders, an infectious disease, hemoglobinopathy or related disorders, or a TNFα-related disorder, preferably a method for treating and/or preventing a cancer or a CNS injury, which comprises administering to a patient in need thereof a therapeutically effective amount of the compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or the compound shown in Table A, or the tautomer, mesomer, racemate, enantiomer or diastereomer thereof or the mixture thereof, or the pharmaceutically acceptable salt thereof, or the pharmaceutical composition comprising the same.

The present disclosure further relates to a compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or a compound shown in Table A, or a tautomer, mesomer, racemate, enantiomer or diastereomer thereof or a mixture thereof, or a pharmaceutically acceptable salt thereof, or a pharmaceutical composition comprising the same, for use as a medicament.

The present disclosure further relates to a compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or a compound shown in Table A, or a tautomer, mesomer, racemate, enantiomer or diastereomer thereof or a mixture thereof, or a pharmaceutically acceptable salt thereof, or the pharmaceutical composition comprising the same, for use in treating and/or preventing a CRBN protein-related disease.

The CRBN protein-related disease described herein is selected from the group consisting of a cancer, an angiogenesis-related disorder, pain, macular degeneration or related syndromes, a skin disease, a pulmonary disease, an asbestos-related disease, a parasitic disease, an immunodeficiency disease, a CNS disease, a CNS injury, atherosclerosis or related disorders, sleep disorder or related disorders, an infectious disease, hemoglobinopathy or related disorders, and a TNFα-related disorder; preferably a cancer or a CNS injury.

The present disclosure further relates to a compound of general formula (I), general formula (I-1), general formula (I-2), general formula (II), general formula (II-1), general formula (II-2), general formula (IIG), general formula (IIG-1), general formula (IIG-2), general formula (III), general formula (III-1) or general formula (III-2) or a compound shown in Table A, or a tautomer, mesomer, racemate, enantiomer or diastereomer thereof or a mixture thereof, or a pharmaceutically acceptable salt thereof, or a pharmaceutical composition comprising the same, for use in treating and/or preventing a cancer, an angiogenesis-related disorder, pain, macular degeneration or related syndromes, a skin disease, a pulmonary disease, an asbestos-related disease, a parasitic disease, an immunodeficiency disease, a CNS disease, a CNS injury, atherosclerosis or related disorders, sleep disorder or related disorders, an infectious disease, hemoglobinopathy or related disorders, or a TNFα-related disorder; preferably, for use in treating and/or preventing a cancer or a CNS injury.

The cancer described herein is selected from the group consisting of leukemia, myeloma, lymphoma, melanoma, skin cancer, liver cancer, kidney cancer, lung cancer, nasopharyngeal cancer, gastric cancer, esophageal cancer, colorectal cancer, gallbladder cancer, bile duct cancer, chorionic epithelioma, pancreatic cancer, polycythemia vera, pediatric tumor, cervical cancer, ovarian cancer, breast cancer, bladder cancer, urothelial cancer, ureteral tumor, prostate cancer, seminoma, testicular tumor, head and neck tumor, head and neck squamous cell carcinoma, endometrial cancer, thyroid cancer, sarcoma, osteoma, neuroblastoma, neuroendocrine cancer, brain tumor, CNS cancer, astrocytoma, and glioma; preferably, the liver cancer is hepatocellular carcinoma; the colorectal cancer is colon cancer or rectal cancer; the sarcoma is osteosarcoma or soft tissue sarcoma; and the glioma is glioblastoma. The leukemia is preferably chronic lymphocytic leukemia, acute lymphocytic leukemia (ALL), acute myeloid leukemia (AML), chronic myeloid leukemia (CML) or hairy cell leukemia; the lymphoma is preferably small lymphocytic lymphoma, marginal zone lymphoma, follicular lymphoma, mantle cell lymphoma, non-Hodgkin's lymphoma (NHL), lymphoplasmacytic lymphoma, extranodal marginal zone lymphoma, T-cell lymphoma, B-cell lymphoma or diffuse large B-cell lymphoma; and the myeloma is preferably multiple myeloma (MM) or myelodysplastic syndrome (MDS). The cancer described herein includes primary cancer or metastatic cancer. The cancer described herein also includes those that are refractory or resistant to chemotherapy or radiotherapy. More preferably, the multiple myeloma is relapsed, refractory or resistant. Most preferably, the multiple myeloma is refractory or resistant to lenalidomide or pomalidomide.

Examples of the CNS disease include, but are not limited to, the diseases described in U.S. publication No. US2005/0143344A1 disclosed on Jun. 30, 2005, the contents of which are incorporated herein by reference. Specific examples include, but are not limited to, amyotrophic lateral sclerosis, Alzheimer's disease, Parkinson's disease, Huntington's disease, multiple sclerosis, and other neuroimmune disorders such as Tourette syndrome, delusions, or disturbances of consciousness or amnesia that occur within a very short period of time, or scattered memory impairment that occurs when other central nervous system impairments are not present.

Examples of the CNS injury and related syndromes include, but are not limited to, the diseases described in U.S. publication No. US2006/0122228A1 disclosed on Jun. 8, 2006, the contents of which are incorporated herein by reference. Specific examples include, but are not limited to, primary brain injury, secondary brain injury, traumatic brain injury, focal brain injury, diffuse axonal injury, craniocerebral injury, concussion, post-concussion syndrome, contusion and laceration of the brain, subdural hematoma, epidermal hematoma, post-traumatic epilepsy, chronic vegetative state, complete SCI, incomplete SCI, acute SCI, subacute SCI, chronic SCI, central cord syndrome, brown-sequard syndrome, anterior cord syndrome, conus medullaris syndrome, cauda equina syndrome, neurogenic shock, spinal shock, altered level of consciousness, headache, nausea, vomit, hypomnesis, dizziness, diplopia, blurred vision, mood swings, sleep disorder, irritability, inability to concentrate, nervousness, behavior disorder, cognitive deficit, and epilepsy.

The angiogenesis-related disease includes, but is not limited to, an inflammatory diseases, an autoimmune disease, a viral disease, a genetic disease, an allergic disease, a bacterial disease, an ocular neovascular disease, a choroidal neovascular disease, a retina neovascular disease, and rubeosis iridis (angle neovascularization). Preferably, the angiogenesis-related disease includes, but is not limited to, arthritis, endometriosis, Crohn's disease, heart failure, severe heart failure, renal injury, endotoxemia, toxic shock syndrome, osteoarthritis, retroviral replication, wasting disease, meningitis, silica-induced fibrosis, asbestos-induced fibrosis, veterinary disease, malignancy-associated hypercalcemia, stroke, circulatory shock, periodontitis, gingivitis, megaloblastic anemia, refractory anemia, and 5q deletion syndrome.

The active compound may be formulated into a form suitable for administration by any suitable route, and one or more pharmaceutically acceptable carriers are used to formulate the composition of the present disclosure by conventional methods. Thus, the active compound of the present disclosure may be formulated into a variety of dosage forms for oral administration, administration by injection (e.g., intravenous, intramuscular or subcutaneous), or administration by inhalation or insufflation. The compound of the present disclosure may also be formulated into a dosage form, such as tablets, hard or soft capsules, aqueous or oily suspensions, emulsions, injections, dispersible powders or granules, suppositories, lozenges or syrups.

As a general guide, the active compound is preferably in a form of a unit dose, or in a form of a single dose that can be self-administered by a patient. The unit dose of the compound or composition of the present disclosure may be in a tablet, capsule, cachet, vial, powder, granule, lozenge, suppository, regenerating powder or liquid formulation. A suitable unit dose may be 0.1-1000 mg.

The pharmaceutical composition of the present disclosure may comprise, in addition to the active compound, one or more auxiliary materials selected from the group consisting of a filler (diluent), a binder, a wetting agent, a disintegrant, an excipient, and the like. Depending on the mode of administration, the composition may comprise 0.1 wt. % to 99 wt. % of the active compound.

The tablet comprises the active ingredient and a non-toxic pharmaceutically acceptable excipient that is used for mixing and is suitable for the preparation of the tablet. Such an excipient may be an inert excipient, a granulating agent, a disintegrant, a binder and a lubricant. Such a tablet may be uncoated or may be coated by known techniques for masking the taste of the drug or delaying the disintegration and absorption of the drug in the gastrointestinal tract and thus enabling sustained release of the drug over a longer period.

An oral formulation in a soft gelatin capsule where the active ingredient is mixed with an inert solid diluent or with a water-soluble carrier or oil vehicle may also be provided.

An aqueous suspension comprises the active substance and an excipient that is used for mixing and is suitable for the preparation of the aqueous suspension. Such an excipient is a suspending agent, a dispersant or a wetting agent. The aqueous suspension may also comprise one or more preservatives, one or more colorants, one or more corrigents and one or more sweeteners.

An oil suspension may be formulated by suspending the active ingredient in a vegetable oil, or in a mineral oil. The oil suspension may comprise a thickening agent. The sweeteners and corrigents described above may be added to provide a palatable formulation. Antioxidants may also be added for the preservation of the compositions.

The pharmaceutical composition of the present disclosure may also be in the form of an oil-in-water emulsion. The oil phase may be a vegetable oil or a mineral oil, or a mixture thereof. Suitable emulsifiers may be naturally occurring phospholipids, and the emulsion may also comprise a sweetener, a corrigent, a preservative and an antioxidant. Such a formulation may also comprise a palliative, a preservative, a colorant and an antioxidant.

The pharmaceutical composition of the present disclosure may be in the form of a sterile injectable aqueous solution. Available and acceptable vehicles or solvents include water, Ringer's solution and isotonic sodium chloride solution. A sterile injectable formulation may be a sterile injectable oil-in-water microemulsion in which an active ingredient is dissolved in an oil phase. The injection or microemulsion can be locally injected into the bloodstream of a patient in large quantities. Alternatively, it may be desirable to administer the solution and microemulsion in such a way as to maintain a constant circulating concentration of the compound of the present disclosure. To maintain such a constant concentration, a continuous intravenous delivery device may be used. An example of such a device is a Deltec CADD-PLUS.™ 5400 intravenous injection pump.

The pharmaceutical composition of the present disclosure may be in the form of a sterile injectable aqueous or oil suspension for intramuscular and subcutaneous administration. The suspension may be prepared according to the prior art using those suitable dispersants or wetting agents and suspending agents as described above. The sterile injectable formulation may also be a sterile injection or suspension prepared in a parenterally acceptable non-toxic diluent or solvent. In addition, a sterile fixed oil may be conveniently used as a solvent or a suspending medium. For this purpose, any blend fixed oil may be used. In addition, fatty acids may also be used to prepare injections.

The compound of the present disclosure may be administered in the form of a suppository for rectal administration. Such a pharmaceutical composition can be prepared by mixing a drug with a suitable non-irritating excipient which is a solid at ambient temperature but a liquid in the rectum and therefore will melt in the rectum to release the drug.

The compound of the present disclosure may be administered in the form of dispersible powders and granules that are formulated into aqueous suspensions by adding water. Such a pharmaceutical composition can be prepared by mixing the active ingredient with a dispersant or a wetting agent, a suspending agent, or one or more preservatives.

As is well known to those skilled in the art, the dose of the drug administered depends on a variety of factors, including but not limited to, the activity of the particular compound used, the age of the patient, the body weight of the patient, the health condition of the patient, the behavior of the patient, the diet of the patient, the time of administration, the route of administration, the rate of excretion, the combination of drugs, the severity of the disease, and the like. In addition, the optimal treatment regimen, such as the mode of administration, the daily dose of the compound or the type of pharmaceutically acceptable salts, can be verified according to conventional treatment regimens.

Description of the Terms

Unless otherwise stated, the terms used in the specification and claims have the following meanings.

The term "alkyl" refers to a saturated aliphatic hydrocarbon group which is a linear or branched group containing 1 to 20 carbon atoms, preferably alkyl containing 1 to 12 (e.g., 1, 2, 3, 4, 5, 6, 7, 8, 9, 10, 11 and 12) carbon atoms, and more preferably alkyl containing 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methyl propyl, 1,1,2-trimethyl propyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof, and the like. More preferred is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methyl propyl, 1,1,2-tri methyl propyl, 1,1-dimethylbutyl, methylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted. When substituted, it may be substituted at any accessible connection site, wherein the substituent is preferably one or more substituents independently and optionally selected from the group consisting of a D atom, halogen, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkylene" refers to a saturated linear or branched aliphatic hydrocarbon group, which is a residue derived by removal of two hydrogen atoms from the same carbon atom or two different carbon atoms of the parent alkane. It is a linear or branched group containing 1 to 20 carbon atoms, preferably alkylene containing 1 to 12 (e.g., 1, 2, 3, 4, 5, 6, 7, 8, 9, 10, 11 and 12) carbon atoms, and more preferably alkylene containing 1 to 6 carbon atoms. Non-limiting examples of alkylene include, but are not limited to, methylene ($—CH_2—$), 1,1-ethylene ($—CH(CH_3)—$), 1,2-ethylene ($—CH_2CH_2—$), 1,1-propylene ($—CH(CH_2CH_3)—$), 1,2-propylene ($—CH_2CH(CH_3)—$), 1,3-propylene ($—CH_2CH_2CH_2—$), 1,4-butylene ($—CH_2CH_2CH_2CH_2—$), and the like. The alkylene may be substituted or unsubstituted. When substituted, it may be substituted at any accessible connection site, wherein the substituent is preferably one or more substituents independently and optionally selected from the group consisting of alkenyl, alkynyl, alkoxy, haloalkoxy, cycloalkyloxy, heterocyclyloxy, alkylthio, alkylamino, halogen, mercapto, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkenyl" refers to an alkyl compound containing at least one carbon-carbon double bond in the molecule, wherein the alkyl is as defined above. The alkenyl may be substituted or unsubstituted. When substituted, the substituent is preferably one or more groups independently selected from the group consisting of alkoxy, halogen, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkynyl" refers to an alkyl compound containing at least one carbon-carbon triple bond in the molecule, wherein the alkyl is as defined above. The alkynyl may be substituted or unsubstituted. When substituted, the substituent is preferably one or more groups independently selected from the group consisting of alkyl, alkoxy, halogen, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms (either a specific point or an interval of any two points, e.g., 3, 4, 5, 6, 7, 8, 9, 10, 11 and 12 ring atoms, 4 to 11 ring atoms, 6 to 12 ring atoms, etc.), preferably 3 to 8 (e.g., 3, 4, 5, 6, 7 and 8) carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term "spiro cycloalkyl" refers to a 5- to 20-membered polycyclic group in which monocyclic rings share one carbon atom (referred to as the spiro atom), which may contain one or more double bonds. The spiro cycloalkyl is preferably 6- to 14-membered, and more preferably 7- to 10-membered (e.g., 7-membered, 8-membered, 9-membered or 10-membered). According to the number of the Spiro atoms shared among the rings, the Spiro cycloalkyl may be monospiro cycloalkyl, bispiro cycloalkyl or polyspiro cycloalkyl, preferably monospiro cycloalkyl and bispiro cycloalkyl, and more preferably 3-membered/5-membered, 3-membered/6-membered, 4-membered/4-membered, 4-membered/5-membered, 4-membered/6-membered, 5-membered/5-membered or 5-membered/6-membered monospiro cycloalkyl. Non-limiting examples of Spiro cycloalkyl include:

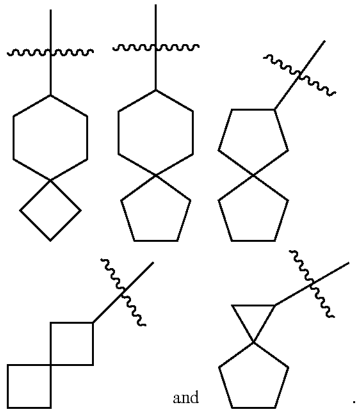

and

The term "fused cycloalkyl" refers to a 5- to 20-membered carbon polycyclic group in which each ring shares a pair of adjacent carbon atoms with the other rings in the system, wherein one or more of the rings may contain one or more double bonds. The fused cycloalkyl is preferably 6- to 14-membered, and more preferably 7- to 10-membered (e.g., 7-membered, 8-membered, 9-membered or 10-membered). According to the number of the formed rings, the fused cycloalkyl may be bicyclic, tricyclic, tetracyclic or polycyclic cycloalkyl, preferably bicyclic or tricyclic cycloalkyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic cycloalkyl. Non-limiting examples of fused cycloalkyl include:

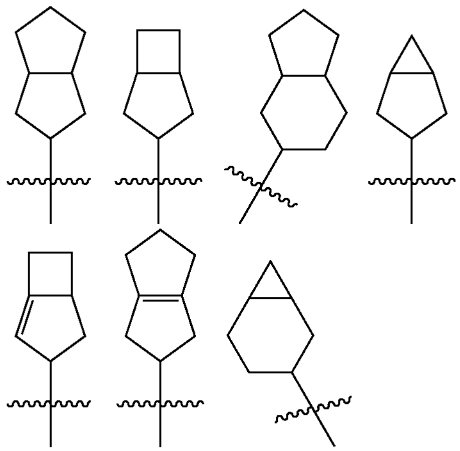

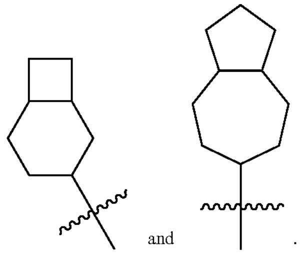

and

The term "bridged cycloalkyl" refers to a 5- to 20-membered carbon polycyclic group in which any two rings share two carbon atoms that are not directly connected to each other, which may contain one or more double bonds. The bridged cycloalkyl is preferably 6- to 14-membered, and more preferably 7- to 10-membered (e.g., 7-membered, 8-membered, 9-membered or 10-membered). According to the number of the formed rings, the bridged cycloalkyl may be bicyclic, tricyclic, tetracyclic or polycyclic, preferably bicyclic, tricyclic or tetracyclic, and more preferably bicyclic or tricyclic. Non-limiting examples of bridged cycloalkyl include:

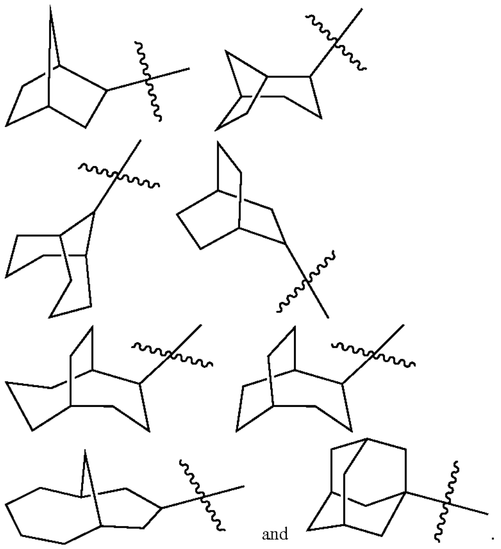

and .

The cycloalkyl ring includes those in which the cycloalkyl described above (including monocyclic, spiro, fused and bridged rings) is fused to an aryl, heteroaryl or heterocycloalkyl ring, wherein the ring connected to the parent structure is cycloalkyl. Non-limiting examples include

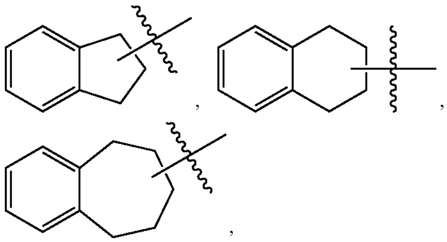

, , , and the like, and preferably

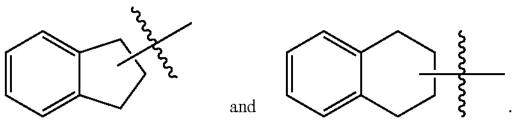

and .

The cycloalkyl may be substituted or unsubstituted. When substituted, it may be substituted at any accessible connection site, wherein the substituent is preferably one or more substituents independently and optionally selected from the group consisting of a hydrogen atom, halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkoxy" refers to —O-(alkyl), wherein the alkyl is as defined above. Non-limiting examples of alkoxy include methoxy, ethoxy, propoxy and butoxy. The alkoxy may be optionally substituted or unsubstituted. When substituted, the substituent is preferably one or more groups independently selected from the group consisting of a D atom, halogen, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "heterocyclyl" refers to a saturated or partially unsaturated monocyclic or polycyclic substituent containing 3 to 20 ring atoms, wherein one or more of the ring atoms is a heteroatom selected from the group consisting of nitrogen, oxygen and sulfur, the sulfur optionally being oxo (i.e., forming sulfoxide or sulfone), but excluding a cyclic portion of —O—O—, —O—S— or —S—S—; and the remaining ring atoms are carbon. The heterocyclyl preferably contains 3 to 12 ring atoms, of which 1 to 4 (e.g., 1, 2, 3 and 4) are heteroatoms; more preferably 3 to 8 (e.g., 3, 4, 5, 6, 7 and 8) ring atoms, of which 1 to 3 (e.g., 1, 2 and 3) are heteroatoms; more preferably 3 to 6 ring atoms, of which 1 to 3 are heteroatoms; and most preferably 5 or 6 ring atoms, of which 1 to 3 are heteroatoms. Non-limiting examples of monocyclic heterocyclyl include oxetanyl, pyrrolidinyl, tetrahydropyranyl, 1,2,3,6-tetrahydropyridinyl, piperidinyl, piperazinyl, morpholinyl, thiomorpholinyl, homopiperazinyl, and the like. Polycyclic heterocyclyl includes spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more of the ring atoms is a heteroatom selected from the group consisting of nitrogen, oxygen and sulfur, the sulfur optionally being oxo (i.e., forming sulfoxide or sulfone); and the remaining ring atoms are carbon. The group may contain one or more double bonds. The spiro cycloalkyl is preferably 6- to 14-membered, and more preferably 7- to 10-membered (e.g., 7-membered, 8-membered, 9-membered or 10-membered). According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 3-membered/5-membered, 3-membered/6-membered, 4-membered/4-membered, 4-membered/5-membered, 4-membered/6-membered, 5-membered/5-membered or 5-membered/6-membered monospiro heterocyclyl. Non-limiting examples of spiro heterocyclyl include:

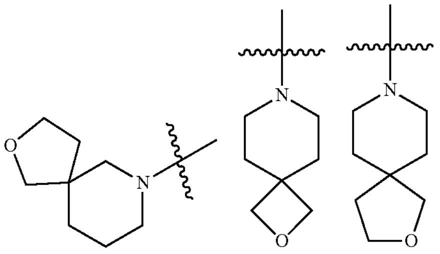

-continued

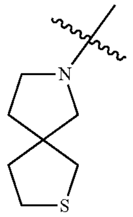
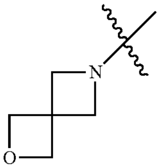
and
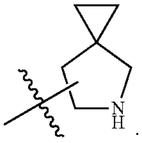
.

The term “fused heterocyclyl” refers to a 5- to 20-membered polycyclic heterocyclyl group in which each ring shares a pair of adjacent atoms with the other rings in the system and one or more of the rings may contain one or more double bonds, wherein one or more of the ring atoms is a heteroatom selected from the group consisting of nitrogen, oxygen and sulfur, the sulfur optionally being oxo (i.e., forming sulfoxide or sulfone); and the remaining ring atoms are carbon. The fused heterocyclyl is preferably 6- to 14-membered, and more preferably 7- to 10-membered (e.g., 7-membered, 8-membered, 9-membered or 10-membered). According to the number of the formed rings, the fused heterocyclyl may be bicyclic, tricyclic, tetracyclic or polycyclic fused heterocyclyl, preferably bicyclic or tricyclic fused heterocyclyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic fused heterocyclyl. Non-limiting examples of fused heterocyclyl include:

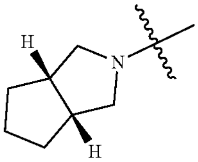
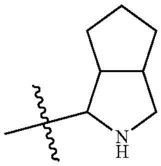
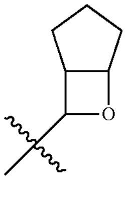
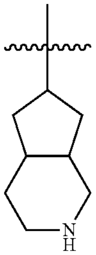
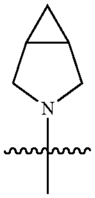
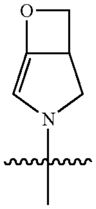
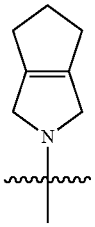
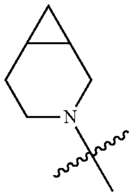
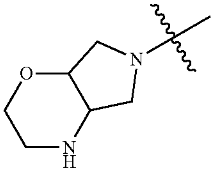
, -continued

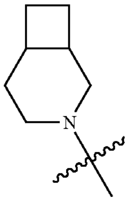
,
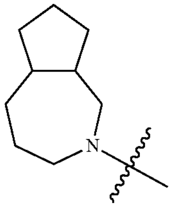
,
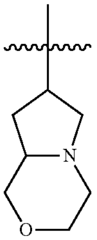
,
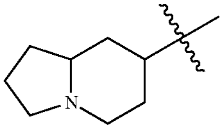
and
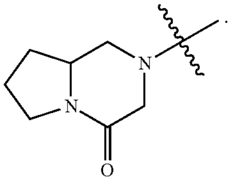
.

The term “bridged heterocyclyl” refers to a 5- to 14-membered polycyclic heterocyclyl group in which any two rings share two atoms which are not directly connected, which may contain one or more double bonds, wherein one or more of the ring atoms is a heteroatom selected from the group consisting of nitrogen, oxygen and sulfur, the sulfur optionally being oxo (i.e., forming sulfoxide or sulfone); and the remaining ring atoms are carbon. The bridged heterocyclyl is preferably 6- to 14-membered, and more preferably 7- to 10-membered (e.g., 7-membered, 8-membered, 9-membered or 10-membered). According to the number of the formed rings, the bridged heterocyclyl may be bicyclic, tricyclic, tetracyclic or polycyclic, preferably bicyclic, tricyclic or tetracyclic, and more preferably bicyclic or tricyclic. Non-limiting examples of bridged heterocyclyl include:

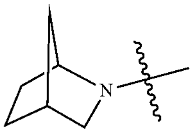
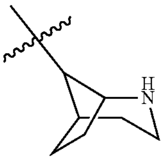
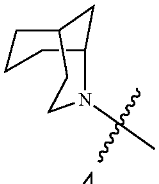
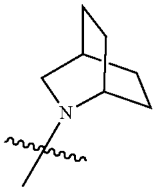
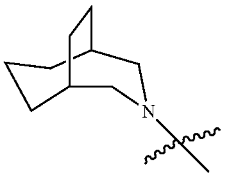
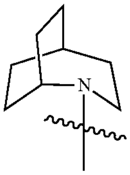
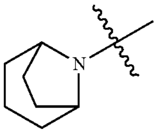
and
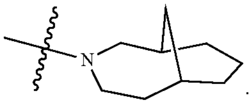
.

The heterocyclyl ring includes those in which the heterocyclyl described above (including monocyclic, spiro heterocyclic, fused heterocyclic and bridged heterocyclic rings) is fused to an aryl, heteroaryl or cycloalkyl ring, wherein the ring connected to the parent structure is heterocyclyl. Non-limiting examples include:

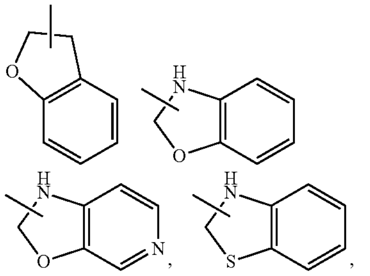

etc.

The heterocyclyl may be substituted or unsubstituted. When substituted, it may be substituted at any accessible connection site, wherein the substituent is preferably one or more substituents independently and optionally selected from the group consisting of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "aryl" refers to a 6- to 14-membered, preferably 6- to 10-membered carbon monocyclic or fused polycyclic (in which the rings share a pair of adjacent carbon atoms) group having a conjugated π-electron system, such as phenyl and naphthyl. The aryl ring includes those in which the aryl ring described above is fused to a heteroaryl, heterocyclyl or cycloalkyl ring, wherein the ring connected to the parent structure is an aryl ring. Non-limiting examples include:

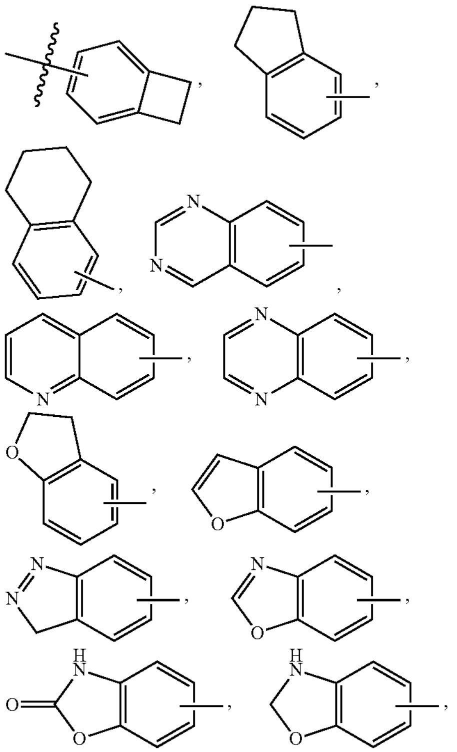

-continued

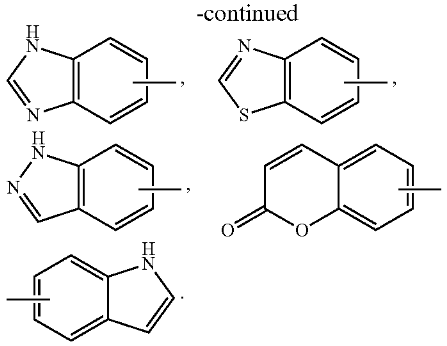

and

The aryl may be substituted or unsubstituted. When substituted, it may be substituted at any accessible connection site, wherein the substituent is preferably one or more substituents independently and optionally selected from the group consisting of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "heteroaryl" refers to a heteroaromatic system containing 1 to 4 (e.g., 1, 2, 3 and 4) heteroatoms and 5 to 14 ring atoms, wherein the heteroatoms are selected from the group consisting of oxygen, sulfur and nitrogen. The heteroaryl is preferably 5- to 10-membered (e.g., 5-membered, 6-membered, 7-membered, 8-membered, 9-membered or 10-membered) and more preferably 5-membered or 6-membered, e.g., furyl, thienyl, pyridinyl, pyrrolyl, N-alkylpyrrolyl, pyrimidinyl, pyrazinyl, pyridazinyl, imidazolyl, pyrazolyl, triazolyl and tetrazolyl. The heteroaryl ring includes those in which the heteroaryl ring described above is fused to an aryl, heterocyclyl or cycloalkyl ring, wherein the ring connected to the parent structure is a heteroaryl ring. Non-limiting examples include:

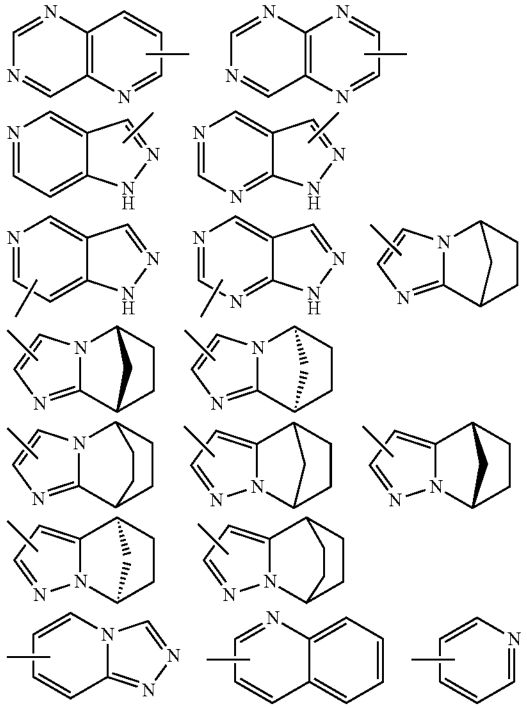

-continued

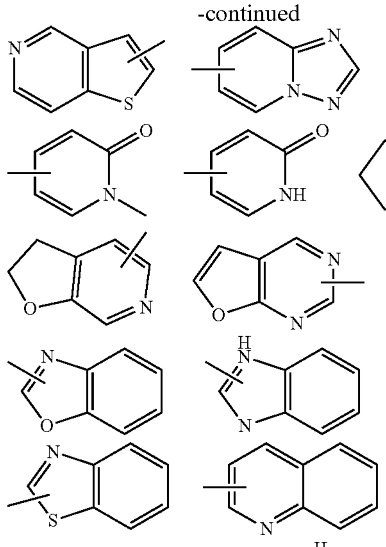

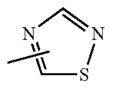 and 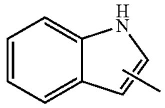.

The heteroaryl may be substituted or unsubstituted. When substituted, it may be substituted at any accessible connection site, wherein the substituent is preferably one or more substituents independently and optionally selected from the group consisting of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The cycloalkyl, heterocyclyl, aryl and heteroaryl described above include residues derived by removal of one hydrogen atom from a carbon atom of the parent ring, or residues by removal of two hydrogen atoms from the same carbon atom or two different carbon atoms of the parent ring, i.e., “divalent cycloalkyl”, “divalent heterocyclyl”, “arylene” and “heteroarylene”.

In the chemical structure of the compound of the present disclosure, a bond “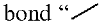” represents an unspecified configuration, namely if chiral isomers exist in the chemical structure, the bond “” may be “” or “”, or contains both the configurations of “” and “”.

The compounds and intermediates of the present disclosure may also exist in different tautomeric forms, and all such forms are included within the scope of the present disclosure. The term “tautomer” or “tautomeric form” refers to structural isomers of different energies that can interconvert via a low energy barrier. For example, proton tautomers (also known as proton transfer tautomers) include interconversion via proton migration, such as keto-enol and imine-enamine isomerization. An example of a lactam-lactim equilibrium is present between A and B as shown below.

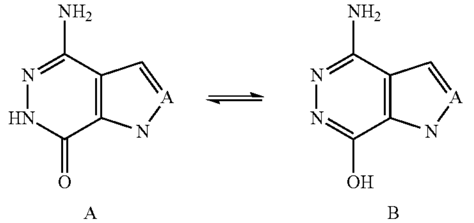

A B

All compounds in the present disclosure can be drawn as form A or form B. All tautomeric forms are within the scope of the present disclosure. The nomenclature of the compounds does not exclude any tautomers.

In another aspect, the compounds of the present disclosure may exist in specific stereoisomeric forms. The present disclosure contemplates all such compounds, including cis and trans isomers, (−)- and (+)-enantiomers, (R)- and (S)-enantiomers, diastereomers, (D)-isomer, (L)-isomer, and racemic mixtures and other mixtures thereof, such as enantiomerically or diastereomerically enriched mixtures, all of which are within the scope of the present disclosure. Additional asymmetric carbon atoms may be present in substituents such as an alkyl group. All such isomers and mixtures thereof are included within the scope of the present disclosure. Optically active (R)- and (S)-enantiomers, and D- and L-isomers can be prepared by chiral synthesis, chiral reagents or other conventional techniques. If one enantiomer of a certain compound of the present disclosure is desired, it may be prepared by asymmetric synthesis or derivatization with a chiral auxiliary, wherein the resulting mixture of diastereomers is separated and the auxiliary group is cleaved to provide the pure desired enantiomer. Alternatively, when the molecule contains a basic functional group (e.g., amino) or an acidic functional group (e.g., carboxyl), salts of diastereomers are formed with an appropriate optically active acid or base, followed by resolution of diastereomers by conventional methods known in the art, and the pure enantiomers are obtained by recovery. Furthermore, separation of enantiomers and diastereomers is typically accomplished by chromatography using a chiral stationary phase, optionally in combination with chemical derivatization (e.g., carbamate formation from amines).

The term “amino protecting group” refers to a group that can be readily removed and is intended to protect an amino group from being changed when a reaction is conducted elsewhere in the molecule. Non-limiting examples include (trimethylsilyl)ethoxymethyl, tetrahydropyranyl, tert-butoxycarbonyl, acetyl, benzyl, allyl, p-methoxybenzyl, and the like. Those groups may be optionally substituted with 1 to 3 substituents selected from the group consisting of halogen, alkoxy and nitro. The amino protecting groups are preferably (trimethylsilyl)ethoxymethyl and tert-butoxycarbonyl.

The term “hydroxy protecting group” is a suitable group known in the art for protecting hydroxy. See the hydroxy protecting groups in the literature (“Protective Groups in Organic Synthesis”, $5^{th}$ Ed. T. W. Greene & P. G. M. Wuts). As an example, preferably, the hydroxy protecting group may be ($C_{1-10}$ alkyl or aryl)$_3$silyl, e.g., triethylsilyl, triisopropylsilyl, tert-butyldimethylsilyl, tert-butyldiphenylsilyl or the like; $C_{1-10}$ alkyl or substituted alkyl, preferably alkoxy or aryl-substituted alkyl, more preferably $C_{1-6}$ alkoxy-substituted $C_{1-6}$ alkyl or phenyl-substituted $C_{1-6}$ alkyl, and most preferably $C_{1-4}$ alkoxy-substituted $C_{1-4}$ alkyl, e.g., methyl, tert-butyl, allyl, benzyl, methoxymethyl (MOM), ethoxyethyl, or the like; ($C_{1-10}$ alkyl or aryl)acyl, e.g., formyl, acetyl, benzoyl, p-nitrobenzoyl or the like; ($C_{1-6}$ alkyl or 6-membered to 10-membered aryl)sulfonyl; or ($C_{1-6}$ alkoxy or 6-membered to 10-membered aryloxy)carbonyl. The hydroxy protecting group is preferably p-nitrobenzoyl.

The term “heterocyclylalkyl” refers to alkyl substituted with one or more heterocyclyl groups, wherein the heterocyclyl and alkyl are as defined above.

The term “heteroarylalkyl” refers to alkyl substituted with one or more heteroaryl groups, wherein the heteroaryl and alkyl are as defined above.

The term "cycloalkyloxy" refers to cycloalkyl-O—, wherein the cycloalkyl is as defined above.

The term "heterocyclyloxy" refers to heterocyclyl-O—, wherein the heterocyclyl is as defined above.

The term "aryloxy" refers to aryl-O—, wherein the aryl is as defined above.

The term "heteroaryloxy" refers to heteroaryl-O—, wherein the heteroaryl is as defined above.

The term "alkylthio" refers to alkyl-S—, wherein the alkyl is as defined above.

The term "haloalkyl" refers to alkyl substituted with one or more halogens, wherein the alkyl is as defined above.

The term "haloalkoxy" refers to alkoxy substituted with one or more halogens, wherein the alkoxy is as defined above.

The term "deuterated alkyl" refers to alkyl substituted with one or more deuterium atoms, wherein the alkyl is as defined above.

The term "hydroxyalkyl" refers to alkyl substituted with one or more hydroxy groups, wherein the alkyl is as defined above.

The term "halogen" refers to fluorine, chlorine, bromine or iodine.

The term "hydroxy" refers to —OH.

The term "mercapto" refers to —SH.

The term "amino" refers to $—NH_2$.

The term "cyano" refers to —CN.

The term "nitro" refers to $—NO_2$.

The term "oxo" refers to "=O".

The term "carbonyl" refers to C=O.

The term "carboxyl" refers to —C(O)OH.

The term "carboxylate group" refers to —C(O)O(alkyl), —C(O)O(cycloalkyl), (alkyl)C(O)O— or (cycloalkyl)C(O)O—, wherein the alkyl and cycloalkyl are as defined above.

The compound of the present disclosure includes other isotopic derivatives. The term "isotopic derivative" refers to compounds that differ in structure only by having one or more enriched isotopic atoms. For example, compounds with the structure of the present disclosure having "deuterium" or "tritium" in place of hydrogen, or $^{18}$F-fluorine labeling ($^{18}$F isotope) in place of fluorine, or $^{11}$C-, $^{13}$C- or $^{14}$C-enriched carbon ($^{11}$C-, $^{13}$C- or $^{14}$C-carbon labeling; $^{13}$C- or $^{14}$C-isotope) in place of a carbon atom are within the scope of the present disclosure. Such a compound can be used as an analytical tool or a probe in, for example, a biological assay, or may be used as a tracer for in vivo diagnostic imaging of disease, or as a tracer in a pharmacodynamic, pharmacokinetic or receptor study. The deuterated forms of the compound mean that each available hydrogen atom connected to a carbon atom may be independently replaced with a deuterium atom. Those skilled in the art are able to synthesize the deuterated compounds with reference to the relevant literature. Commercially available deuterated starting materials can be used in preparing the deuterated compounds, or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like. Deuterides can generally retain comparable activity to non-deuterated compounds and can achieve better metabolic stability when deuterated at certain specific sites, thereby achieving certain therapeutic advantages.

The term "optional" or "optionally" means that the event or circumstance subsequently described may, but not necessarily, occur, and that the description includes instances where the event or circumstance occurs or does not occur. For example, the expression "a heterocyclyl group optionally substituted with alkyl" means that the alkyl may be, but not necessarily, present, and includes instances where the heterocyclyl group is or is not substituted with the alkyl.

The term "substituted" means that one or more, preferably 1-5, more preferably 1-3 hydrogen atoms in the group are independently substituted with a corresponding number of substituents. Those skilled in the art are able to determine (experimentally or theoretically) possible or impossible substitution without undue efforts. For example, it may be unstable when an amino or hydroxy group having a free hydrogen is bound to a carbon atom having an unsaturated (e.g., olefinic) bond.

The term "pharmaceutical composition" refers to a mixture containing one or more of the compounds described herein or a physiologically/pharmaceutically acceptable salt or pro-drug thereof, and other chemical components, and other components, for example, physiologically/pharmaceutically acceptable carriers and excipients. The pharmaceutical composition is intended to promote the administration to an organism, so as to facilitate the absorption of the active ingredient, thereby exerting biological activities.

The term "pharmaceutically acceptable salt" refers to the salts of the compound of the present disclosure, which are safe and effective for use in the body of a mammal and possess the requisite biological activities. The salts may be prepared separately during the final separation and purification of the compound, or by reacting an appropriate group with an appropriate base or acid. Bases commonly used to form pharmaceutically acceptable salts include inorganic bases such as sodium hydroxide and potassium hydroxide, and organic bases such as ammonia. Acids commonly used to form pharmaceutically acceptable salts include inorganic acids and organic acids.

As used herein, unless otherwise stated, the term "prevention" refers to treatment with or administration of a compound provided herein, with or without other active compounds, to a patient, especially at risk of cancer and/or other disorders described herein, prior to the onset of symptoms. The term "prevention" includes the inhibition or alleviation of the symptoms of a particular disease. In certain embodiments, patients with a family history of disease may be particularly candidates for prophylactic regimens. In addition, patients with a history of recurrence of symptoms are also potential candidates for prevention. In this regard, the term "prevention" may be used interchangeably with the term "prophylactic treatment".

For drugs and pharmacological active agents, the term "therapeutically effective amount" refers to an amount of a medicament or an agent that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

The term "pharmaceutically acceptable" used herein means that those compounds, materials, compositions and/or dosage forms which are, within the scope of reasonable medical judgment, suitable for use in contact with the tissues of patients without excessive toxicity, irritation, allergic reaction, or other problems or complications, and are commensurate with a reasonable benefit/risk ratio and effective for the intended use.

As used herein, the singular forms "a", "an" and "the" include plural references and vice versa, unless otherwise clearly defined in the context.

When the term "about" is applied to parameters such as pH, concentration and temperature, it means that the parameter may vary by ±10%, and sometimes more preferably within ±5%. As will be appreciated by those skilled in the art, when the parameters are not critical, the numbers are generally given for illustrative purposes only and are not intended to be limiting.

Synthesis Method of Compounds of the Present Disclosure

In order to achieve the purpose of the present disclosure, the following technical schemes are adopted in the present disclosure:

-continued

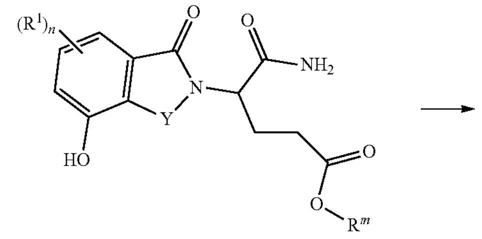

(ID)

Scheme 1

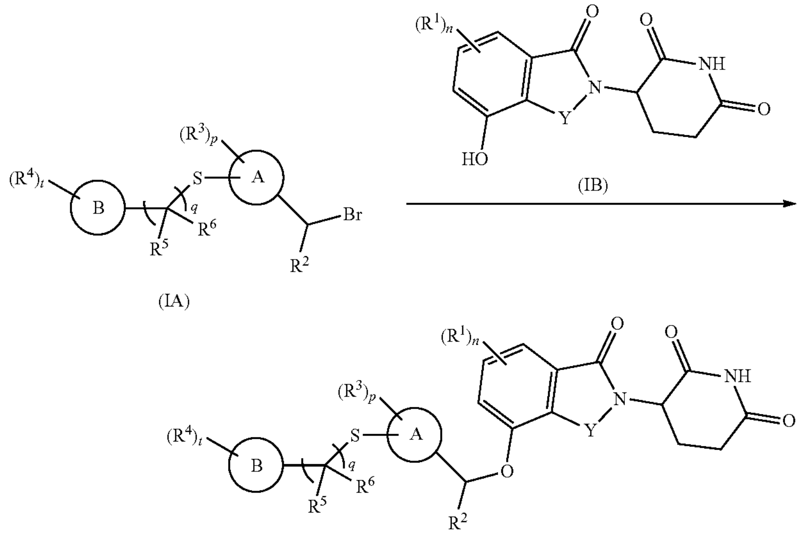

(IB)

(IA)

(I)

Provided is a method for preparing the compound of general formula (I) or the tautomer, mesomer, racemate, enantiomer or diastereomer thereof or the mixture thereof, or the pharmaceutically acceptable salt thereof of the present disclosure, which comprises the following step:

subjecting a compound of general formula (IA) and a compound of general formula (IB) to a reaction under an alkaline condition to obtain the compound of general formula (I), wherein:

ring A, ring B, Y, $R^1$ to $R^6$, n, p, q and t are as defined in general formula (I).

Scheme 2

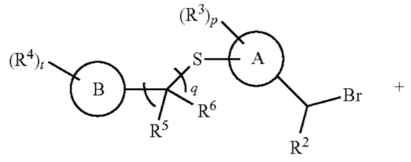

(IA)

-continued

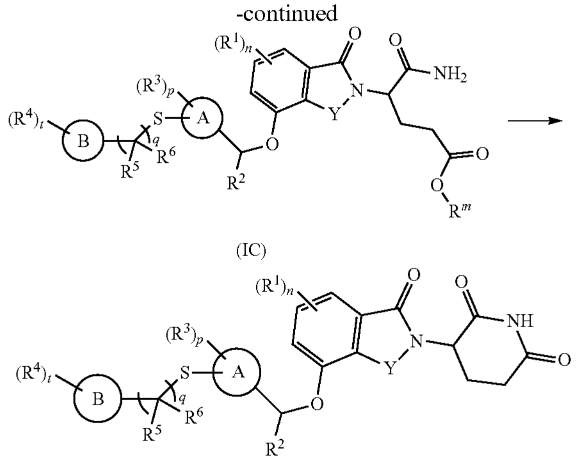

(IC)

(I)

Provided is a method for preparing the compound of general formula (I) or the tautomer, mesomer, racemate, enantiomer or diastereomer thereof or the mixture thereof, or the pharmaceutically acceptable salt thereof of the present disclosure, which comprises the following steps:

subjecting a compound of general formula (IA) and a compound of general formula (ID) to a reaction under an alkaline condition to obtain a compound of formula (IC), and subjecting the compound of general formula (IC) to an intramolecular ring closure reaction under an acidic condition to obtain the compound of general formula (I), wherein:

$R^m$ is $C_{1-6}$ alkyl; preferably tert-butyl; and ring A, ring B, Y, $R^1$ to $R^6$, n, p, q and t are as defined in general formula (I).

Scheme 3

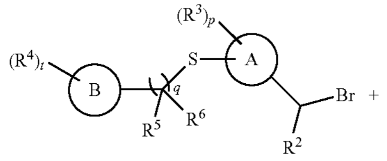

(IA)

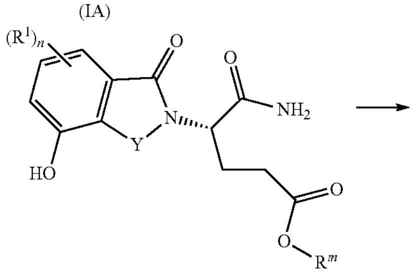

(I-1D)

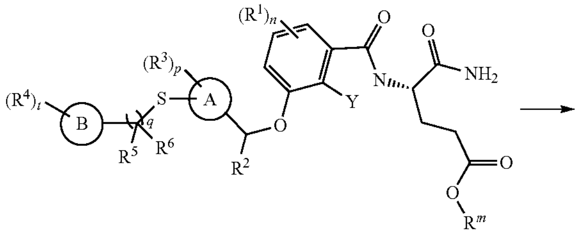

(I-1C)

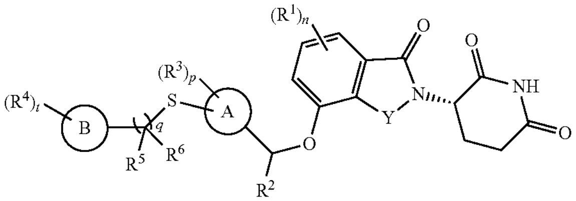

(I-1)

Provided is a method for preparing the compound of general formula (I-1) or the tautomer, mesomer, racemate, enantiomer or diastereomer thereof or the mixture thereof, or the pharmaceutically acceptable salt thereof of the present disclosure, which comprises the following steps:

subjecting a compound of general formula (IA) and a compound of general formula (I-1D) to a reaction under an alkaline condition to obtain a compound of formula (I-1C), and subjecting the compound of general formula (I-1C) to an intramolecular ring closure reaction under an acidic condition to obtain the compound of general formula (I-1), wherein:

$R^m$ is $C_{1-6}$ alkyl; preferably tert-butyl; and ring A, ring B, Y, $R^1$ to $R^6$, n, p, q and t are as defined in general formula (I-1).

Scheme 4

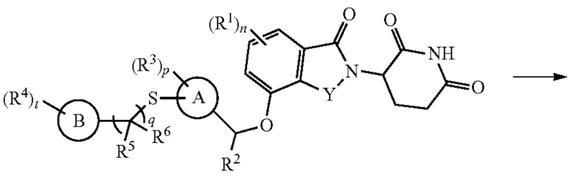

(I)

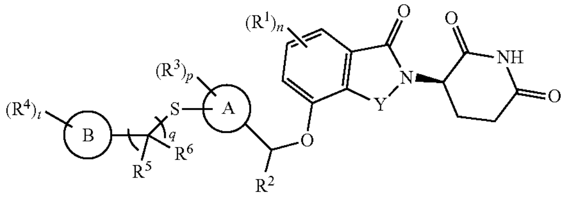

(I-2)

Provided is a method for preparing the compound of general formula (I-2) or the tautomer, mesomer, racemate, enantiomer or diastereomer thereof or the mixture thereof, or the pharmaceutically acceptable salt thereof of the present disclosure, which comprises the following step:

subjecting a compound of general formula (I) or a tautomer, mesomer, racemate, enantiomer or diastereomer thereof or a mixture thereof, or a pharmaceutically acceptable salt thereof to a preparative chiral resolution to obtain the compound of general formula (I-2) or the tautomer, mesomer, racemate, enantiomer or diastereomer thereof or the mixture thereof, or the pharmaceutically acceptable salt thereof, wherein:

$R^m$ is $C_{1-6}$ alkyl; preferably tert-butyl; and ring A, ring B, Y, $R^1$ to $R^6$, n, p, q and t are as defined in general formula (I).

Scheme 5

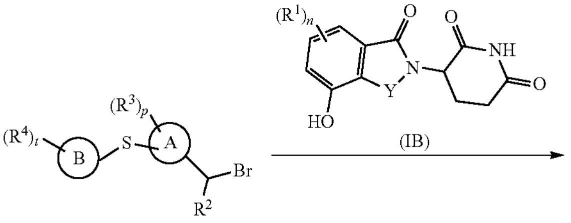

(IB)

(IIA)

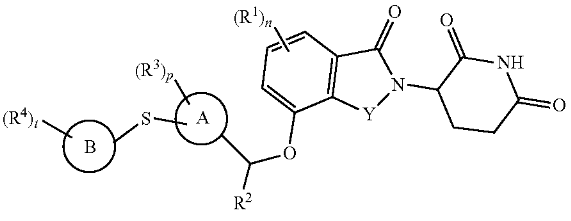

(II)

Provided is a method for preparing the compound of general formula (II) or the tautomer, mesomer, racemate, enantiomer or diastereomer thereof or the mixture thereof the pharmaceutically acceptable salt thereof of the present disclosure, which comprises the following step:

subjecting a compound of general formula (IIA) and a compound of general formula (IB) to a reaction under an alkaline condition to obtain the compound of general formula (II), wherein:

ring A, ring B, Y, $R^1$ to $R^4$, n, p and t are as defined in general formula (II).

Scheme 6

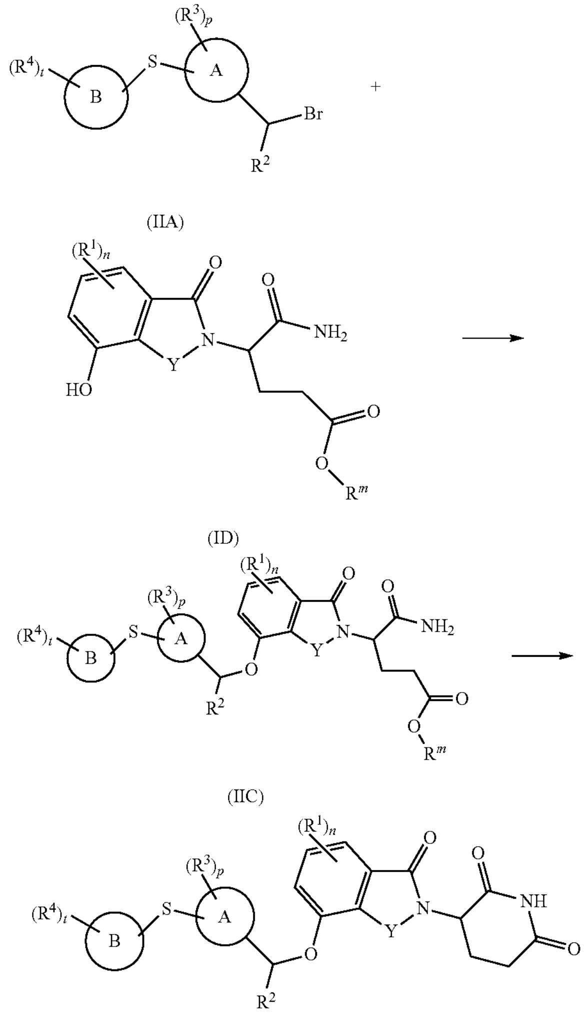

(IIA)

(ID)

(IIC)

(II)

Provided is a method for preparing the compound of general formula (II) or the tautomer, mesomer, racemate, enantiomer or diastereomer thereof or the mixture thereof the pharmaceutically acceptable salt thereof of the present disclosure, which comprises the following steps:

subjecting a compound of general formula (IIA) and a compound of general formula (ID) to a reaction under an alkaline condition to obtain a compound of formula (IIC), and subjecting the compound of general formula (IIC) to an intramolecular ring closure reaction under an acidic condition to obtain the compound of general formula (II), wherein:

$R^m$ is $C_{1-6}$ alkyl; preferably tert-butyl; and ring A, ring B, Y, $R^1$ to $R^4$, n, p and t are as defined in general formula (II).

Scheme 7

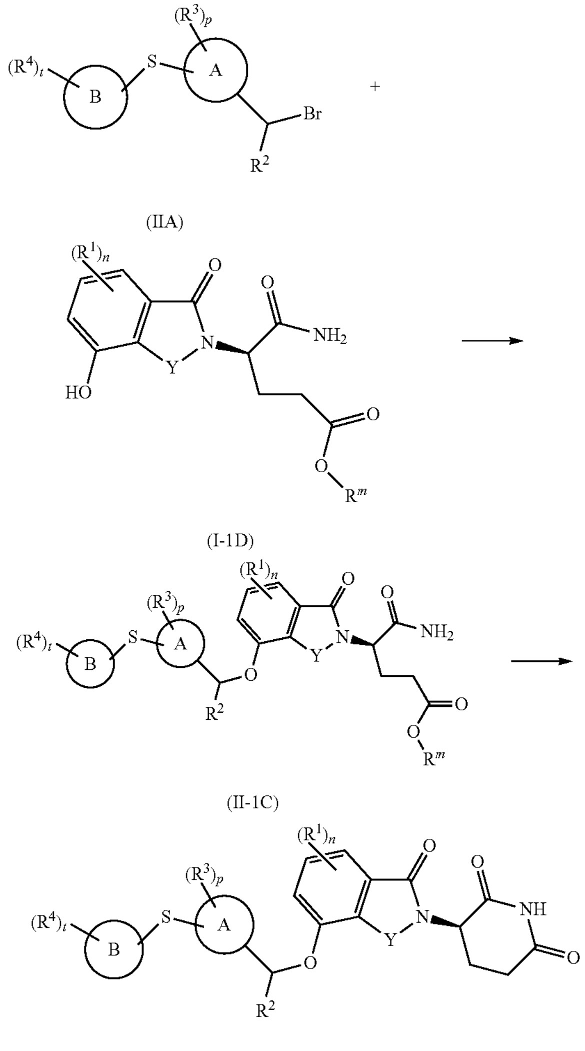

(IIA)

(I-1D)

(II-1C)

(II-1)

Provided is a method for preparing the compound of general formula (II-1) or the tautomer, mesomer, racemate, enantiomer or diastereomer thereof or the mixture thereof the pharmaceutically acceptable salt thereof of the present disclosure, which comprises the following steps:

subjecting a compound of general formula (IIA) and a compound of general formula (I-1D) to a reaction under an alkaline condition to obtain a compound of formula (II-1C), and subjecting the compound of general formula (II-1C) to an intramolecular ring closure reaction under an acidic condition to obtain the compound of general formula (II-1), wherein:

$R^m$ is $C_{1-6}$ alkyl; preferably tert-butyl; and ring A, ring B, Y, $R^1$ to $R^4$, n, p and t are as defined in general formula (II-1).

Scheme 8

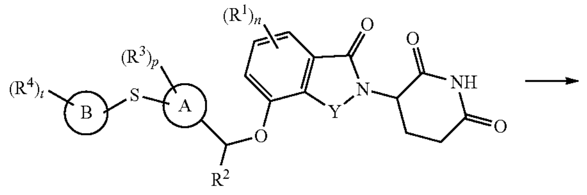

(II)

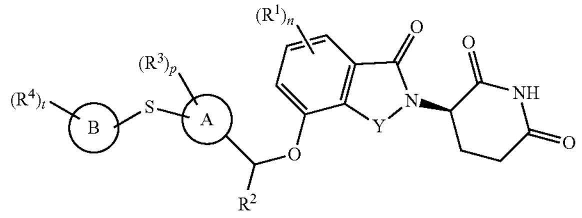

(II-2)

Provided is a method for preparing the compound of general formula (II-2) or the tautomer, mesomer, racemate, enantiomer or diastereomer thereof or the mixture thereof the pharmaceutically acceptable salt thereof of the present disclosure, which comprises the following step:

subjecting a compound of general formula (II) or a tautomer, mesomer, racemate, enantiomer or diastereomer thereof or a mixture thereof, or a pharmaceutically acceptable salt thereof to a preparative chiral resolution to obtain the compound of general formula (II-2) or the tautomer, mesomer, racemate, enantiomer or diastereomer thereof or the mixture thereof, or the pharmaceutically acceptable salt thereof, wherein:

$R^m$ is $C_{1-6}$ alkyl; preferably tert-butyl; and ring A, ring B, Y, $R^1$ to $R^4$, n, p and t are as defined in general formula (II).

Scheme 9

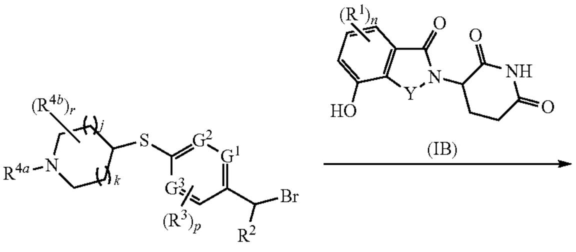

(IB)

(IIGA)

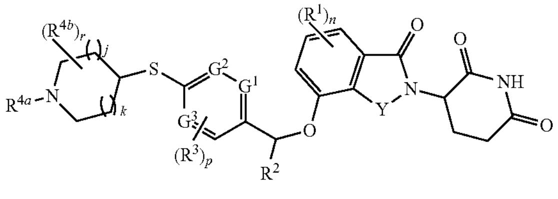

(IIG)

Provided is a method for preparing the compound of general formula (IIG) or the tautomer, mesomer, racemate, enantiomer or diastereomer thereof or the mixture thereof the pharmaceutically acceptable salt thereof of the present disclosure, which comprises the following step:

subjecting a compound of general formula (IIGA) and a compound of general formula (IB) to a reaction under an alkaline condition to obtain the compound of general formula (IIG), wherein:

$G^1$, $G^2$, $G^3$, Y, $R^1$ to $R^3$, $R^{4a}$, $R^{4b}$, J, k, n, p and r are as defined in general formula (IIG).

Scheme 10

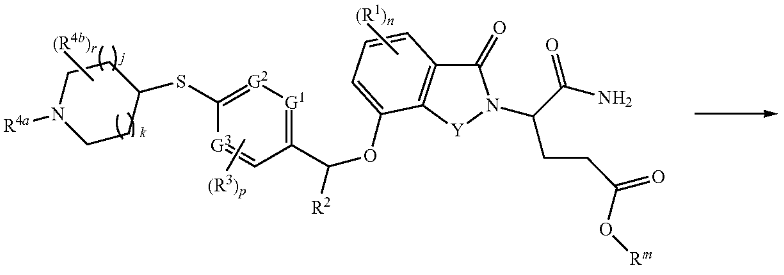

(IIGC)

-continued

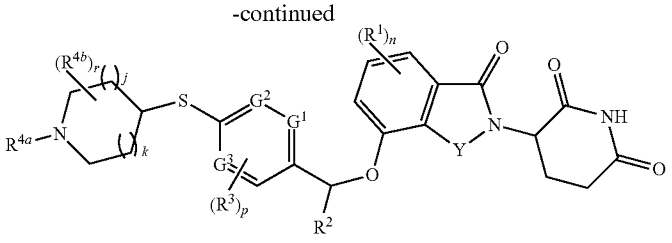

(IIG)

Provided is a method for preparing the compound of general formula (IIG) or the tautomer, mesomer, racemate, enantiomer or diastereomer thereof or the mixture thereof the pharmaceutically acceptable salt thereof of the present disclosure, which comprises the following step:

subjecting a compound of general formula (IIGC) to an intramolecular ring closure reaction under an acidic condition to obtain the compound of general formula (IIG), wherein:

$R^m$ is $C_{1-6}$ alkyl; preferably tert-butyl; and $G^1$, $G^2$, $G^3$, Y, $R^1$ to $R^3$, $R^{4a}$, $R^{4b}$, J, k, n, p and r are as defined in general formula (IIG).

Scheme 11

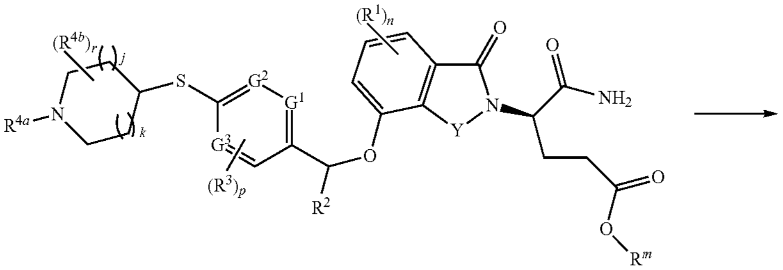

(IIGC-1)

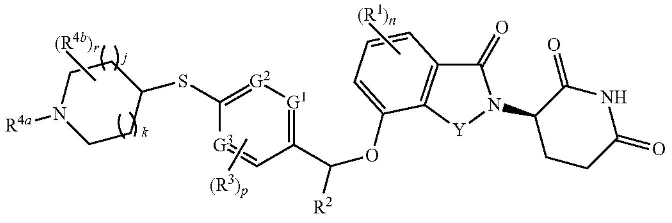

(IIG-1)

Provided is a method for preparing the compound of general formula (IIG-1) or the tautomer, mesomer, racemate, enantiomer or diastereomer thereof or the mixture thereof the pharmaceutically acceptable salt thereof of the present disclosure, which comprises the following step:

subjecting a compound of general formula (IIGC-1) to an intramolecular ring closure reaction under an acidic condition to obtain the compound of general formula (IIG-1), wherein:

$R^m$ is $C_{1-6}$ alkyl; preferably tert-butyl; and $G^1$, $G^2$, $G^3$, Y, $R^1$ to $R^3$, $R^{4a}$, $R^{4b}$, J, k, n, p and r are as defined in general formula (IIG-1).

Scheme 12

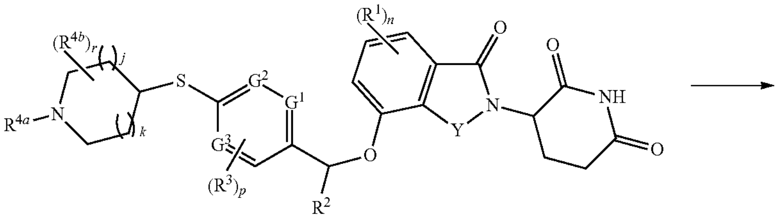

(IIG)

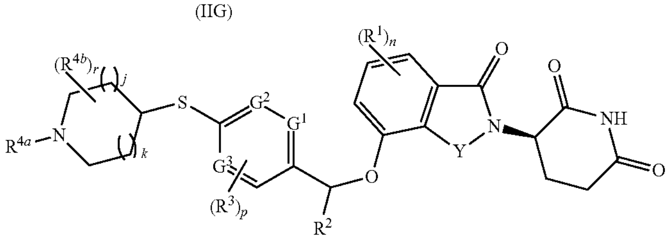

(IIG-2)

Provided is a method for preparing the compound of general formula (IIG-2) or the tautomer, mesomer, racemate, enantiomer or diastereomer thereof or the mixture thereof the pharmaceutically acceptable salt thereof of the present disclosure, which comprises the following step:

subjecting a compound of general formula (IIG) or a tautomer, mesomer, racemate, enantiomer or diastereomer thereof or a mixture thereof, or a pharmaceutically acceptable salt thereof to a preparative chiral resolution to obtain the compound of general formula (IIG-2) or the tautomer, mesomer, racemate, enantiomer or diastereomer thereof or the mixture thereof, or the pharmaceutically acceptable salt thereof, wherein:

$R^m$ is $C_{1-6}$ alkyl; preferably tert-butyl; and $G^1$, $G^2$, $G^3$, Y, $R^1$ to $R^3$, $R^{4a}$, $R^{4b}$, J, k, n, p and r are as defined in general formula (IIG).

Scheme 13

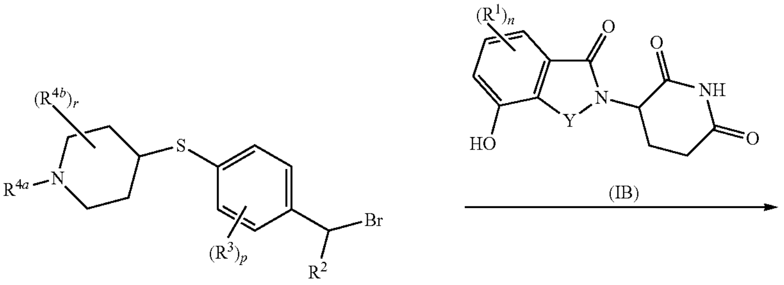

(IIIA)

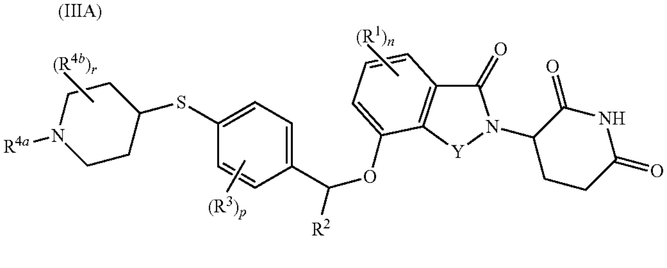

(III)

Provided is a method for preparing the compound of general formula (III) or the tautomer, mesomer, racemate, enantiomer or diastereomer thereof or the mixture thereof the pharmaceutically acceptable salt thereof of the present disclosure, which comprises the following step:

subjecting a compound of general formula (IIIA) and a compound of general formula (IB) to a reaction under an alkaline condition to obtain the compound of formula (III), wherein:

Y, $R^1$ to $R^3$, $R^{4a}$, $R^{4b}$, n, p and r are as defined in general formula (III).

Scheme 14

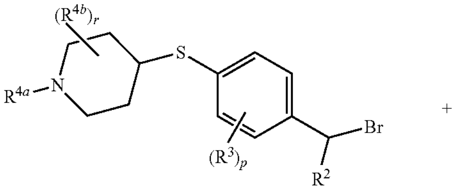

(IIIA)

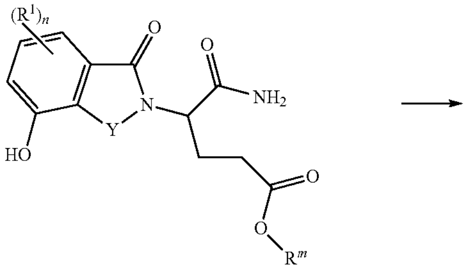

(ID)

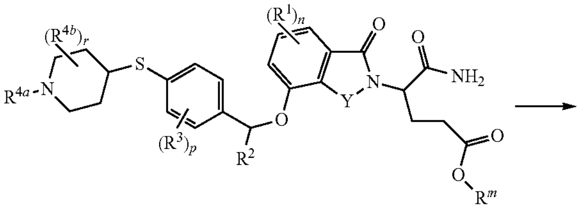

(IIIC)

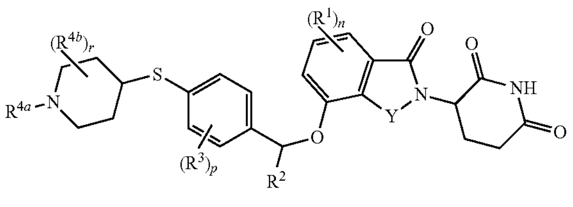

(III)

Provided is a method for preparing the compound of general formula (III) or the tautomer, mesomer, racemate, enantiomer or diastereomer thereof or the mixture thereof the pharmaceutically acceptable salt thereof of the present disclosure, which comprises the following steps:

subjecting a compound of general formula (IIIA) and a compound of general formula (ID) to a reaction under an alkaline condition to obtain the compound of formula (IIIC), and subjecting the compound of general formula (IIIC) to an intramolecular ring closure reaction under an acidic condition to obtain the compound of general formula (III), wherein:

$R^m$ is $C_{1-6}$ alkyl; preferably tert-butyl; and

Y, $R^1$ to $R^3$, $R^{4a}$, $R^{4b}$, n, p and r are as defined in general formula (III).

Scheme 15

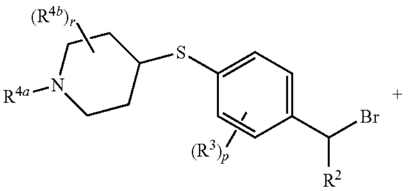

(IIIA)

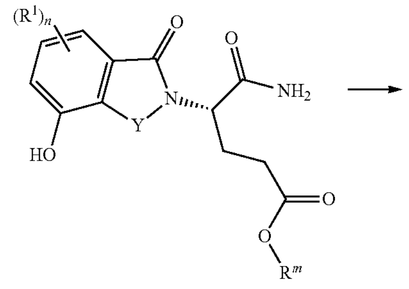

(I-1D)

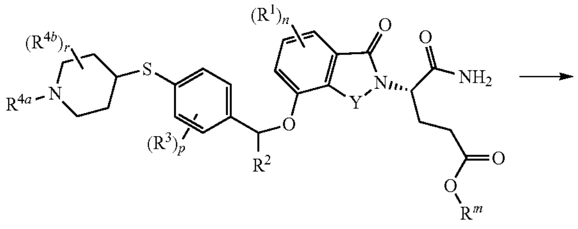

(III-1C)

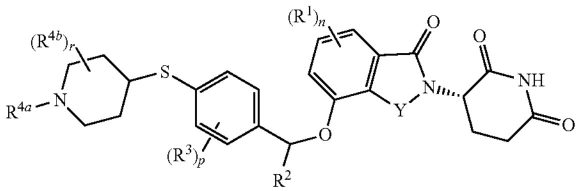

(III-1)

Provided is a method for preparing the compound of general formula (III-1) or the tautomer, mesomer, racemate, enantiomer or diastereomer thereof or the mixture thereof the pharmaceutically acceptable salt thereof of the present disclosure, which comprises the following steps:

subjecting a compound of general formula (IIIA) and a compound of general formula (I-1D) to a reaction under an alkaline condition to obtain a compound of formula (III-1C), and subjecting the compound of general formula (III-1C) to an intramolecular ring closure reaction under an acidic condition to obtain the compound of general formula (III-1), wherein:

$R^m$ is $C_{1-6}$ alkyl; preferably tert-butyl; and

Y, $R^1$ to $R^3$, $R^{4a}$, $R^{4b}$, n, p and r are as defined in general formula (III-1).

Scheme 16

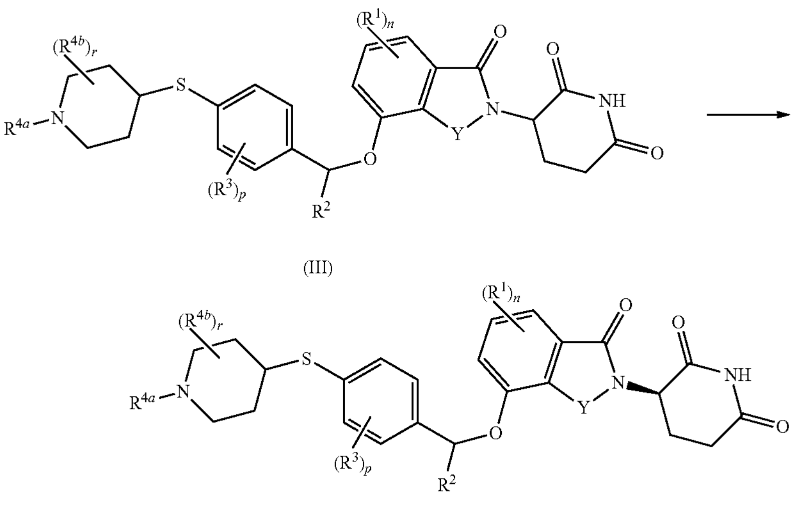

(III)

(III-2)

Provided is a method for preparing the compound of general formula (III-2) or the tautomer, mesomer, racemate, enantiomer or diastereomer thereof or the mixture thereof the pharmaceutically acceptable salt thereof of the present disclosure, which comprises the following step:

subjecting a compound of general formula (III) or a tautomer, mesomer, racemate, enantiomer or diastereomer thereof or a mixture thereof, or a pharmaceutically acceptable salt thereof to a preparative chiral resolution to obtain the compound of general formula (III-2) or the tautomer, mesomer, racemate, enantiomer or diastereomer thereof or the mixture thereof, or the pharmaceutically acceptable salt thereof, wherein:

$R^m$ is $C_{1-6}$ alkyl; preferably tert-butyl; and

Y, $R^1$ to $R^3$, $R^{4a}$, $R^{4b}$, n, p and r are as defined in general formula (III).

Reagents that provide alkaline conditions in the above synthetic schemes include organic bases and inorganic bases, wherein the organic bases include, but are not limited to, triethylamine, N,N-diisopropylethylamine, n-butyllithium, lithium diisopropylamide, sodium acetate, potassium acetate, sodium tert-butoxide or potassium tert-butoxide, and the inorganic bases include, but are not limited to, sodium hydride, potassium phosphate, sodium carbonate, potassium carbonate, cesium carbonate, sodium hydroxide, lithium hydroxide monohydrate, lithium hydroxide and potassium hydroxide, and preferably potassium carbonate.

Reagents that provide acidic conditions in the above synthetic schemes include, but are not limited to, p-toluenesulfonic acid, p-toluenesulfonic acid monohydrate, benzenesulfonic acid, methanesulfonic acid, trifluoromethanesulfonic acid, sulfuric acid, hydrochloric acid, nitric acid, and trifluoroacetic acid; preferably selected from the group consisting of p-toluenesulfonic acid, p-toluenesulfonic acid monohydrate and benzenesulfonic acid.

The above reactions are preferably performed in solvents including, but not limited to ethylene glycol dimethyl ether, acetic acid, methanol, ethanol, acetonitrile, n-butanol, toluene, tetrahydrofuran, dichloromethane, petroleum ether, ethyl acetate, n-hexane, dimethyl sulfoxide, 1,4-dioxane, water, N,N-dimethylacetamide, N,N-dimethylformamide and mixtures thereof.

DETAILED DESCRIPTION

Figure 1:
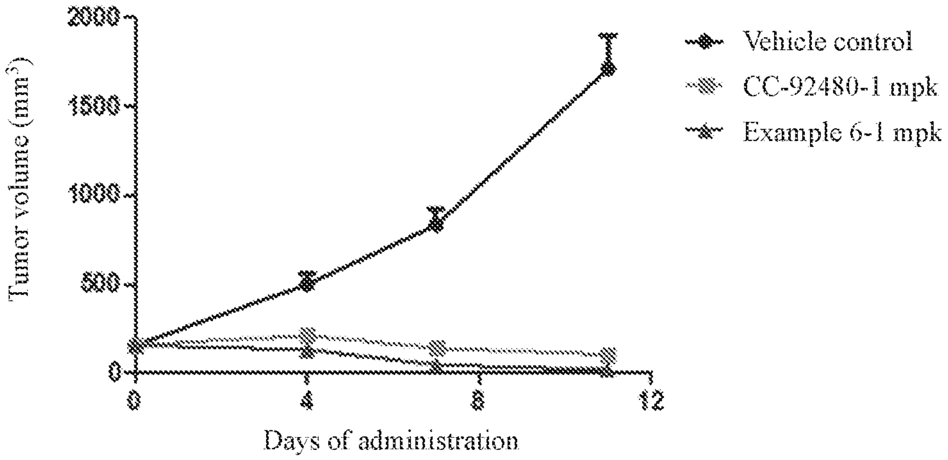
FIG. 1: data on the efficacy of the compound of Example 6 and the control example CC-92480 on NCI-H929 xenograft tumor in CB-17 SCID mice.

The present disclosure is further described below with reference to examples below, which are not intended to limit the scope of the present disclosure.

EXAMPLES

The structure of the compound is determined by nuclear magnetic resonance (NMR) spectroscopy and/or mass spectrometry (MS). NMR shift (δ) is given in a unit of $10^{-6}$ (ppm). NMR spectra are determined using a Bruker AVANCE-400 nuclear magnetic resonance instrument or Bruker AVANCE NEO 500M, with deuterated dimethyl sulfoxide (DMSO-$d_6$), deuterated chloroform ($CDCl_3$) and deuterated methanol ($CD_3OD$) as determination solvents and tetramethylsilane (TMS) as an internal standard.

Mass spectra are determined using Agilent 1200/1290 DAD-6110/6120 Quadrupole MS liquid chromatography-mass spectrometry system (manufacturer: Agilent; MS model: 6110/6120 Quadrupole MS), Waters ACQuity UPLC-QD/SQD (manufacturer: Waters, MS model: Waters ACQuity Qda Detector/Waters SQ Detector) and THERMO Ultimate 3000-Q Exactive (manufacturer: THERMO, MS model: THERMO Q Exactive).

High performance liquid chromatography (HPLC) analysis is performed using Agilent HPLC 1200DAD, Agilent HPLC 1200VWD and Waters HPLC e2695-2489 high performance liquid chromatographs.

Chiral HPLC analysis is performed using an Agilent 1260 DAD high performance liquid chromatograph.

HPLC preparation is performed using Waters 2545-2767, Waters 2767-SQ Detecor2, Shimadzu LC-20AP and Gilson GX-281 preparative chromatographs.

Chiral preparative HPLC is performed using a Shimadzu LC-20AP preparative chromatograph.

A CombiFlash rapid preparation instrument used is Combiflash Rf200 (TELEDYNE ISCO).

Huanghai HSGF254 or Qingdao GF254 silica gel plates of specifications 0.15 mm to 0.2 mm are adopted for thin layer chromatography (TLC) analysis and 0.4 mm to 0.5 mm for TLC separation and purification.

Yantai Huanghai silica gel of 200-300 mesh is generally used as a carrier in silica gel column chromatography.

The mean inhibition of kinase and the $IC_{50}$ value are determined using a NovoStar microplate reader (BMG, Germany).

Known starting materials described herein may be synthesized using or according to methods known in the art, or may be purchased from ABCR GmbH & Co. KG, Acros Organics, Aldrich Chemical Company, Accela ChemBio Inc., Shanghai Bide Pharmatech, Chembee Chemicals, and other companies.

In the examples, the reactions can be performed in an argon atmosphere or a nitrogen atmosphere unless otherwise specified.

The argon atmosphere or nitrogen atmosphere means that the reaction flask is connected to a balloon containing about 1 L of argon or nitrogen.

The hydrogen atmosphere means that the reaction flask is connected to a balloon containing about 1 L of hydrogen.

Parr 3916EKX hydrogenator, Qinglan QL-500 hydrogenator or HC2-SS hydrogenator is used in the pressurized hydrogenation reactions.

The hydrogenation reactions usually involve 3 cycles of vacuumization and hydrogen purge.

A CEM Discover-S 908860 microwave reactor is used in the microwave reactions.

In the examples, a solution refers to an aqueous solution unless otherwise specified.

In the examples, the reaction temperature is room temperature, i.e., 20° C. to 30° C., unless otherwise specified.

The monitoring of the reaction progress in the examples is conducted by thin layer chromatography (TLC). The developing solvent for reactions, the eluent system for column chromatography purification and the developing solvent system for thin layer chromatography include: A: dichloromethane/methanol system, and B: n-hexane/ethyl acetate system. The volume ratio of the solvents was adjusted according to the polarity of the compound, or by adding a small amount of basic or acidic reagents such as triethylamine and acetic acid.

Example 1

4-(4-((4-(((2-(2,6-dioxopiperidin-3-yl)-1-oxoisoindolin-4-yl)oxy)methyl)phenyl)thio)piperidin-1-yl)-3-fluorobenzonitrile 1

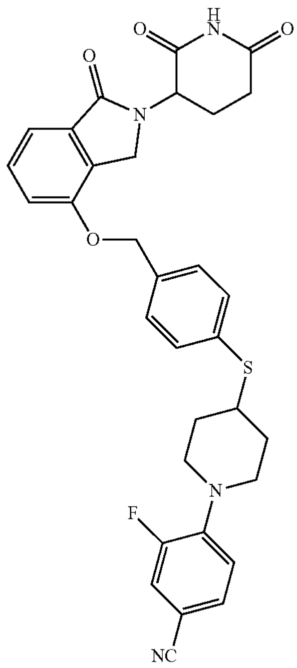

1

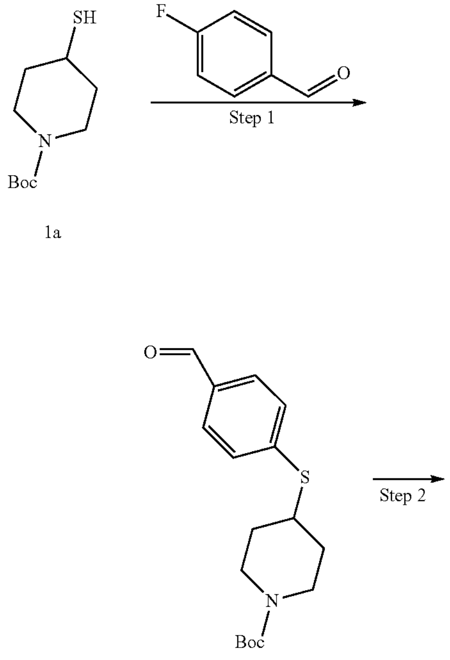

1a

1b

-continued

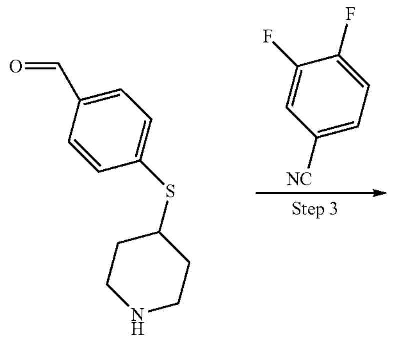

HCl

1c

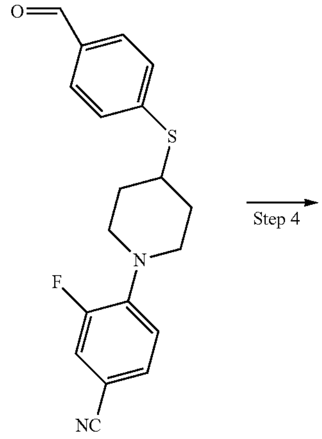

1d

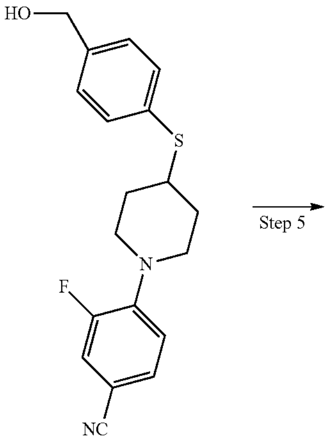

1e

-continued

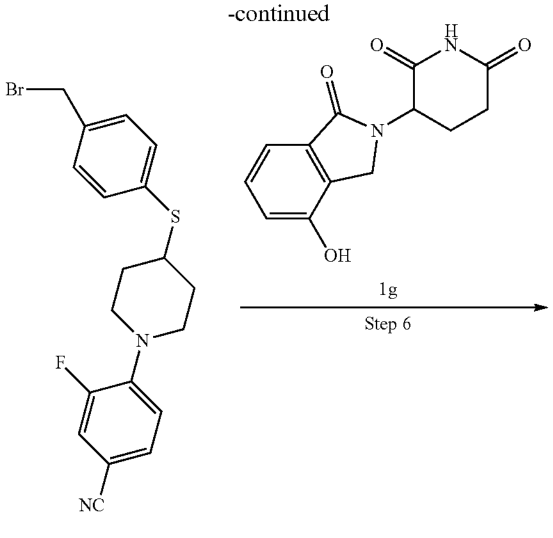

1f

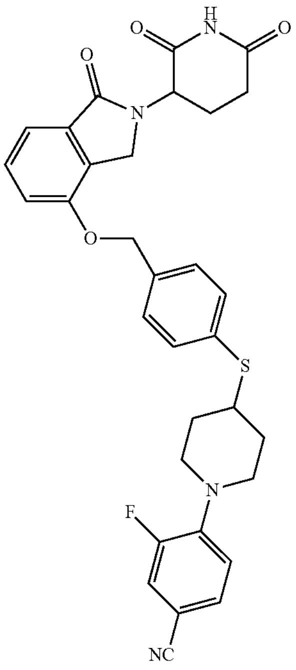

1

Step 1

Tert-butyl 4-((4-formylphenyl)thio)piperidine-1-carboxylate 1b

Tert-butyl 4-mercaptopiperidine-1-carboxylate 1a (2.05 g, 9.44 mmol, Bide Pharmatech Ltd.), 4-fluorobenzaldehyde (1.17 g, 9.44 mmol) and potassium carbonate (2.86 g, 20.71 mmol) were added to N,N-dimethylformamide (40 mL). The mixture was heated to 120° C. and reacted overnight. After the reaction was completed, the reaction solution was diluted with water (200 mL) and extracted with ethyl acetate (100 mL×3). The organic phases were combined, washed with a saturated sodium chloride solution (100 mL), dried over anhydrous sodium sulfate and filtered, and the filtrate was concentrated under reduced pressure. The residue was purified by column chromatography with an eluent system B to give the title compound 1b (2.66 g, yield: 88%).

MS m/z (ESI): 266.1 [M−55].

Step 2

4-(piperidin-4-ylthio)benzaldehyde Hydrogen Chloride 1c

Compound 1b (2.66 g, 8.28 mmol) was dissolved in solution of 4 M hydrogen chloride in 1,4-dioxane (20 mL), and the solution was stirred for about 3 h. The reaction solution was filtered, and the filter cake was rinsed with ethyl acetate (3 mL×3) and dried naturally to give the title compound 1c (crude product), which was directly used in the next step.

MS m/z (ESI): 221.8 [M+1].

Step 3

3-fluoro-4-(4-((4-formylphenyl)thio)piperidin-1-yl)benzonitrile 1d

Compound 1c (1.89 g, 7.33 mmol), 3,4-difluorobenzonitrile (1.07 g, 7.70 mmol, Bide Pharmatech Ltd.) and potassium carbonate (4.05 g, 29.33 mmol) were added to N,N-dimethylacetamide (15 mL), and the mixture was heated to 120° C. and reacted overnight. The reaction was added with water (50 mL) and extracted with ethyl acetate (30 mL×3). The organic phases were combined, washed with saturated sodium chloride solution (50 mL×3), dried over anhydrous sodium sulfate, filtered and concentrated. The resulting residue was purified by column chromatography with an eluent system B to give the title compound 1d (2.2 g, yield: 93%).

MS m/z (ESI): 341.0 [M+1].

Step 4

3-fluoro-4-(4-((4-(hydroxymethyl)phenyl)thio)piperidin-1-yl)benzonitrile 1e

Compound 1d (150 mg, 0.44 mmol) was added to methanol (8 mL) under an ice bath, followed by the addition of potassium borohydride (29 mg, 0.53 mmol), and the mixture was reacted for 2 h under an ice bath. The reaction solution was diluted with water (20 mL) and extracted with ethyl acetate (30 mL×3). The organic phases were combined, washed with a saturated aqueous sodium chloride solution (30 mL), dried over anhydrous sodium sulfate and filtered, and the filtrate was concentrated under reduced pressure. The residue was purified by silica gel column chromatography with an eluent system B to give the title compound 1e (150 mg, yield: 99%).

MS m/z (ESI): 343.1 [M+1].

Step 5

4-(4-((4-(bromomethyl)phenyl)thio)piperidin-1-yl)-3-fluorobenzonitrile 1f

Compound 1e (150 mg, 0.43 mmol) was added to dichloromethane (8 mL) under an ice bath, followed by the sequential addition of triphenylphosphine (150 mg, 0.57 mmol) and carbon tetrabromide (189 mg, 0.57 mmol), and the mixture was reacted for 20 min under an ice bath, and heated to room temperature and reacted for 2 h. The reaction solution was concentrated. The residue was purified by column chromatography with an eluent system B to give the title compound 1f (120 mg, yield: 68%).

MS m/z (ESI): 405.0 [M+1]; 407.0 [M+3].

Step 6

4-(4-((4-(((2-(2,6-dioxopiperidin-3-yl)-1-oxoisoindolin-4-yl)oxy)methyl)phenyl)thio)piperidin-1-yl)-3-fluorobenzonitrile 1

3-(4-hydroxy-1-oxoisoindolin-2-yl)piperidine-2,6-dione 1g (25 mg, 0.096 mmol, Jiangsu Aikon Biopharmaceutical R&D Co., Ltd.) and anhydrous potassium carbonate (27 mg, 0.096 mmol) were added to N,N-dimethylacetamide (3 mL), and compound 1f (38 mg, 0.093 mmol) was added and reacted for 16 h. The reaction solution was filtered and purified by high performance liquid chromatography (Waters 2767-SQ Detecor2, elution system: 10 mmol/L aqueous ammonium bicarbonate solution and acetonitrile, gradient of acetonitrile: 55%-70%, flow rate: 30 mL/min) to give the title compound 1 (16 mg, yield: 28%).

MS m/z (ESI): 585.1 [M+1].

$^1$H NMR (400 MHz, DMSO-$d_6$) 10.99 (s, 1H), 7.69 (dd, 1H), 7.55 (dd, 1H), 7.52-7.43 (m, 5H), 7.37-7.29 (m, 2H), 7.13 (t, 1H), 5.25 (s, 2H), 5.12 (dd, 1H), 4.43 (d, 1H), 4.27 (d, 1H), 3.58-3.42 (m, 3H), 3.05-2.83 (m, 3H), 2.63-2.52 (m, 1H), 2.48-2.38 (m, 1H), 2.06-1.93 (m, 3H), 1.68-1.55 (m, 2H).

Example 2

4-(4-((4-(((2-(2,6-dioxopiperidin-3-yl)-1,3-dioxoisoindolin-4-yl)oxy)methyl)phenyl)thio)piperidin-1-yl)-3-fluorobenzonitrile 2

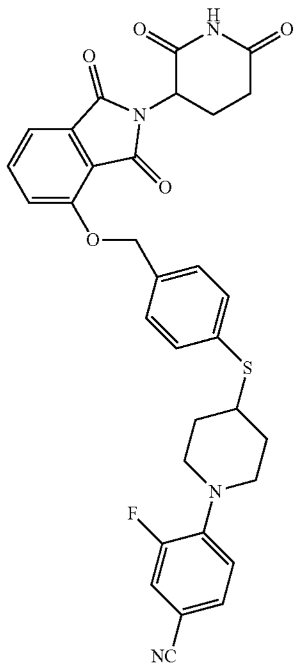

2

-continued

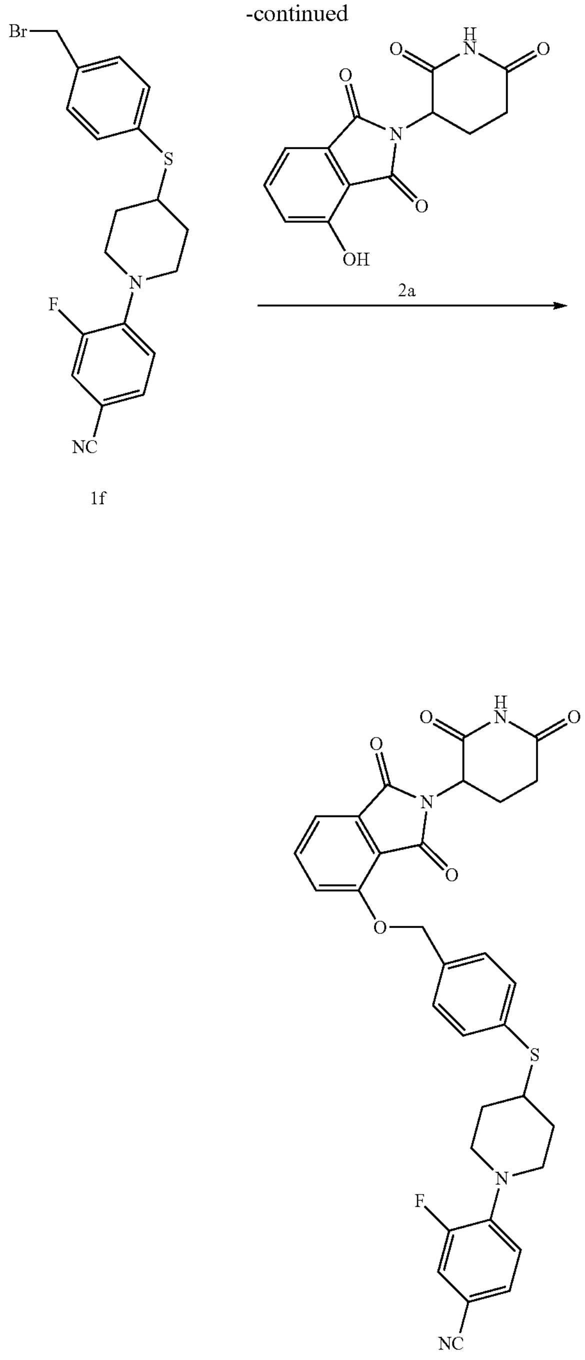

1f

2

2-(2,6-dioxopiperidin-3-yl)-4-hydroxyisoindoline-1,3-dione 2a (30 mg, 0.113 mmol, Bide Pharmatech Ltd.) and anhydrous potassium carbonate (21 mg, 0.152 mmol) were added to N,N-dimethylacetamide (3 mL), followed by the addition of compound if (30 mg, 0.074 mmol), and the mixture was reacted for 16 h. The reaction solution was filtered and purified by high performance liquid chromatography (Waters 2767-SQ Detecor2, eluent system: 10 mmol/L aqueous ammonium bicarbonate solution and acetonitrile, gradient of acetonitrile: 55%-75%, flow rate: 30 mL/min) to give the title compound 2 (30 mg, yield: 68%).

MS m/z (ESI): 599.1 [M+1].

$^1$H NMR (500 MHz, DMSO-$d_6$) 11.13 (s, 1H), 7.84 (dd, 1H), 7.68 (dd, 1H), 7.60 (d, 1H), 7.55 (dd, 1H), 7.53-7.45 (m, 5H), 7.13 (t, 1H), 5.37 (s, 2H), 5.10 (dd, 1H), 3.60-3.44 (m, 3H), 3.06-2.82 (m, 3H), 2.65-2.55 (m, 1H), 2.54-2.45 (m, 1H), 2.10-1.95 (m, 3H), 1.68-1.54 (m, 2H).

Example 3

(S)-4-(4-((4-(((2-(2,6-dioxopiperidin-3-yl)-1-oxoisoindolin-4-yl)oxy)methyl)phenyl)thio)piperidin-1-yl)-3-fluorobenzonitrile 3

3

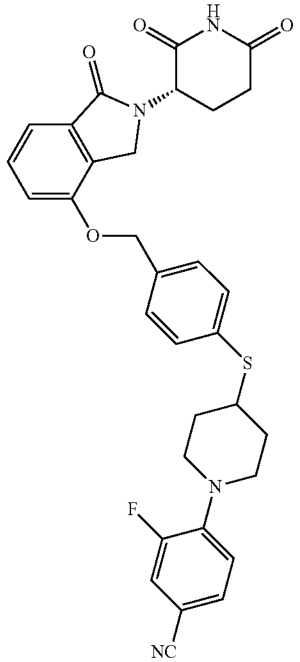

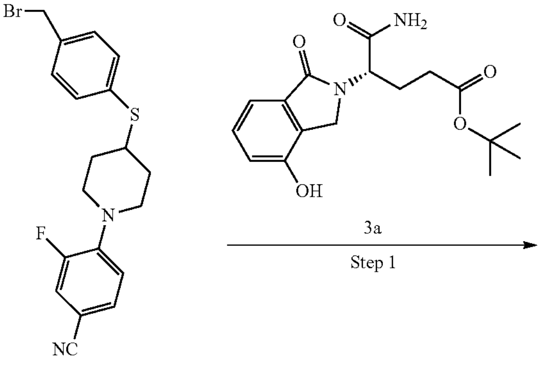

1f

-continued

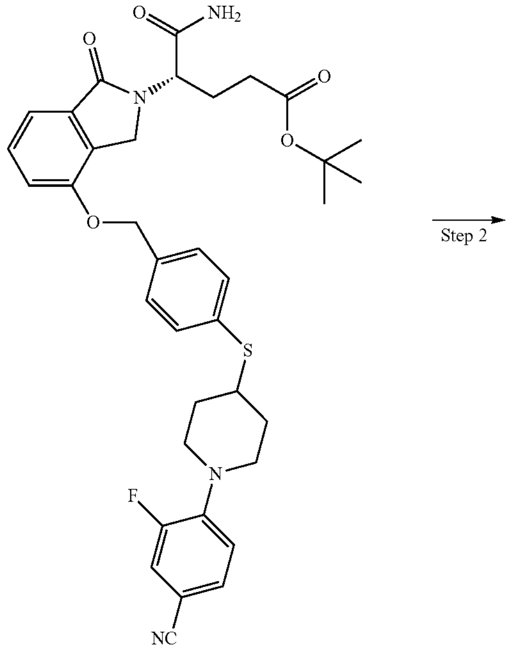

3b

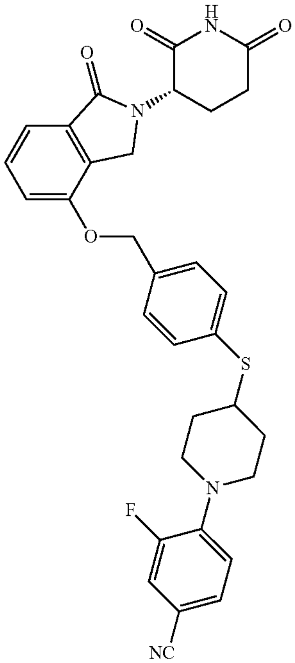

3

Step 1

Tert-butyl (S)-5-amino-4-(4-((4-((1-(4-cyano-2-fluorophenyl)piperidin-4-yl)thio)benzyl)oxy)-1-oxoisoindolin-2-yl)-5-oxopentanoate 3b Tert-butyl (S)-5-amino-4-(4-hydroxy-1-oxoisoindolin-2-yl)-5-oxopentanoate 3a (318 mg, 0.951 mmol, prepared by a known method described in "*Journal of Medicinal Chemistry,* 2020, 63 (13), 6648-6676") and anhydrous potassium carbonate (239 mg, 1.729 mmol) were added to N,N-dimethylacetamide (8 mL), followed by the addition of compound 1f (350 mg, 0.863 mmol), and the mixture was reacted for 16 h. The reaction solution was poured into ice water (20 mL), and the mixture was extracted with ethyl acetate (30 mL×3). The organic phases were combined, washed with a saturated sodium chloride solution (20 mL×2), dried over anhydrous sodium sulfate and filtered, and the filtrate was concentrated under reduced pressure. The residue was purified by column chromatography with an eluent system B to give the title compound 3b (500 mg, yield: 88%).

MS m/z (ESI): 659.2 [M+1].

Step 2

(S)-4-(4-((4-(((2-(2,6-dioxopiperidin-3-yl)-1-oxoisoindolin-4-yl)oxy)methyl)phenyl)thio)piperidin-1-yl)-3-fluorobenzonitrile 3

Compound 3b (500 mg, 0.758 mmol) was added to acetonitrile (30 mL), followed by the addition of p-toluenesulfonic acid monohydrate (187 mg, 0.983 mmol), and the mixture was stirred at 85° C. for 10 h. The reaction solution was concentrated under reduced pressure to remove the solvent, and water (20 mL) was added. The resulting mixture was extracted with ethyl acetate (30 mL×3). The organic phases were combined, washed sequentially with a saturated sodium bicarbonate solution (20 mL) and a saturated sodium chloride solution (20 mL), dried over anhydrous sodium sulfate and filtered, and the filtrate was concentrated under reduced pressure. The resulting residue was purified by high performance liquid chromatography (Waters 2767-SQ Detecor2, elution system: 10 mmol/L aqueous ammonium bicarbonate solution and acetonitrile, gradient of acetonitrile: 45%-60%, flow rate: 30 mL/min) to give the title compound 3 (30 mg, yield: 7%, ee: 99.6%). Chiral HPLC analysis: retention time 31.81 min, chiral purity: 99.6% (column: Chiralpak IE 150×4.6 mm, 5 μm; column temperature: 35° C., flow rate: 1.0 mL/min, mobile phase: n-hexane/ethanol/diethylamine=20/80/0.08 (v/v/v)).

MS m/z (ESI): 585.2 [M+1].

$^1$H NMR (500 MHz, DMSO-$d_6$) 10.98 (s, 1H), 7.68 (dd, 1H), 7.55 (dd, 1H), 7.52-7.43 (m, 5H), 7.37-7.28 (m, 2H), 7.13 (t, 1H), 5.25 (s, 2H), 5.12 (dd, 1H), 4.43 (d, 1H), 4.27 (d, 1H), 3.58-3.42 (m, 3H), 3.05-2.84 (m, 3H), 2.63-2.54 (m, 1H), 2.48-2.37 (m, 1H), 2.06-1.93 (m, 3H), 1.68-1.55 (m, 2H).

Example 4
(S)-4-(4-((4-(((2-(2,6-dioxopiperidin-3-yl)-1-oxoisoindolin-4-yl)oxy)methyl)-2-fluorophen yl)thio) piperidin-1-yl)-3-fluorobenzonitrile 4
4
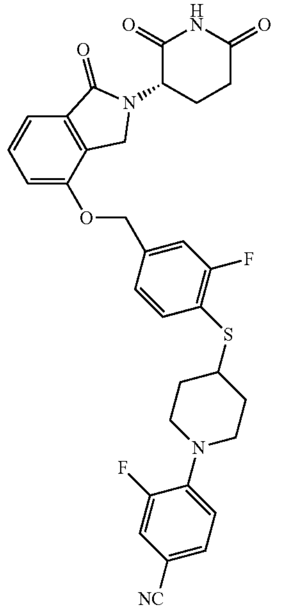
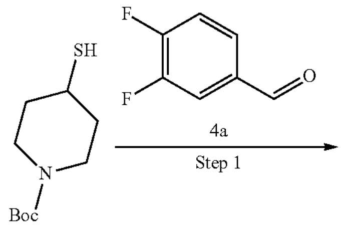
1a
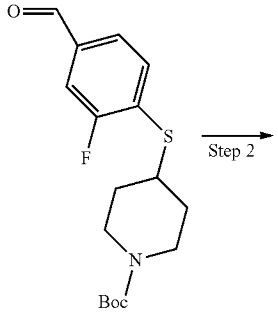
4b
-continued
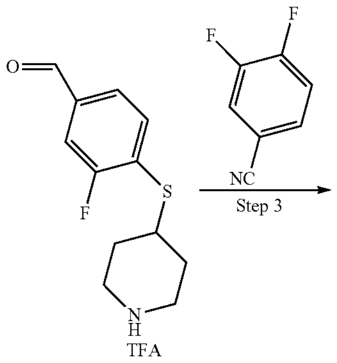
4c
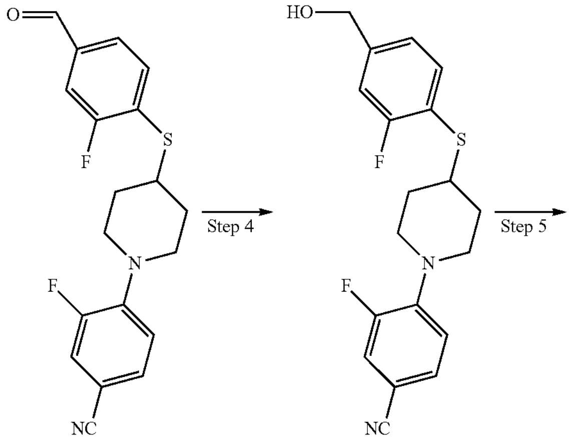
4d
4e
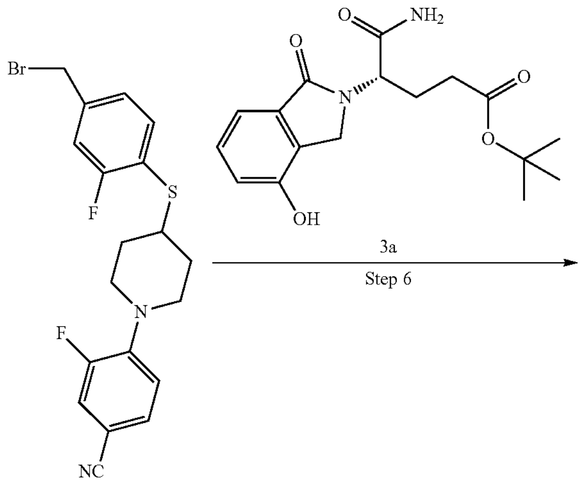
4f -continued

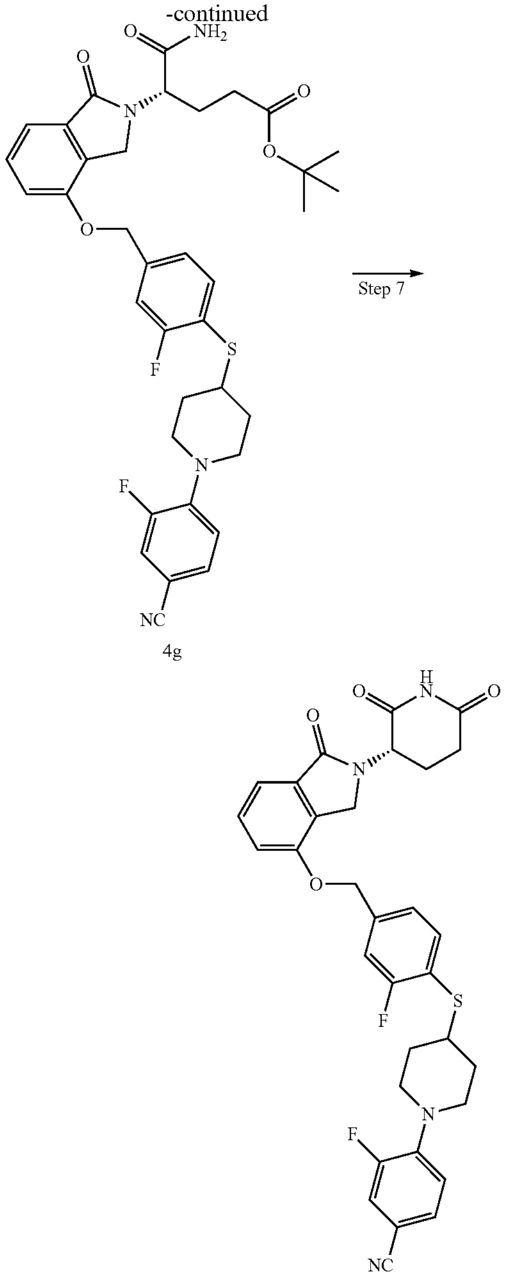

4g

4

Step 1

Tert-butyl 4-((2-fluoro-4-formylphenyl)thio)piperidine-1-carboxylate 4b

Compound 1a (600 mg, 2.76 mmol), 3,4-difluorobenzaldehyde 4a (470 mg, 3.3 mmol) and potassium carbonate (954 mg, 6.90 mmol) were added to N,N-dimethylformamide (12 mL). The mixture was heated to 80° C. and reacted for 2 h. The reaction solution was diluted with water (200 mL) and extracted with ethyl acetate (100 mL×3). The organic phases were combined, washed with a saturated sodium chloride solution (100 mL), dried over anhydrous sodium sulfate and filtered, and the filtrate was concentrated under reduced pressure. The residue was purified by column chromatography with an eluent system B to give the title compound 4b (920 mg, yield: 98%).

MS m/z (ESI): 283.9 [M−55].

Step 2

3-fluoro-4-(piperidin-4-ylthio)benzaldehyde Trifluoroacetate 4c

Compound 4b (920 mg, 2.71 mmol) was dissolved in dichloromethane (10 mL), and trifluoroacetic acid (2 mL) was slowly added under an ice bath. The mixture was reacted for 1 h. The reaction solution was concentrated and dried to give the title compound 4c (crude product), which was directly used in the next step without purification.

MS m/z (ESI): 239.9 [M+1].

Step 3

3-fluoro-4-(4-((2-fluoro-4-formylphenyl)thio)piperidin-1-yl)benzonitrile 4d

Compound 4c (960 mg, 2.72 mmol), 3,4-difluorobenzonitrile (756 mg, 5.43 mmol; Bide Pharmatech Ltd.) and potassium carbonate (1.50 g, 10.86 mmol) were added to N,N-dimethylformamide (12 mL), and the mixture was heated to 80° C. and reacted overnight. The reaction solution was added with water (50 mL) and extracted with ethyl acetate (30 mL×3). The organic phases were combined, washed with a saturated sodium chloride solution (50 mL×3), dried over anhydrous sodium sulfate and filtered, and the filtrate was concentrated. The resulting residue was purified by column chromatography with an eluent system B to give the title compound 4d (890 mg, yield: 91%).

MS m/z (ESI): 358.9 [M+1].

Step 4

3-fluoro-4-(4-((2-fluoro-4-(hydroxymethyl)phenyl)thio)piperidin-1-yl)benzonitrile 4e Compound 4d (260 mg, 0.725 mmol) was added to methanol (8 mL) under an ice bath, followed by the addition of sodium borohydride (55 mg, 1.45 mmol), and the mixture was stirred for 1 h under an ice bath. The reaction was quenched with a saturated ammonium chloride solution (10 mL), and the reaction solution was extracted with ethyl acetate (30 mL×3). The organic phases were combined, washed with a saturated sodium chloride solution (30 mL), dried over anhydrous sodium sulfate and filtered, and the filtrate was concentrated under reduced pressure. The residue was purified by column chromatography with an eluent system B to give the title compound 4e (250 mg, yield: 96%).

MS m/z (ESI): 360.9 [M+1].

Step 5

4-(4-((4-(bromomethyl)-2-fluorophenyl)thio)piperidin-1-yl)-3-fluorobenzonitrile 4f Compound 4e (250 mg, 0.694 mmol) was added to dichloromethane (5 mL), followed by the sequential addition of triphenylphosphine (237 mg, 0.901 mmol) and carbon tetrabromide (299 mg, 0.901 mmol), and the mixture was reacted for 1 h. The reaction solution was concentrated.

The residue was purified by column chromatography with an eluent system B to give the title compound 4f (130 mg, yield: 44%).

MS m/z (ESI): 423.0 [M+1]; 425.0 [M+3].

Step 6

Tert-butyl (S)-5-amino-4-(4-((4-(((1-(4-cyano-2-fluorophenyl) piperidin-4-yl)thio)-3-fluorobenzyl)oxy)-1-oxoisoindolin-2-yl)-5-oxopentanoate 4g Compound 3a (56 mg, 0.169 mmol) and anhydrous potassium carbonate (42 mg, 0.307 mmol) were added to N,N-dimethylformamide (3 mL), followed by the addition of compound 4f (65 mg, 0.153 mmol), and the mixture was reacted for 1 h. The reaction solution was poured into ice water (20 mL), and the resulting mixture was extracted with ethyl acetate (30 mL×3). The organic phases were combined, washed with a saturated sodium chloride solution (20 mL×2), dried over anhydrous sodium sulfate and filtered, and the filtrate was concentrated under reduced pressure. The residue was purified by column chromatography with an eluent system B to give the title compound 4g (95 mg, yield: 91%).

MS m/z (ESI): 677.0 [M+1].

Step 7

(S)-4-(4-((4-(((2-(2,6-dioxopiperidin-3-yl)-1-oxoisoindolin-4-yl)oxy)methyl)-2-fluorophen yl)thio) piperidin-1-yl)-3-fluorobenzonitrile 4

Compound 4g (50 mg, 0.074 mmol) was added to acetonitrile (6 mL), followed by the addition of benzenesulfonic acid (17 mg, 0.096 mmol) at room temperature, and the mixture was reacted at 80° C. for 12 h. The reaction solution was concentrated under reduced pressure to remove the solvent. The resulting residue was purified by high performance liquid chromatography (Waters 2767-SQ Detecor2, elution system: one-thousandth volume of aqueous trifluoroacetic acid solution and acetonitrile, gradient of acetonitrile: 50%-67%, flow rate: 30 mL/min) to give the title compound 4 (13 mg, yield: 29%).

MS m/z (ESI): 603.2 [M+1].

$^1$H NMR (500 MHz, DMSO-$d_6$) δ 10.99 (s, 1H), 7.69 (dd, 1H), 7.62-7.53 (m, 2H), 7.50 (t, 1H), 7.43 (dd, 1H), 7.39-7.27 (m, 3H), 7.13 (t, 1H), 5.28 (s, 2H), 5.13 (dd, 1H), 4.46 (d, 1H), 4.30 (d, 1H), 3.53-3.48 (m, 3H), 3.01-2.88 (m, 3H), 2.65-2.56 (m, 1H), 2.46-2.41 (m, 1H), 2.03-1.96 (m, 3H), 1.67-1.57 (m, 2H).

Example 5

(S)-4-(4-((4-(((2-(2,6-dioxopiperidin-3-yl)-1-oxoisoindolin-4-yl)oxy)methyl)-3-fluorophen yl)thio) piperidin-1-yl)-3-fluorobenzonitrile 5

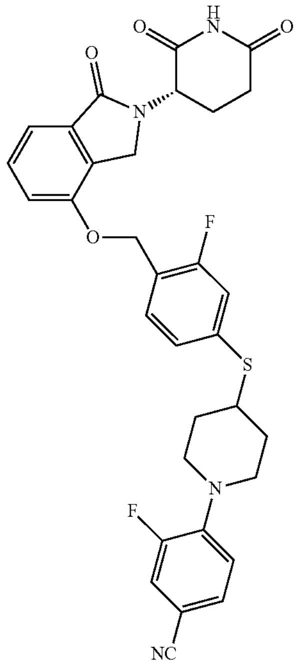

The title compound 5 (90 mg) was prepared by following the synthetic route for compound 4 in Example 4, with the starting compound 3,4-difluorobenzaldehyde replaced by the starting compound 2,4-difluorobenzaldehyde.

MS m/z (ESI): 603.1 [M+1].

$^1$H NMR (500 MHz, DMSO-$d_6$) δ 10.98 (s, 1H), 7.70 (dd, 1H), 7.60-7.48 (m, 3H), 7.42-7.31 (m, 3H), 7.27 (dd, 1H), 7.14 (t, 1H), 5.27 (s, 2H), 5.11 (dd, 1H), 4.39 (d, 1H), 4.23 (d, 1H), 3.68-3.62 (m, 1H), 3.56-3.49 (m, 2H), 3.01 (t, 2H), 2.95-2.87 (m, 1H), 2.61-2.54 (m, 1H), 2.46-2.41 (m, 1H), 2.02-1.94 (m, 3H), 1.70-1.59 (m, 2H).

Example 6
(S)-4-(4-((5-(((2-(2,6-dioxopiperidin-3-yl)-1-oxoisoindolin-4-yl)oxy)methyl)pyridin-2-yl)thio)piperidin-1-yl)-3-fluorobenzonitrile 6
6
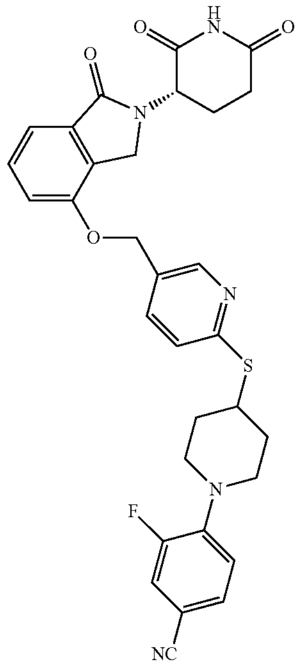
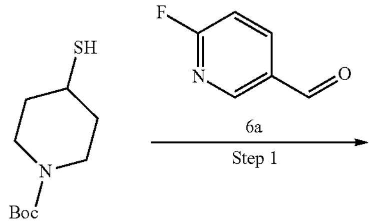
6a
1a
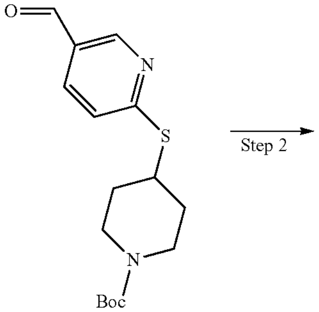
6b
-continued
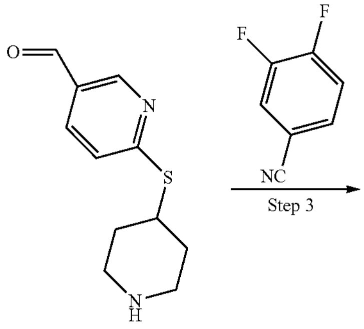
TFA
6c
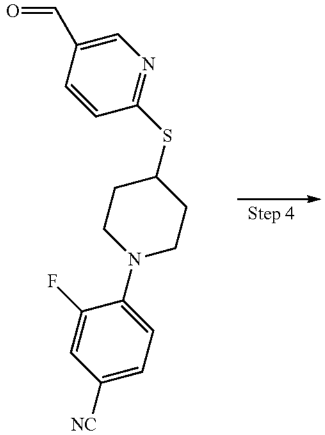
6d
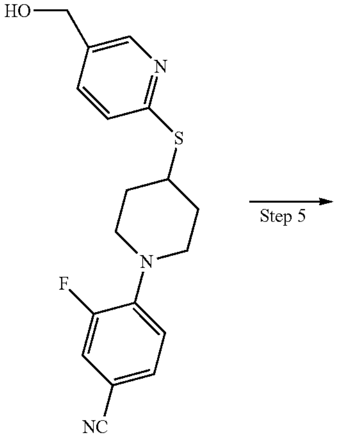
6e -continued

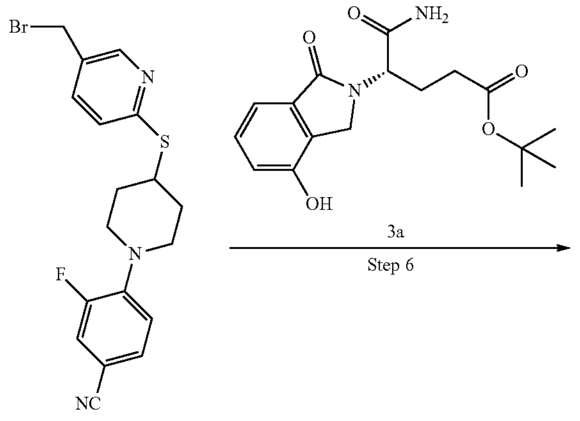

6f

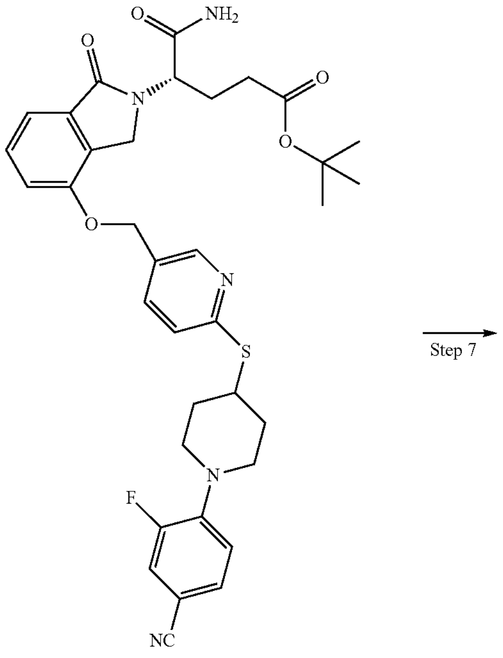

6g

-continued

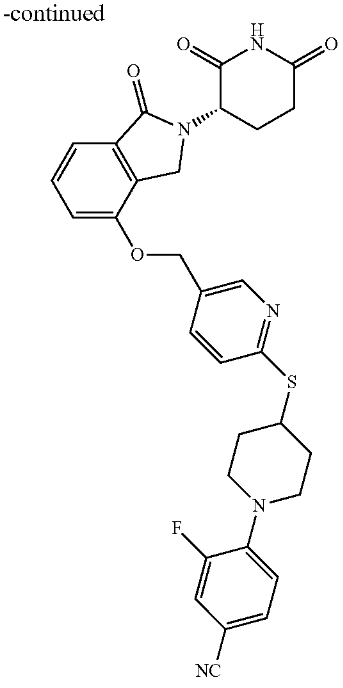

6

Step 1

Tert-butyl 4-((5-formylpyridin-2-yl)thio)piperidine-1-carboxylate 6b

Compound 1a (700 mg, 3.22 mmol), 6-fluoropyridine-3-carbaldehyde 6a (443 mg, 3.54 mmol) and potassium carbonate (1.11 g, 8.05 mmol) were added to N,N-dimethylformamide (10 mL). The mixture was heated to 80° C. and reacted for 1 h. The reaction solution was diluted with water (30 mL) and extracted with ethyl acetate (40 mL×3). The organic phases were combined, washed with a saturated sodium chloride solution (100 mL), dried over anhydrous sodium sulfate and filtered, and the filtrate was concentrated under reduced pressure. The residue was purified by column chromatography with an eluent system B to give the title compound 6b (1.0 g, yield: 96%).

MS m/z (ESI): 267.1 [M−55].

Step 2

6-(piperidin-4-ylthio)nicotinaldehyde Trifluoroacetate 6c

Compound 6b (950 mg, 2.95 mmol) was dissolved in dichloromethane (10 mL), and trifluoroacetic acid (2 mL) was slowly added under an ice bath. The mixture was reacted for 1 h. The reaction solution was concentrated and dried to give the title compound 6c (crude product), which was directly used in the next step without purification.

MS m/z (ESI): 223.1 [M+1].

Step 3

3-fluoro-4-(4-((5-formylpyridin-2-yl)thio)piperidin-1-yl)benzonitrile 6d

Compound 6c (760 mg, 2.94 mmol), 3,4-difluorobenzonitrile (817 mg, 5.87 mmol) and potassium carbonate (1.22 g, 8.81 mmol) were added to N,N-dimethylformamide (15 mL), and the mixture was heated to 80° C. and reacted overnight. The reaction solution was added with water (50 mL) and extracted with ethyl acetate (50 mL×3). The organic phases were combined, washed with a saturated sodium chloride solution (50 mL×3), dried over anhydrous sodium sulfate and filtered, and the filtrate was concentrated under reduced pressure. The resulting residue was purified by column chromatography with an eluent system B to give the title compound 6d (850 mg, yield: 84%).

MS m/z (ESI): 342.1 [M+1].

Step 4

3-fluoro-4-(4-((5-(hydroxymethyl)pyridin-2-yl)thio)piperidin-1-yl)benzonitrile 6e Compound 6d (600 mg, 1.76 mmol) was added to methanol (10 mL) under an ice bath, followed by the slow addition of sodium borohydride (133 mg, 3.51 mmol), and the mixture was reacted for 1 h. The reaction was quenched with water (10 mL), and the reaction solution was extracted with ethyl acetate (30 mL×3). The organic phases were combined, washed with a saturated sodium chloride solution (30 mL), dried over anhydrous sodium sulfate and filtered, and the filtrate was concentrated under reduced pressure. The residue was purified by column chromatography with an eluent system B to give the title compound 6e (580 mg, yield: 96%).

MS m/z (ESI): 344.1 [M+1].

Step 5

4-(4-((5-(bromomethyl)pyridin-2-yl)thio)piperidin-1-yl)-3-fluorobenzonitrile 6f

Compound 6e (200 mg, 0.582 mmol) was added to dichloromethane (6 mL), followed by the sequential addition of triphenylphosphine (199 mg, 0.757 mmol) and carbon tetrabromide (251 mg, 0.757 mmol), and the mixture was reacted for 2 h. The reaction solution was concentrated. The residue was purified by column chromatography with an eluent system B to give the title compound 6f (190 mg, yield: 80%).

MS m/z (ESI): 406.0 [M+1]; 408.0 [M+3].

Step 6

Tert-butyl (S)-5-amino-4-(4-((6-((1-(4-cyano-2-fluorophenyl)piperidin-4-yl)thio)pyridin-3-yl)methoxy)-1-oxoisoindolin-2-yl)-5-oxopentanoate 6g Compound 3a (82 mg, 0.246 mmol) and anhydrous potassium carbonate (65 mg, 0.468 mmol) were added to N,N-dimethylformamide (3 mL), followed by the addition of compound 6f (95 mg, 0.244 mmol), and the mixture was reacted for 2 h. The reaction solution was poured into ice water (10 mL), and the resulting mixture was extracted with ethyl acetate (30 mL×3). The organic phases were combined, washed with a saturated sodium chloride solution (20 mL×2), dried over anhydrous sodium sulfate and filtered, and the filtrate was concentrated under reduced pressure. The residue was purified by column chromatography with an eluent system B to give the title compound 6g (145 mg, yield: 94%).

MS m/z (ESI): 660.2 [M+1].

Step 7

(S)-4-(4-((5-(((2-(2,6-dioxopiperidin-3-yl)-1-oxoisoindolin-4-yl)oxy)methyl)pyridin-2-yl)thio)piperidin-1-yl)-3-fluorobenzonitrile 6

Compound 6g (60 mg, 0.091 mmol) was added to acetonitrile (5 mL), followed by the addition of benzenesulfonic acid (16 mg, 0.091 mmol) at room temperature, and the mixture was reacted at 80° C. for 8 h. The reaction solution was concentrated under reduced pressure to remove the solvent. The resulting residue was subjected to high performance liquid chromatography (Gilson GX-281, elution system: 10 mmol/L aqueous ammonium bicarbonate solution and acetonitrile, gradient of acetonitrile: 60%-80%, flow rate: 30 mL/min) to give the title compound 6 (42 mg, yield: 78%).

MS m/z (ESI): 586.4 [M+1].

$^1$H NMR (500 MHz, DMSO-$d_6$): δ 10.98 (s, 1H), 8.60 (s, 1H), 7.78 (dd, 1H), 7.69 (dd, 1H), 7.59-7.48 (m, 2H), 7.38-7.33 (m, 3H), 7.16 (t, 1H), 5.24 (s, 2H), 5.12 (dd, 1H), 4.42 (d, 1H), 4.26 (d, 1H), 4.07-3.99 (m, 1H), 3.56-3.48 (m, 2H), 3.13-3.03 (m, 2H), 2.96-2.87 (m, 1H), 2.63-2.55 (m, 1H), 2.46-2.38 (m, 1H), 2.21-2.12 (m, 2H), 2.02-1.94 (m, 1H), 1.82-1.70 (m, 2H).

Example 6'

(R)-4-(4-((5-(((2-(2,6-dioxopiperidin-3-yl)-1-oxoisoindolin-4-yl)oxy)methyl)pyridin-2-yl)thio)piperidin-1-yl)-3-fluorobenzonitrile 6'

6'

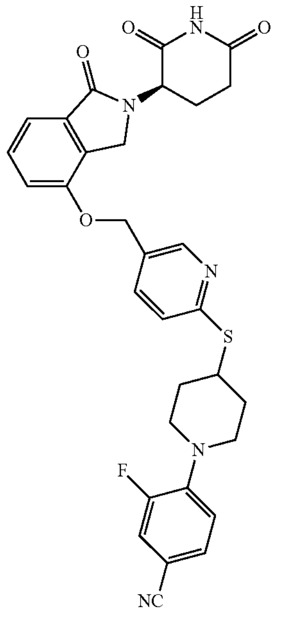

-continued

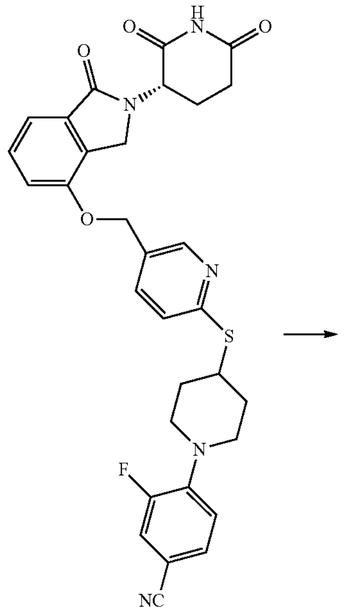

6

-continued

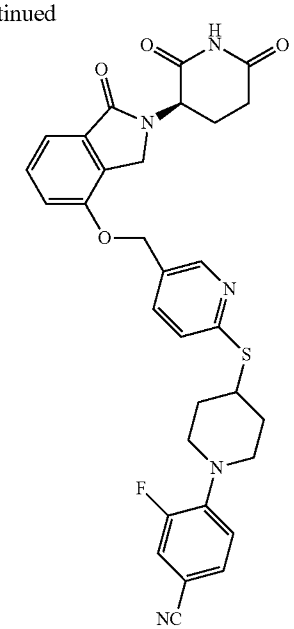

6'

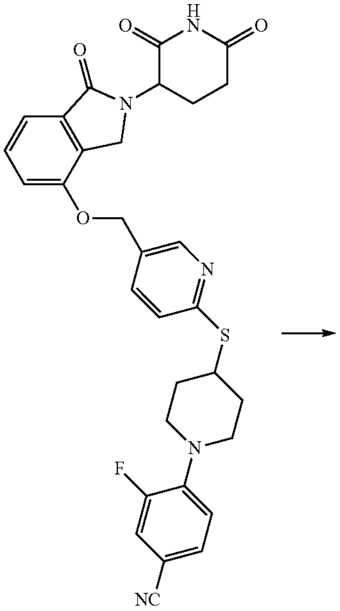

6'a

Compound 6 (500 mg, 0.853 mmol) was dissolved in tetrahydrofuran (30 mL), followed by the addition of a saturated aqueous sodium carbonate solution (30 mL). After the addition, the mixture was vigorously stirred for 1.5 h. The reaction solution was subjected to liquid separation. The organic phase was diluted with dichloromethane (120 mL), washed sequentially with a saturated ammonium chloride solution (20 mL) and a saturated sodium chloride solution (20 mL), dried over anhydrous sodium sulfate and filtered, and the filtrate was concentrated under reduced pressure to give the title compound 6'a (crude product, chiral HPLC showed a content of compound 6' of 42.8%).

The resulting crude 6'a was subjected to preparative chiral separation (separation conditions: chiral preparation column CHIRALPAK IE 20×250 mm (Daicel); mobile phase: n-hexane and ethanol, gradient of ethanol: 80%; flow rate: 20 mL/min), and the resulting preparation solution was concentrated under reduced pressure under a water bath at less than 20° C. to give the title compound 6' (25 mg, yield: 5.0%).

MS m/z (ESI): 586.1 [M+1].

Chiral HPLC analysis: retention time: 24.426 min, chiral purity: 100% (column: CHIRALPAK IE 150×4.6 mm, 5 μm; mobile phase: n-hexane/ethanol=20/80 (v/v))

$^1$H NMR (500 MHz, DMSO-$d_6$): 10.97 (s, 1H), 8.59 (s, 1H), 7.78 (dd, 1H), 7.68 (d, 1H), 7.56 (d, 1H), 7.50 (t, 1H), 7.35 (t, 3H), 7.15 (t, 1H), 5.24 (s, 2H), 5.11 (dd, 1H), 4.41 (d, 1H), 4.25 (d, 1H), 4.02 (t, 1H), 3.51 (d, 2H), 3.07 (t, 2H), 2.91 (ddd, 1H), 2.60-2.55 (m, 1H), 2.43 (dd, 1H), 2.20-2.12 (m, 2H), 1.99 (s, 1H), 1.76 (tt, 2H).

Example 7

(S)-4-(4-((5-(((2-(2,6-dioxopiperidin-3-yl)-1-oxoisoindolin-4-yl)oxy)methyl)pyrimidin-2-yl)thio)piperidin-1-yl)-3-fluorobenzonitrile 7

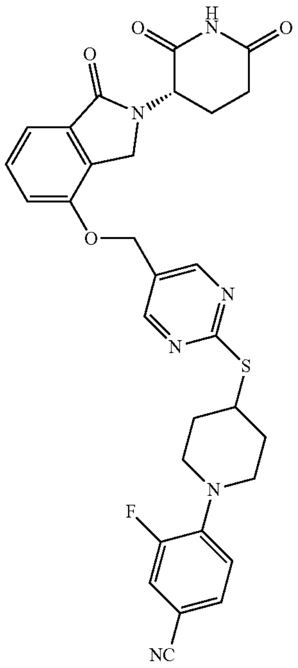

7

The title compound 7 (38 mg) was prepared by following the synthetic route for compound 4 in Example 4, with the starting compound 3,4-difluorobenzaldehyde replaced by the starting compound 2-chloropyrimidine-5-carbaldehyde.

MS m/z (ESI): 587.2 [M+1].

$^1$H NMR (500 MHz, DMSO-$d_6$): δ 10.97 (s, 1H), 8.82 (s, 2H), 7.70 (dd, 1H), 7.57 (dd, 1H), 7.53 (t, 1H), 7.38 (t, 2H), 7.17 (t, 1H), 5.26 (s, 2H), 5.12 (dd, 1H), 4.44 (d, 1H), 4.27 (d, 1H), 3.99-3.92 (m, 1H), 3.58-3.47 (m, 2H), 3.14-3.04 (m, 2H), 2.96-2.87 (m, 1H), 2.64-2.56 (m, 1H), 2.44-2.37 (m, 1H), 2.26-2.15 (m, 2H), 2.03-1.96 (m, 1H), 1.85-1.75 (m, 2H).

Example 8

(S)-4-(4-((5-(((2-(2,6-dioxopiperidin-3-yl)-6-fluoro-1-oxoisoindolin-4-yl)oxy)methyl)pyridin-2-yl)thio)piperidin-1-yl)-3-fluorobenzonitrile 8

8

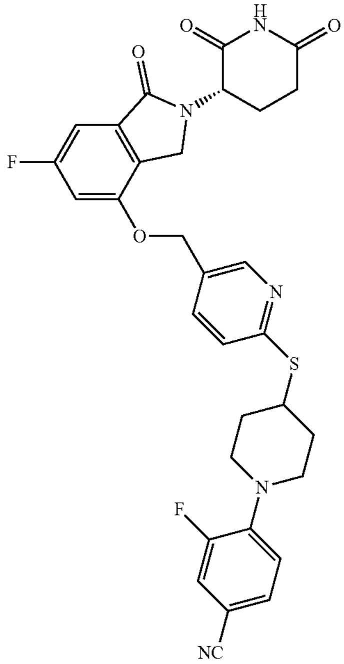

The title compound 8 (33 mg) was prepared by following the synthetic route for compound 4 in Example 4, with the starting compound 3,4-difluorobenzaldehyde replaced by the starting compound 2-fluoropyridine-5-carbaldehyde and compound 3a in step 6 replaced by tert-butyl (S)-5-amino-4-(6-fluoro-4-hydroxy-1-oxoisoindolin-2-yl)-5-oxopentanoate (prepared by the method disclosed in “Example 7 on page 99 of the description of the patent application WO2019040274A1”).

MS m/z (ESI): 604.1 [M+1].

$^1$H NMR (500 MHz, DMSO-d6): δ 10.99 (s, 1H), 8.60 (d, 1H), 7.78 (dd, 1H), 7.70 (dd, 1H), 7.57 (dd, 1H), 7.39-7.31 (m, 2H), 7.20-7.11 (m, 2H), 5.25 (s, 2H), 5.11 (dd, 1H), 4.40 (d, 1H), 4.23 (d, 1H), 4.09-3.98 (m, 1H), 3.58-3.46 (m, 2H), 3.13-3.02 (m, 2H), 2.96-2.83 (m, 1H), 2.63-2.55 (m, 1H), 2.46-2.34 (m, 1H), 2.21-2.12 (m, 2H), 2.04-1.93 (m, 1H), 1.82-1.68 (m, 2H).

Example 9

(S)-4-(4-((6-(((2-(2,6-dioxopiperidin-3-yl)-1-oxoisoindolin-4-yl)oxy)methyl)pyridin-3-yl)thio)piperidin-1-yl)-3-fluorobenzonitrile 9

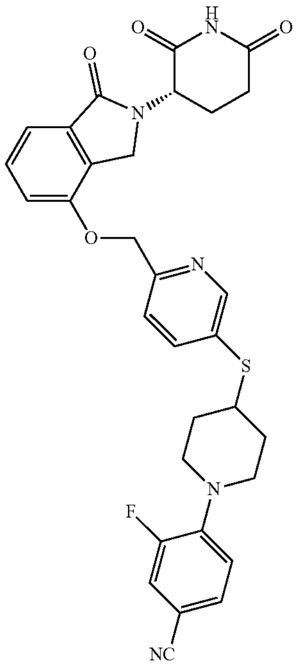

9

The title compound 9 (45 mg) was prepared by following the synthetic route for compound 4 in Example 4, with the starting compound 3,4-difluorobenzaldehyde replaced by the starting compound 5-fluoropyridine-2-carbaldehyde.

MS m/z (ESI): 586.3 [M+1].

$^1$H NMR (500 MHz, DMSO-$d_6$): δ 10.99 (s, 1H), 8.63 (d, 1H), 7.95 (dd, 1H), 7.68 (dd, 1H), 7.61-7.51 (m, 2H), 7.49 (t, 1H), 7.35 (d, 1H), 7.32 (d, 1H), 7.13 (t, 1H), 5.33 (s, 2H), 5.13 (dd, 1H), 4.47 (d, 1H), 4.32 (d, 1H), 3.65-3.45 (m, 3H), 3.05-2.85 (m, 3H), 2.68-2.55 (m, 1H), 2.44-2.35 (m, 1H), 2.07-1.93 (m, 3H), 1.71-1.55 (m, 2H).

Example 10

(S)-4-(4-((4-(((2-(2,6-dioxopiperidin-3-yl)-1-oxoisoindolin-4-yl)oxy)methyl)-2,3-difluorophenyl)thio)piperidin-1-yl)-3-fluorobenzonitrile 10

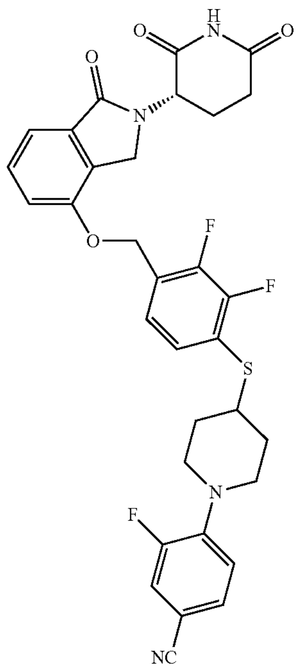

10

The title compound 10 (63 mg) was prepared by following the synthetic route for compound 4 in Example 4, with the starting compound 3,4-difluorobenzaldehyde replaced with the starting compound 2,3,4-trifluorobenzaldehyde.

MS m/z (ESI): 621.1 [M+1].

$^1$H NMR (500 MHz, DMSO-$d_6$): δ 10.98 (s, 1H), 7.69 (dd, 1H), 7.58-7.48 (m, 2H), 7.47-7.33 (m, 4H), 7.13 (t, 1H), 5.35 (s, 2H), 5.12 (dd, 1H), 4.40 (d, 1H), 4.25 (d, 1H), 3.67-3.46 (m, 3H), 3.06-2.82 (m, 3H), 2.64-2.56 (m, 1H), 2.46-2.37 (m, 1H), 2.07-1.90 (m, 3H), 1.73-1.56 (m, 2H).

Example 11

(S)-4-(4-((4-(((2-(2,6-dioxopiperidin-3-yl)-1-oxoisoindolin-4-yl)oxy)methyl)-2,5-difluorophenyl)thio)piperidin-1-yl)-3-fluorobenzonitrile 11

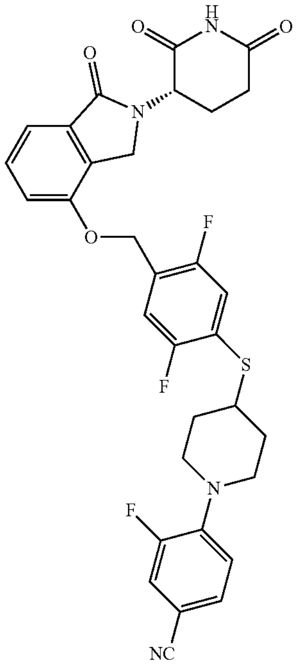

11

The title compound 11 (70 mg) was prepared by following the synthetic route for compound 4 in Example 4, with the starting compound 3,4-difluorobenzaldehyde replaced by the starting compound 2,4,5-trifluorobenzaldehyde.

MS m/z (ESI): 621.1 [M+1].

$^1$H NMR (500 MHz, DMSO-$d_6$): δ 10.98 (s, 1H), 7.89 (dd, 1H), 7.63-7.46 (m, 4H), 7.42-7.32 (m, 2H), 7.14 (t, 1H), 5.27 (s, 2H), 5.12 (dd, 1H), 4.42 (d, 1H), 4.27 (d, 1H), 3.72-3.61 (m, 1H), 3.58-3.46 (m, 2H), 3.07-2.96 (m, 2H), 2.95-2.83 (m, 1H), 2.65-2.56 (m, 1H), 2.44-2.38 (m, 1H), 2.09-1.90 (m, 3H), 1.74-1.58 (m, 2H).

Example 12

(S)-4-(4-((4-(((2-(2,6-dioxopiperidin-3-yl)-1-oxoisoindolin-4-yl)oxy)methyl)-2,6-difluorophenyl)thio)piperidin-1-yl)-3-fluorobenzonitrile 12

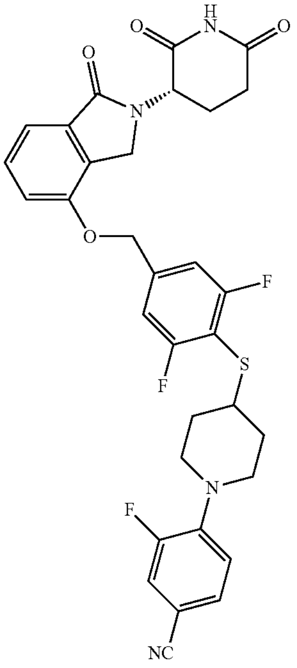

12

The title compound 12 (20 mg) was prepared by following the synthetic route for compound 4 in Example 4, with the starting compound 3,4-difluorobenzaldehyde replaced by the starting compound 3,4,5-trifluorobenzaldehyde.

MS m/z (ESI): 621.1 [M+1].

$^1$H NMR (500 MHz, DMSO-$d_6$): δ 10.99 (s, 1H), 7.67 (dd, 1H), 7.54 (dd, 1H), 7.50 (t, 1H), 7.43-7.33 (m, 3H), 7.29 (d, 1H), 7.11 (t, 1H), 5.31 (s, 2H), 5.13 (dd, 1H), 4.50 (d, 1H), 4.34 (d, 1H), 3.58-3.42 (m, 2H), 3.40-3.34 (m, 1H), 3.01-2.84 (m, 3H), 2.68-2.55 (m, 1H), 2.46-2.35 (m, 1H), 2.05-1.85 (m, 3H), 1.65-1.52 (m, 2H).

Example 13

(S)-4-(4-((5-(((2-(2,6-dioxopiperidin-3-yl)-1-oxoisoindolin-4-yl)oxy)methyl)-6-methylpyridin-2-yl)thio)piperidin-1-yl)-3-fluorobenzonitrile 13

13

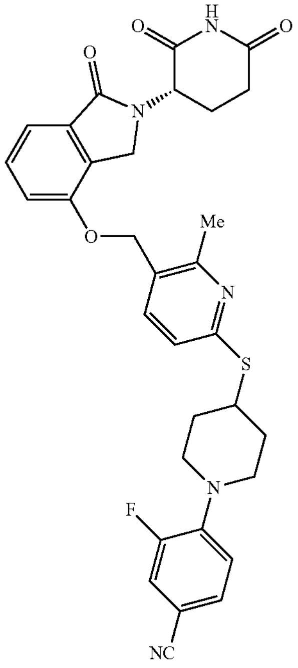

The title compound 13 (60 mg) was prepared by following the synthetic route for compound 4 in Example 4, with the starting compound 3,4-difluorobenzaldehyde replaced by the starting compound 6-fluoro-2-methyl-3-pyridinecarboxaldehyde.

MS m/z (ESI): 600.2 [M+1].

$^1$H NMR (500 MHz, DMSO-$d_6$): δ 10.97 (s, 1H), 7.78-7.63 (m, 2H), 7.61-7.47 (m, 2H), 7.44-7.30 (m, 2H), 7.24-7.07 (m, 2H), 5.24 (s, 2H), 5.11 (dd, 1H), 4.41 (d, 1H), 4.25 (d, 1H), 4.06-3.92 (m, 1H), 3.60-3.43 (m, 2H), 3.14-3.02 (m, 2H), 2.97-2.83 (m, 1H), 2.68-2.56 (m, 1H), 2.52 (s, 3H), 2.48-2.37 (m, 1H), 2.22-2.11 (m, 2H), 2.04-1.93 (m, 1H), 1.83-1.68 (m, 2H).

Example 14

(S)-4-(4-((2-chloro-4-(((2-(2,6-dioxopiperidin-3-yl)-1-oxoisoindolin-4-yl)oxy)methyl)phen yl)thio)piperidin-1-yl)-3-fluorobenzonitrile 14

14

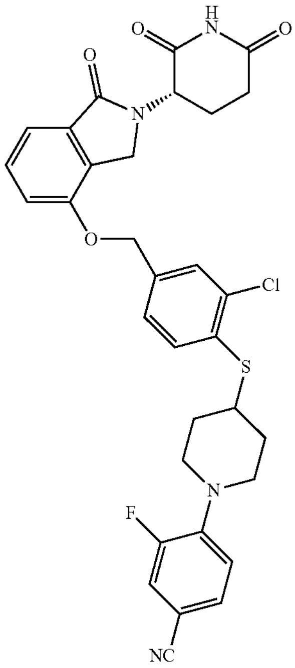

The title compound 14 (22 mg) was prepared by following the synthetic route for compound 4 in Example 4, with the starting compound 3,4-difluorobenzaldehyde replaced by the starting 3-chloro-4-fluorobenzaldehyde.

MS m/z (ESI): 618.9 [M+1].

$^1$H NMR (500 MHz, DMSO-$d_6$): δ 10.98 (s, 1H), 7.74-7.62 (m, 2H), 7.60 (d, 1H), 7.56 (dd, 1H), 7.53-7.44 (m, 2H), 7.35 (d, 1H), 7.32 (d, 1H), 7.14 (t, 1H), 5.25 (s, 2H), 5.12 (dd, 1H), 4.43 (d, 1H), 4.28 (d, 1H), 3.71-3.61 (m, 1H), 3.58-3.47 (m, 2H), 3.08-2.98 (m, 2H), 2.96-2.85 (m, 1H), 2.66-2.54 (m, 1H), 2.46-2.37 (m, 1H), 2.12-1.93 (m, 3H), 1.75-1.60 (m, 2H).

Example 15

4-(3-((5-(((2-((S)-2,6-dioxopiperidin-3-yl)-1-oxoisoindolin-4-yl)oxy)methyl)pyridin-2-yl)thio)pyrrolidin-1-yl)-3-fluorobenzonitrile 15

15

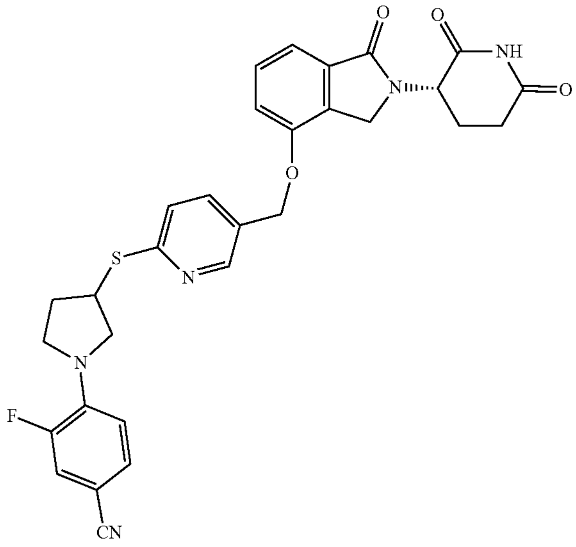

The title compound 15 (39 mg) was prepared by following the synthetic route for compound 4 in Example 4, with the starting compound 1a (tert-butyl 4-mercaptopiperidine-1-carboxylate) replaced by tert-butyl 3-mercaptopyrrolidine-1-carboxylate, and the starting compound 3,4-difluorobenzaldehyde replaced by the starting compound 2-fluoropyridine-5-carbaldehyde.

MS m/z (ESI): 572.3 [M+1].

$^1$H NMR (500 MHz, DMSO-$d_6$): δ 10.97 (s, 1H), 8.81 (d, 1H), 7.80 (dd, 1H), 7.58 (dd, 1H), 7.52 (t, 1H), 7.44 (dd, 1H), 7.42-7.32 (m, 3H), 6.79 (t, 1H), 5.25 (s, 2H), 5.11 (dd, 1H), 4.49-4.36 (m, 2H), 4.26 (d, 1H), 4.12-4.04 (m, 1H), 3.68-3.54 (m, 2H), 3.52-3.44 (m, 1H), 3.00-2.84 (m, 1H), 2.64-2.56 (m, 1H), 2.44-2.35 (m, 2H), 2.10-1.94 (m, 2H).

Example 16

(S)-4-(3-((4-(((2-(2,6-dioxopiperidin-3-yl)-1-oxoisoindolin-4-yl)oxy)methyl)phenyl)thio)azetidin-1-yl)-3-fluorobenzonitrile 16

16

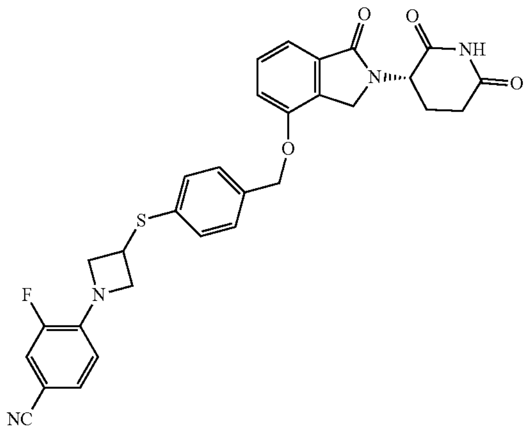

The title compound 16 (15 mg) was prepared by following the synthetic route for compound 4 in Example 4, with the starting compound 1a (tert-butyl 4-mercaptopiperidine-1-carboxylate) replaced by tert-butyl 3-mercaptoazetidine-1-carboxylate and the starting compound 3,4-difluorobenzaldehyde replaced by 4-fluorobenzaldehyde.

MS m/z (ESI): 557.0 [M+1].

$^1$H NMR (500 MHz, DMSO-$d_6$): δ 10.97 (s, 1H), 7.60 (dd, 1H), 7.54-7.42 (m, 4H), 7.37-7.27 (m, 4H), 6.62 (t, 1H), 5.24 (s, 2H), 5.12 (dd, 1H), 4.64-4.54 (m, 2H), 4.47-4.35 (m, 2H), 4.26 (d, 1H), 4.02-3.90 (m, 2H), 3.00-2.84 (m, 1H), 2.66-2.56 (m, 1H), 2.44-2.35 (m, 1H), 2.08-1.90 (m, 1H).

Example 17

(S)-4-(4-((5-(((2-(2,6-dioxopiperidin-3-yl)-1-oxoisoindolin-4-yl)oxy)methyl)-6-fluoropyridin-2-yl)thio)piperidin-1-yl)-3-fluorobenzonitrile 17

17

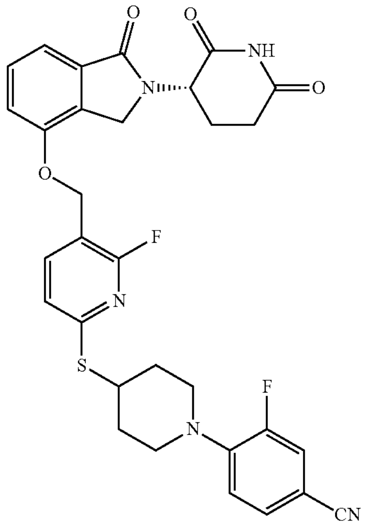

-continued
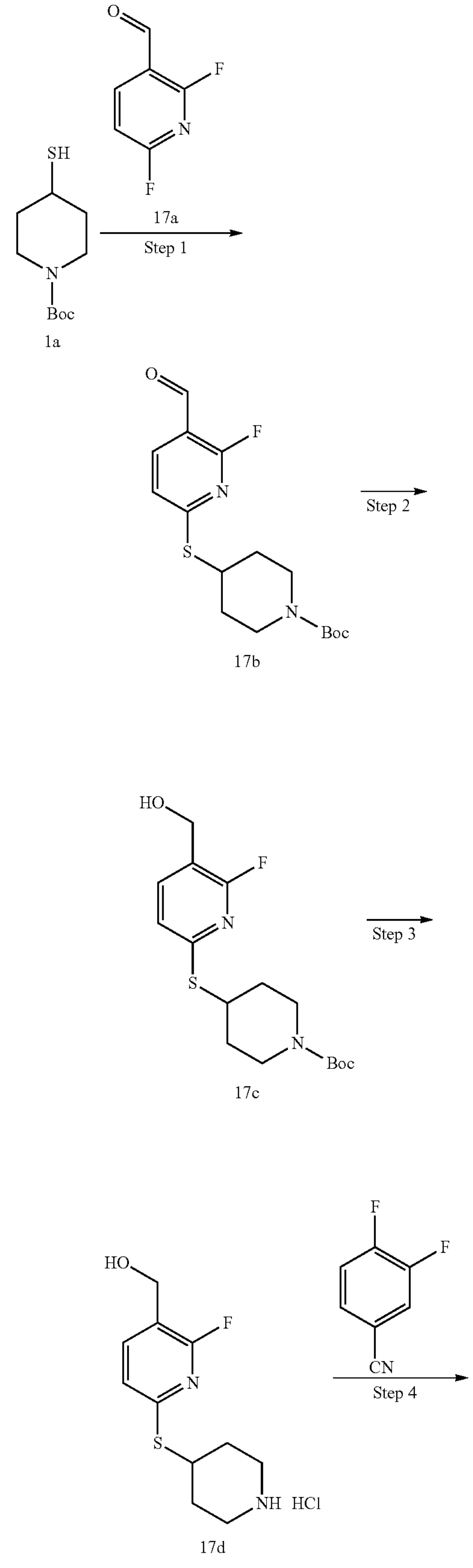
-continued
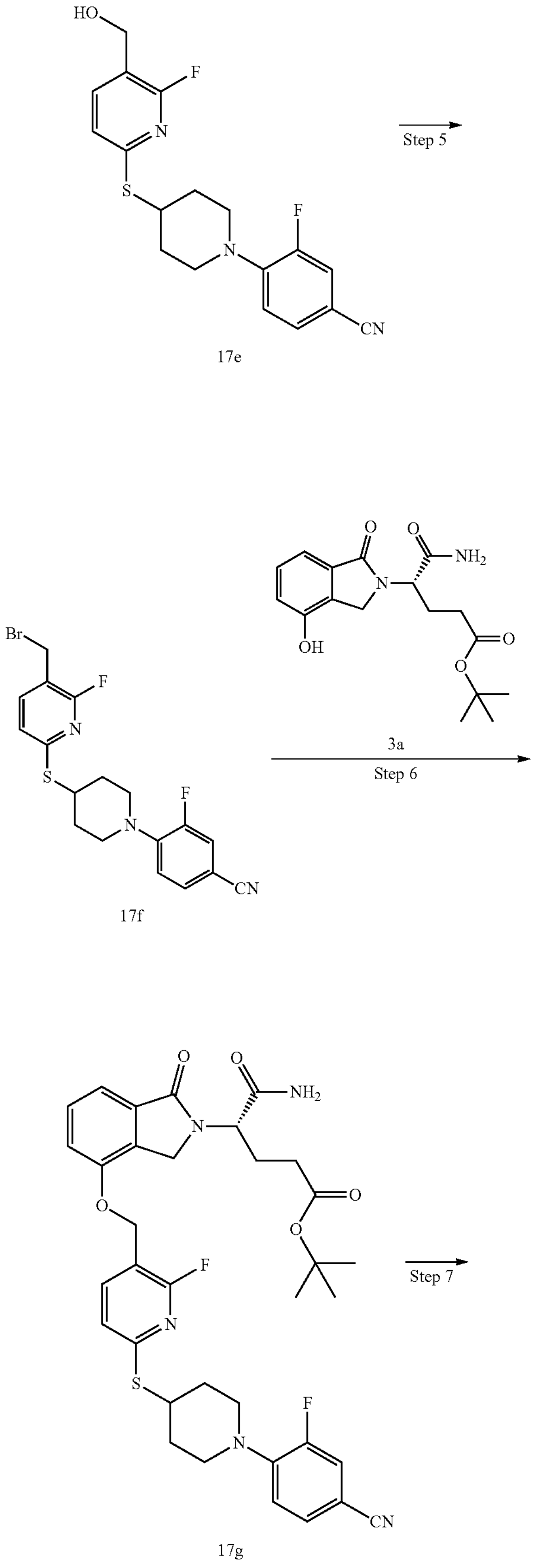

-continued

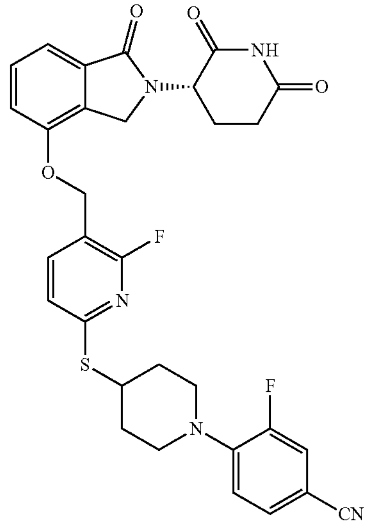

17

Step 1

Tert-butyl 4-((6-fluoro-5-formylpyridin-2-yl)thio) piperidine-1-carboxylate 17b

Compound 1a (1.5 g, 6.90 mmol), 2,6-difluoropyridine-3-carbaldehyde 17a (1.04 g, 7.27 mmol) and potassium carbonate (2.4 g, 17.36 mmol) were added to N,N-dimethylformamide (15 mL), and the mixture was reacted for 2 h. The reaction solution was diluted with water (200 mL) and extracted with ethyl acetate (100 mL×3). The organic phases were combined, washed with a saturated sodium chloride solution (100 mL), dried over anhydrous sodium sulfate and filtered, and the filtrate was concentrated under reduced pressure. The residue was purified by column chromatography with an eluent system B to give the title compound 17b (1.0 g, yield: 42%).

MS m/z (ESI): 285.0 [M−55].

Step 2

Tert-butyl 4-((6-fluoro-5-(hydroxymethyl)pyridin-2-yl)thio)piperidine-1-carboxylate 17c Compound 17b (1.0 g, 2.94 mmol) was dissolved in a mixed solvent of tetrahydrofuran (20 mL) and methanol (2 mL), followed by the slow addition of sodium borohydride (223 mg, 5.90 mmol) under an ice bath, and the mixture was reacted for 2 h. The reaction was quenched with water (50 mL), and the reaction solution was extracted with ethyl acetate (30 mL×3). The organic phases were combined, washed with a saturated sodium chloride solution (50 mL), dried over anhydrous sodium sulfate and filtered, and the filtrate was concentrated under reduced pressure. The residue was purified by column chromatography with an eluent system B to give the title compound 17c (910 mg, yield: 90%).

MS m/z (ESI): 287.0 [M−55].

Step 3

(2-fluoro-6-(piperidin-4-ylsulfanyl)pyridin-3-yl) methanol Hydrochloride 17d

Compound 17c (910 mg, 2.66 mmol) was dissolved in dichloromethane (10 mL), followed by the addition of a solution of 4 M hydrogen chloride in 1,4-dioxane (3 mL, 12 mmol), and the mixture was reacted for 1 h. The reaction solution was concentrated and dried to give the title compound 17d (625 mg), which was directly used in the next step.

MS m/z (ESI): 243.1 [M+1].

Step 4

3-fluoro-4-(4-((6-fluoro-5-(hydroxymethyl)pyridin-2-yl)thio)piperidin-1-yl)benzonitrile 17e Compound 17d (625 mg, 2.24 mmol) was added to N,N-dimethylformamide (20 mL), followed by the addition of 3,4-difluorobenzonitrile (312 mg, 2.24 mmol) and potassium carbonate (930 mg, 6.73 mmol), and the mixture was heated to 80° C. and reacted for 2 h. The reaction solution was diluted with water (100 mL) and extracted with ethyl acetate (100 mL×3). The organic phases were combined, washed with a saturated sodium chloride solution (100 mL), dried over anhydrous sodium sulfate and filtered and concentrated. The resulting residue was purified by column chromatography with an eluent system B to give the title compound 17e (400 mg, yield: 50%).

MS m/z (ESI): 362.0 [M+1].

Step 5

4-(4-((5-(bromomethyl)-6-fluoropyridin-2-yl)thio) piperidin-1-yl)-3-fluorobenzonitrile 17f Compound 17e (310 mg, 0.86 mmol) was added to dichloromethane (10 mL), followed by the addition of triphenylphosphine (360 mg, 1.37 mmol) and carbon tetrabromide (455 mg, 1.37 mmol), and the mixture was reacted for 12 h. The reaction solution was diluted with water (50 mL) and extracted with dichloromethane (30 mL×3). The organic phases were combined, washed with a saturated sodium chloride solution (50 mL), dried over anhydrous sodium sulfate and filtered, and the filtrate was concentrated under reduced pressure. The resulting residue was purified by column chromatography with an eluent system B to give the title compound 17f (340 mg, yield: 93%).

MS m/z (ESI): 423.9 [M+1].

Step 6

Tert-butyl (S)-5-amino-4-(4-((6-((1-(4-cyano-2-fluorophenyl) piperidin-4-yl)thio)-2-fluoropyridin-3-yl) methoxy)-1-oxoisoindolin-2-yl)-5-oxopentanoate 17g Compound 3a (268 mg, 0.80 mmol) and anhydrous potassium carbonate (223 mg, 1.61 mmol) were added to N,N-dimethylformamide (10 mL), followed by the addition of compound 17f (340 mg, 0.80 mmol), and the mixture was reacted for 1 h. The reaction solution was poured into ice water (20 mL), and the resulting mixture was extracted with ethyl acetate (30 mL×3). The organic phases were combined, washed with a saturated sodium chloride solution (20 mL×2), dried over anhydrous sodium sulfate and filtered, and the filtrate was concentrated under reduced pressure. The residue was purified by column chromatography with an eluent system B to give the title compound 17g (540 mg, yield: 99%).

MS m/z (ESI): 678.2 [M+1].

Step 7

(S)-4-(4-((5-(((2-(2,6-dioxopiperidin-3-yl)-1-oxoisoindolin-4-yl)oxy)methyl)-6-fluoropyridin-2-yl)thio)piperidin-1-yl)-3-fluorobenzonitrile 17

Compound 17g (540 mg, 0.80 mmol) was added to acetonitrile (20 mL), followed by the addition of benzenesulfonic acid (252 mg, 1.59 mmol) at room temperature, and the mixture was reacted at 80° C. for 12 h. The reaction solution was concentrated under reduced pressure to remove the solvent. The resulting residue was subjected to high performance liquid chromatography (Waters 2545-SQ Detecor2, elution system: 10 mmol/L aqueous ammonium bicarbonate solution and acetonitrile, gradient of acetonitrile: 53%-95%, flow rate: 30 mL/min) to give the title compound 4 (270 mg, yield: 56%).

MS m/z (ESI): 604.0 [M+1].

$^1$H NMR (500 MHz, DMSO-$d_6$) δ 10.98 (s, 1H), 8.01 (t, 1H), 7.70 (dd, 1H), 7.57 (dd, 1H), 7.52 (t, 1H), 7.43-7.30 (m, 3H), 7.17 (t, 1H), 5.25 (s, 2H), 5.12 (dd, 1H), 4.39 (d, 1H), 4.24 (d, 1H), 4.00-3.88 (m, 1H), 3.58-3.45 (m, 2H), 3.16-3.04 (dd, 2H), 2.98-2.84 (m, 1H), 2.66-2.55 (m, 1H), 2.48-2.35 (m, 1H), 2.23-2.12 (m, 2H), 2.08-1.92 (m, 1H), 1.82-1.70 (m, 2H).

Example 18

(S)-4-(44(4-(((2-(2,6-dioxopiperidin-3-yl)-1-oxoisoindolin-4-yl)oxy)methyl)-3,5-difluorophenyl)thio)piperidin-1-yl)-3-fluorobenzonitrile 18

18

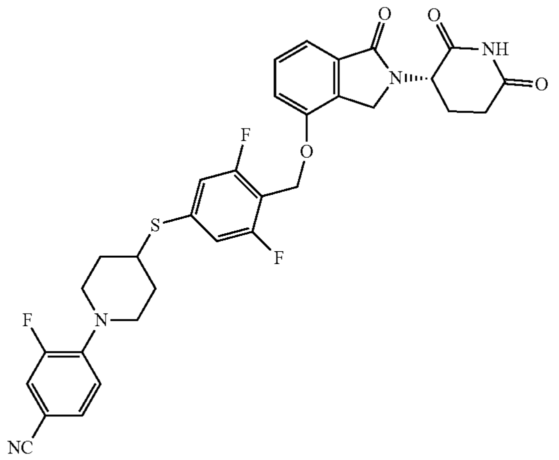

The title compound 18 (27 mg) was prepared by following the synthetic route for compound 17 in Example 17, with the starting compound 2,6-difluoropyridine-3-carbaldehyde replaced by the starting compound 2,4,6-trifluorobenzaldehyde.

MS m/z (ESI): 621.0 [M+1].

$^1$H NMR (500 MHz, DMSO-$d_6$): δ 10.95 (s, 1H), 7.70 (dd, 1H), 7.59-7.51 (m, 2H), 7.45 (d, 1H), 7.38 (d, 1H), 7.27 (d, 2H), 7.16 (t, 1H), 5.24 (dd, 2H), 5.09 (dd, 1H), 4.32 (d, 1H), 4.16 (d, 1H), 3.86-3.73 (m, 1H), 3.60-3.47 (m, 2H), 3.13-3.00 (m, 2H), 2.96-2.82 (m, 1H), 2.62-2.53 (m, 1H), 2.44-2.34 (m, 1H), 2.17-2.04 (m, 2H), 2.01-1.90 (m, 1H), 1.75-1.60 (m, 2H).

Biological Evaluation

Test Example 1. Biological Evaluation of NCI-H929 Proliferation Experiment

The following method was used to determine the inhibitory activity of the compounds of the present disclosure on the proliferation of NCI-H929 cells. The experimental method was briefly described as follows.

NCI-H929 cells (ATCC, CRL-9068) were cultured in a complete medium (RPMI 1640 medium (Hyclone, SH30809.01) containing 10% fetal bovine serum (Corning, 35-076-CV) and 0.05 mM 2-mercaptoethanol (Sigma, M3148)). On the first day of the experiment, NCI-H929 cells were seeded in a 96-well plate at a density of 6000 cells/well with a complete medium to form 100 μL of cell suspension per well, and 10 μL of test compound prepared in a complete medium and diluted in a gradient was added to each well. The compound was firstly dissolved in DMSO, with an initial concentration of 10 mM, and then subjected to serial dilution at a 5-fold concentration gradient for a total of 9 concentration points, with a blank control of 100% DMSO. Another 5 μL of the compound dissolved in DMSO was added to 95 μL of complete medium, i.e., the compound was diluted 20-fold with the complete medium. Finally the compound diluted in the complete medium at 10 μL/well was added to the cell suspension, wherein the final concentrations of the compound were 9 concentration points obtained by 5-fold gradient dilution starting from 50 μM. A blank control containing 0.5% DMSO was set. The plate was incubated in a cell incubator at 37° C. with 5% $CO_2$ for 5 days. On the sixth day, the 96-well cell culture plate was taken out, added with a CellTiter-Glo® luminescent cell activity detect reagent (Promega, G7573) at 50 μL/well, left to stand at room temperature for 10 min, and read for the luminescence signal values using a multi-mode microplate reader (PerkinElmer, EnVision 2015). $IC_{50}$ values for the inhibitory activity of the compounds were calculated using Graphpad Prism software, with the results shown in Table 1.

TABLE 1

$IC_{50}$ values for the inhibition of proliferation of NCI-H929 cells by the compounds of the present disclosure

| Compound | $IC_{50}$ (nM) |
|---|---|
| 1 | 0.34 |
| 2 | 4.36 |
| 3 | 0.10 |
| 4 | 0.17 |
| 5 | 0.08 |
| 6 | 0.02 |
| 7 | 0.13 |
| 8 | 0.28 |
| 9 | 0.90 |
| 10 | 0.18 |
| 11 | 0.22 |
| 12 | 0.61 |
| 13 | 1.78 |

TABLE 1-continued

| IC$_{50}$ values for the inhibition of proliferation of NCI-H929 cells by the compounds of the present disclosure | |
|---|---|
| Compound | IC$_{50}$ (nM) |
| 14 | 0.27 |
| 15 | 0.75 |
| 16 | 1.13 |
| 17 | 0.21 |
| 18 | 0.34 |

Conclusion: the compounds of the present disclosure have good inhibitory activity for the proliferation of NCI-H929 cells.

Test Example 2. Pharmacodynamic Test

1. Objective

This experiment was performed to evaluate the inhibition effect of the compound of Example 6 and the control example CC-92480 on the growth of human multiple myeloma cell NCI-H929 xenograft tumor in CB-17 SCID mice.

2. Test Compounds

Compound of Example 6;

control example CC-92480 (see compound 2 of WO2019014100A1, synthesized according to the method disclosed therein)

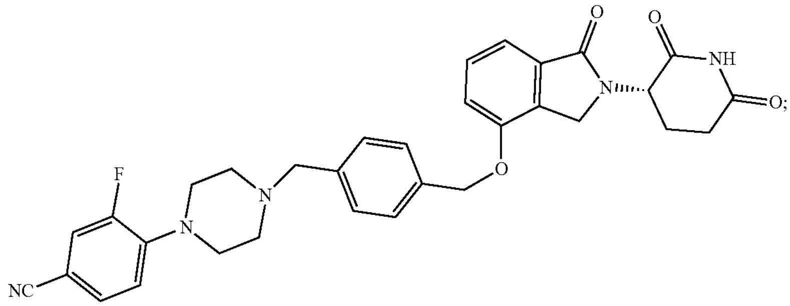 [SMILES: N#Cc1ccc(N2CCN(Cc3ccc(COc4cccc5c4CN([C@H]4CCC(=O)NC4=O)C5=O)cc3)CC2)c(F)c1]

;

Solutions of the compound of Example 6 and the control example CC-92480 were prepared with 5% DMSO+20% PEG400+70% (10% TPGS)+5% (1% HPMC K100LV).

3. Experimental Procedures and Materials 3.1 Experimental Animals and Housing Conditions Thirty CB-17 SCID female mice, purchased from Beijing Vital River Laboratory Animal Technology Co., Ltd. (certificate No. 20170011006049, SCXK (Shanghai) 2017-0011), weighing about 19 g at the time of purchase, were bred at 5 mice/cage (in 12/12 hour light/dark cycle, at a constant temperature of 23±1° C. and humidity of 50%-60%) and had free access to food and water.

3.2 Group of Animals:

After adaptive feeding, the CB-17 SCID mice were grouped as follows:

| Group | n | Route of administration |
|---|---|---|
| Vehicle control | 7 | 5% DMSO + 20% PEG400 + 70%(10% TPGS) + 5%(1% HPMC K100LV) (i.g/qd) |
| Example 6 | 7 | 1 mg/kg (i.g/qd) |
| CC-92480 | 7 | 1 mg/kg (i.g/qd) |

Note:
qd denotes once a day; i.g. denotes intragastric administration.

3.3 Procedures:

NCI-H929 cells in a logarithmic growth phase were inoculated subcutaneously into the right flank of 30 female CB-17 SCID mice at $5\times10^6$ cells/mouse/100 μL (containing 50 μL of Matrigel). After 10 days, when the tumor volume of the tumor-bearing mice reached about 200 $mm^3$, the mice were randomly divided into 3 groups according to the tumor volume and body weight: vehicle control group, CC-92480-1 mpk, compound of Example 6-1 mpk, with 7 mice in each group. The day of grouping was set as Day 0 (D0), and intragastric administration was performed once a day for 11 days (Table 2). For the tumor-bearing mice, the tumor volume was measured with a vernier caliper and the body weight was measured with a balance twice a week, and the data were recorded. The tumor-bearing animals were euthanized as the experimental endpoint when the tumor volume reached 2000 $mm^3$ or when most tumors showed rupture or when the tumor-bearing animals showed 20% of body weight loss.

3.4 Data Statistics

All data were plotted and statistically analyzed using Excel and GraphPad Prism 5 software.

The tumor volume (V) was calculated as follows: $V=\frac{1}{2}\times a\times b^2$, where a and b represent length and width, respectively.

The relative tumor proliferation rate T/C (%)=$(T-T_0)/(C-C_0)\times100$(%), where T and C are the tumor volume of animals at the end of the experiment in the treatment group and control group, respectively; $T_0$ and $C_0$ are the tumor volume of animals at the beginning of the experiment in the treatment group and control group, respectively.

Tumor growth inhibition TGI (%)=1−T/C (%), and when TGI (%) exceeds 100%, no specific value will be shown, and it is expressed only by >100%.

$$\text{Tumor regression } (\%)=[(T_0-T)/T_0]\times100(\%).$$

4. Results

The data on the efficacy of the compound of Example 6 and the control example CC-92480 on NCI-H929 xenograft tumor in CB-17 SCID mice are shown in Table 2 below and FIG. 1.

Figure 2:
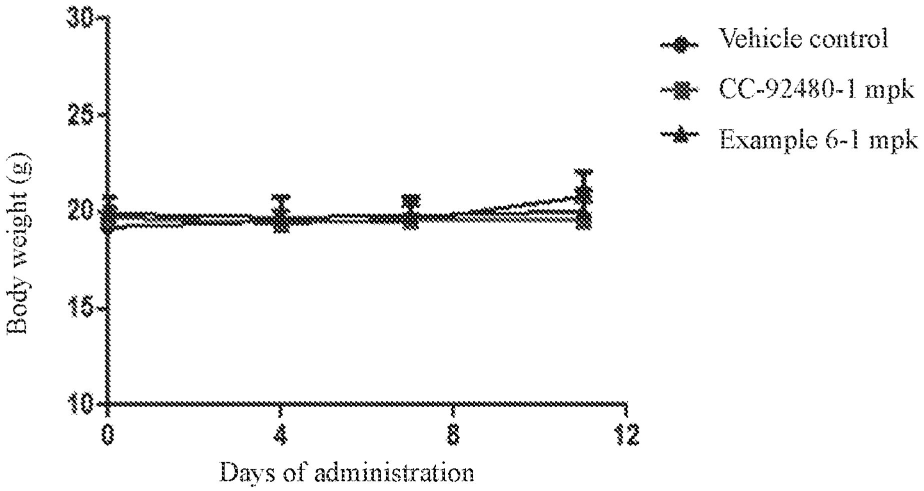
FIG. 2: effect of the compound of Example 6 and the control example CC-92480 on the body weight of CB-17 SCID mice.

The effect of the compound of Example 6 and the control example CC-92480 on the body weight of CB-17 SCID mice is shown in FIG. 2.

TABLE 2

Efficacy of the compound of the present disclosure on NCI-H929 xenograft tumor in CB-17 SCID mice

| Group | Route | of administration | Mean tumor volume ($mm^3$) D0 | SEM | D11 | SEM | % tumor regression D11 | p (vs. vehicle control) | Number of remaining animals/group |
|---|---|---|---|---|---|---|---|---|---|
| Vehicle control | qd/11d | po | 156.3 | 15.9 | 1711.7 | 190.1 | / | / | 7/7 |
| Example 6 | qd/11d | po | 155.4 | 16.5 | 18.6 | 1.8 | 88 | <0.001 | 7/7 |
| CC-92480 | qd/11d | po | 157.2 | 13.6 | 103.6 | 27.1 | 34 | <0.001 | 7/7 |

Note:
qd denotes once a day; po denotes oral administration.

5. Conclusion

The compound of Example 6 was administered once a day starting from 10 days after tumor cell transplantation, and significant tumor volume regressions occurred 11 days after administration. Upon calculation, the tumor inhibition rate is >100%, and the tumor regression rate is 88%. The statistical difference ($p<0.05$) is obtained when compared with an equal dose of CC-92480 at the end point of the experiment, and the administration has no influence on the body weight of mice. Under the same conditions, the tumor regression rate of the control example CC-92480 is 34%.

Test Example 3. Pharmacokinetic Evaluation

1. Overview

The drug concentration in the plasma of the test animals (mice) at different time points after intragastric administration of the compound of Example 6 and the control example CC-92480 was determined by an LC/MS/MS method. The pharmacokinetic behavior of the compound of the present disclosure in mice was studied and its pharmacokinetic profile was evaluated.

2. Test Protocol 2.1 Test Compounds

Compound of Example 6 and control example CC-92480.

2.2 Test Animals

Eighteen mice, female, purchased from Beijing Vital River Laboratory Animal Technology Co., Ltd., with animal production license number of SCXK (Shanghai) 2017-0005.

2.3 Preparation of Compound Solutions

A certain amount of compound of Example 6 was weighed, dissolved by adding 5% by volume of DMSO and 5% Tween 80 (Shanghai Titan Scientific Co., Ltd.), and then prepared into a 0.1 mg/mL clear solution by adding 90% normal saline.

A certain amount of the control example CC-92480 was weighed, dissolved by adding 5% by volume of DMSO and 5% Tween 80 (Shanghai Titan Scientific Co., Ltd.), and then prepared into a 0.1 mg/mL clear solution by adding 90% normal saline.

2.4 Administration

Nine mice were intragastrically administered with the compound of Example 6 at a dose of 2 mg/kg and at a volume of 0.2 mL/10 g.

Nine mice were intragastrically administered with the control example CC-92480 at a dose of 2 mg/kg and at a volume of 0.2 mL/10 g.

3. Procedures

Mice were intragastrically administered with the compound of Example 6 and the control example CC-92480, and 0.2 mL of blood was collected before the administration and 0.25 h, 0.5 h, 1.0 h, 2.0 h, 4.0 h, 6.0 h, 8.0 h, 11.0 h and 24.0 h after the administration (3 animals at each time point), placed in EDTA-K2 anticoagulation tubes, and centrifuged at 10,000 rpm for 1 min(4° C.). Plasma was separated within 1 h, and stored at −20° C. for testing. The process from blood collection to centrifugation was performed under an ice bath.

The content of the test compounds at different concentrations in mouse plasma after the administration was determined: 25 μL of mouse plasma at each time point after the administration was mixed with 50 μL (100 ng/mL) of internal standard solution camptothecin (National Institutes for Drug Control) and 175 μL of acetonitrile. The mixture was vortexed for 5 min and centrifuged for 10 min (3700 rpm/min), and 1 μL of the supernatant of the plasma sample was taken for LC/MS/MS assay (API4000 triple quadrupole tandem mass spectrometer, Applied Biosystems, USA; Shimadzu, LC-30AD ultra high performance liquid chromatography system, Shimadzu, Japan).

4. Pharmacokinetic Parameters

Pharmacokinetic parameters for the compound of the present disclosure are shown in Table 3 below.

TABLE 3

Pharmacokinetic parameters of the compound of the present disclosure

| No. | Pharmacokinetic experiment (2 mg/kg) Plasma concentration Cmax (ng/mL) | Area under curve AUC (ng/mL*h) | Half-life T½ (h) | Residence time MRT (h) | Clearance CL/F (mL/min/kg) | Apparent volume of distribution Vz/F (mL/kg) |
|---|---|---|---|---|---|---|
| Example 6 | 799 | 4686 | 2.9 | 4.6 | 7.1 | 1785 |
| CC-92480 | 692 | 1937 | 1.3 | 2.3 | 17.2 | 1961 |

Conclusion: The compound of the present disclosure demonstrates good absorption profile and has significant pharmacokinetic advantages.

Test Example 4. Evaluation of Plasma Stability of the Compound of the Present Disclosure 1. Abstract The stability of the compound of Example 6 and the control example CC-92480 after incubation in cryopreserved monkey plasma at 37° C. for 0 min, 15 min, 30 min, 60 min, 120 min, 180 min and 240 min was determined quantitatively by LC-MS/MS.

2. Test Protocol 2.1 Test Compounds

Compound of Example 6 and control example CC-92480.

2.2 Test Plasma

Monkey plasma was purchased from Shanghai Medicilon Inc.

2.3 Preparation of Compound Solutions

A certain amount of the compound of Example 6 was weighed and prepared with DMSO to obtain a 30 mM stock solution. A certain volume of the stock solution was diluted into a solution I at a concentration of 1600 μM with DMSO; and a certain volume of the solution I at 1600 μM was diluted with 50% methanol to obtain a working solution II at a concentration of 16 μM. A 30 mM stock solution, a 1600 μM solution I', and a 16 μM working solution II' of CC-92480 were prepared as described above.

2.4 Sample Incubation

5 μL of the working solutions at 16 μM of the compound of Example 6 and the control example CC-92480 were each added to 75 μL of plasma to make the final concentration of the compounds of 1 μM. The samples were incubated under a 37° C. water bath for 0 min, 15 min, 30 min, 60 min, 90 min, 120 min, and 180 min. After the incubation, 240 μL of acetonitrile containing the internal standard was added, and the plate was shaken on a shaker at 800 rpm for 10 min and centrifuged on a centrifugation at 4° C. at 3700 rpm for 20 min. The supernatant was analyzed by LC-MS with a sample injection volume of 2 μL.

3. Results

The conversion of the compound of the present disclosure in monkey plasma is shown in Table 4 below.

TABLE 4

Stability data of the compound of the present disclosure in monkey plasma

| No. | $T_{1/2}$ (min)/monkey |
|---|---|
| Example 6 | 806 |
| CC-92480 | 199 |

Conclusion: the compound of the present disclosure has stability advantages in monkey plasma.

The invention claimed is:

1. A compound of general formula (IIG) or the tautomer, mesomer, racemate, enantiomer or diastereomer thereof or the mixture thereof, or the pharmaceutically acceptable salt thereof:

(IIG)

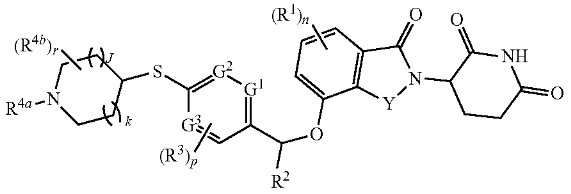

wherein:

Y is $CH_2$ or C(O);

$R^1$ are identical or different and are each independently selected from the group consisting of a hydrogen atom, halogen and $C_{1-6}$ alkyl;

n is 0, 1, 2 or 3;

$R^2$ is hydrogen atom;

$G^1$, $G^2$ and $G^3$ are identical or different and are each independently a carbon atom or a nitrogen atom;

$R^3$ are identical or different and are each independently selected from the group consisting of a hydrogen atom, halogen and $C_{1-6}$ alky;

p is 0, 1, 2, 3 or 4;

$R^4$ is

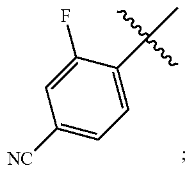 [SMILES: *c1ccc(C#N)cc1F]

;

$R^{4b}$ is a hydrogen atom;

r is 0, 1 or 2;

J is 0 or 1; and k is 0 or 1.

2. The compound of general formula (IIG) or the tautomer, mesomer, racemate, enantiomer or diastereomer thereof or the mixture thereof, or the pharmaceutically acceptable salt thereof according to claim 1, wherein $R^1$ is a hydrogen atom; and $R^3$ is a hydrogen atom.

3. The compound of general formula (IIG) or the tautomer, mesomer, racemate, enantiomer or diastereomer thereof or the mixture thereof, or the pharmaceutically acceptable salt thereof according to claim 1, selected from the group consisting of the following compounds:

1

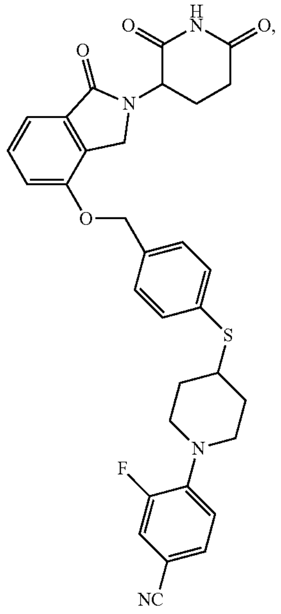

,

2
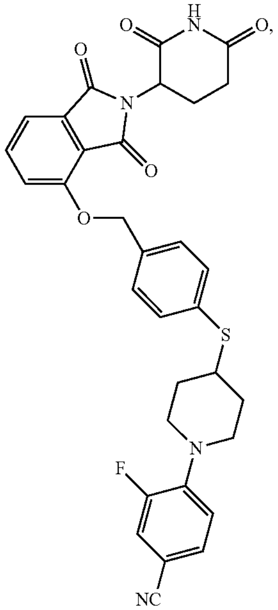
2-2
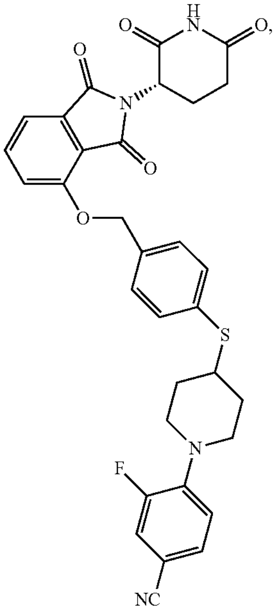
2-1
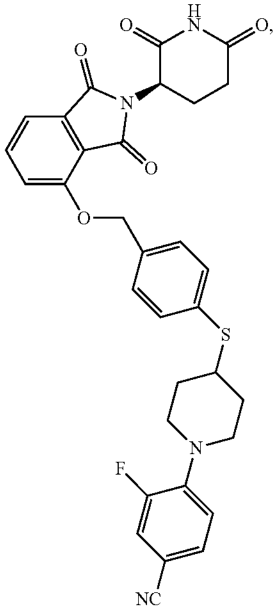
3
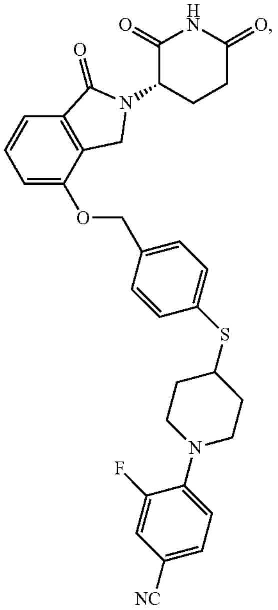

-continued
3′
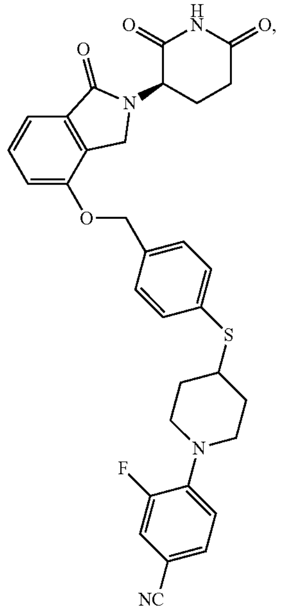
4
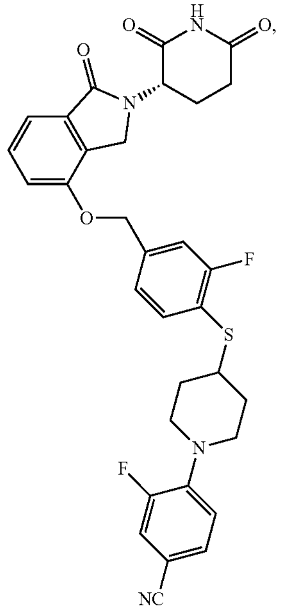
-continued
4′
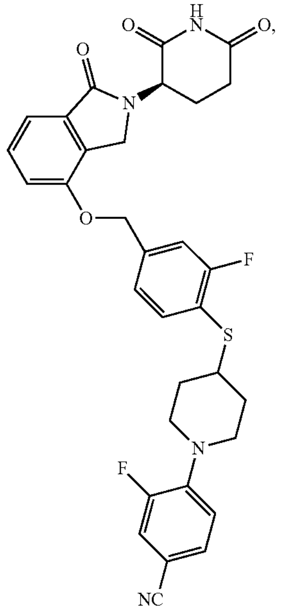
4′a
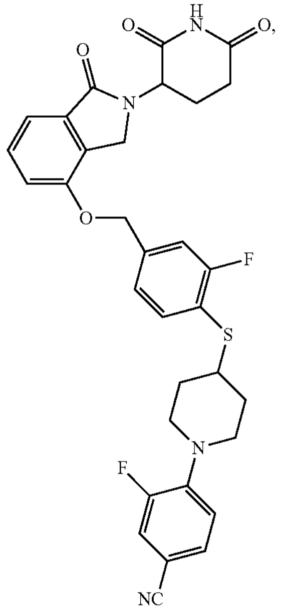

-continued
5
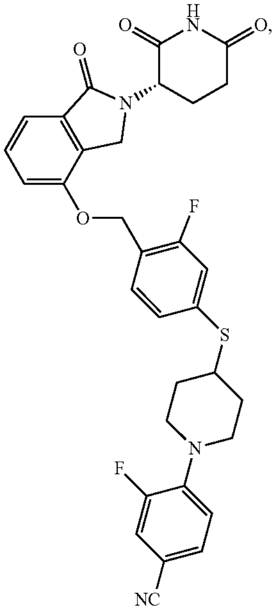
5′a
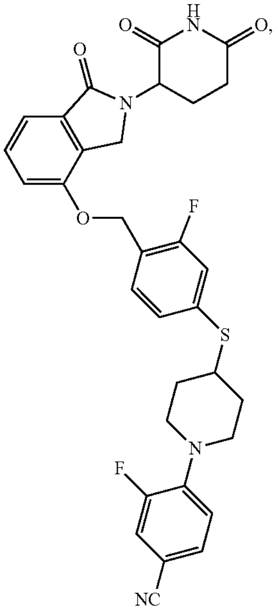
5′
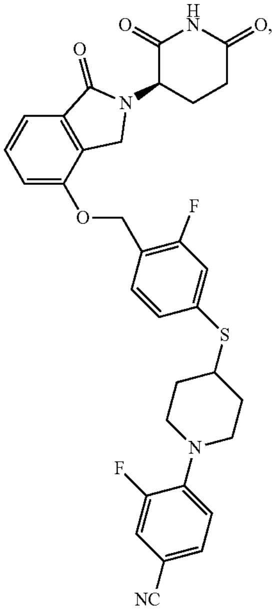
6
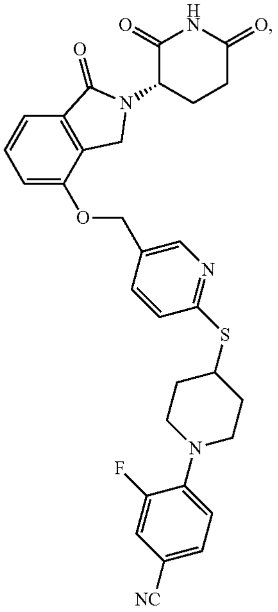

-continued
6′
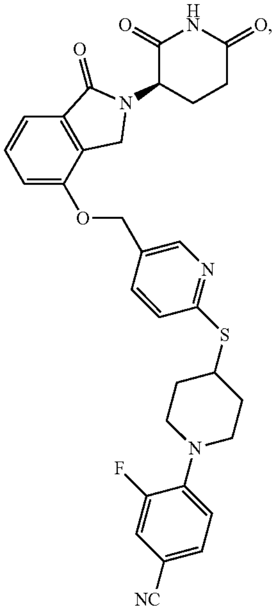
6′a
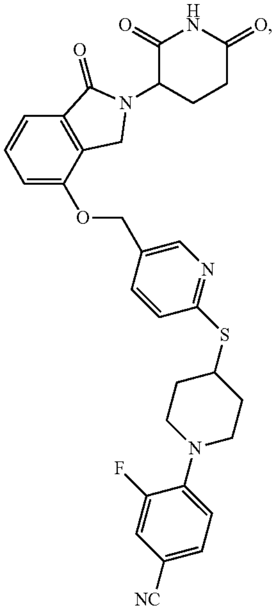
-continued
7
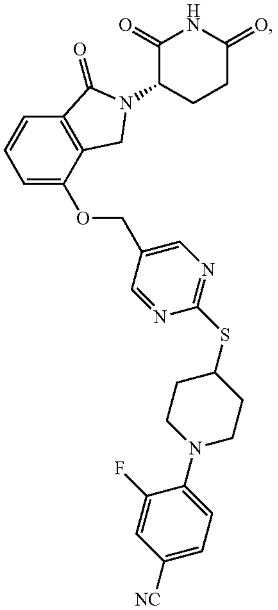
7′
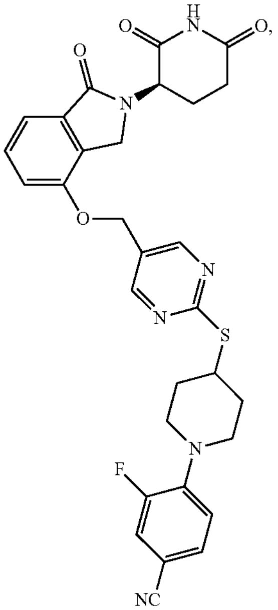

-continued
7'a
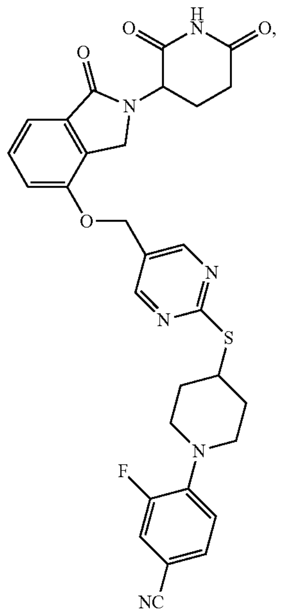
8'
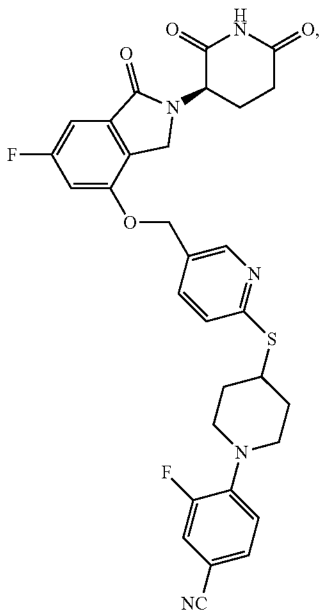
8
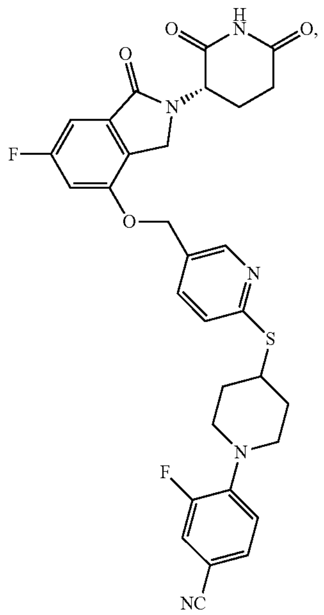
8'a
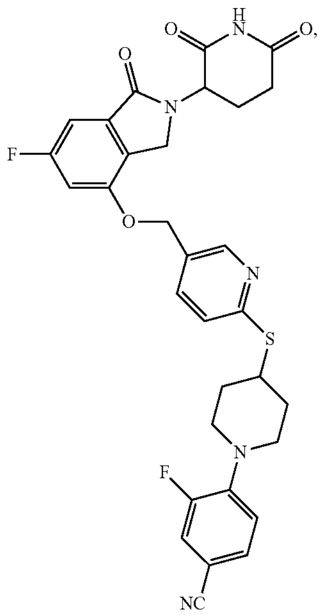

-continued
9
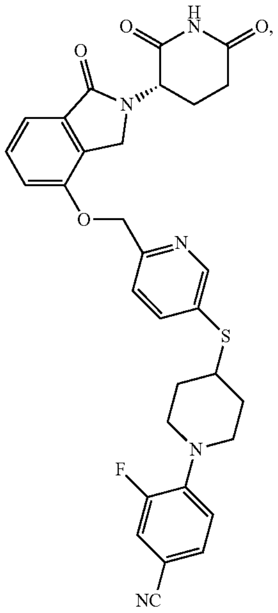
9′
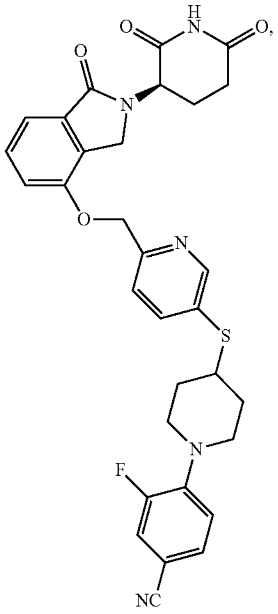
-continued
9′a
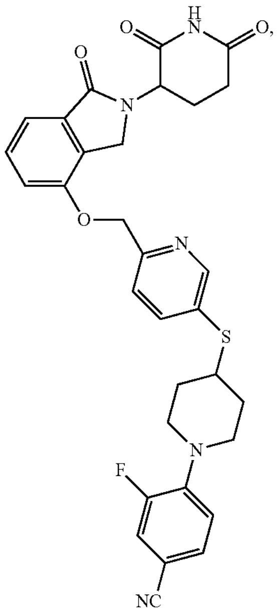
10
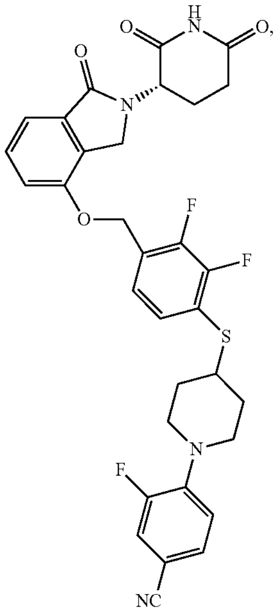

-continued
10′
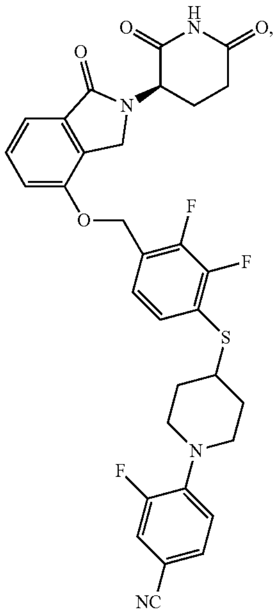
11
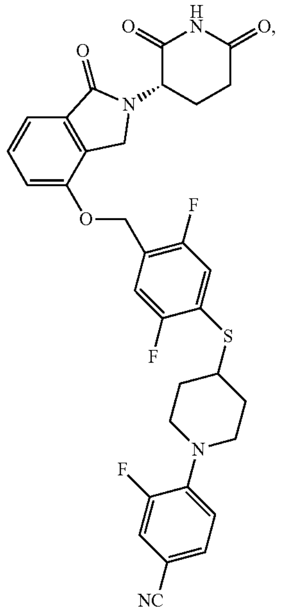
10′a
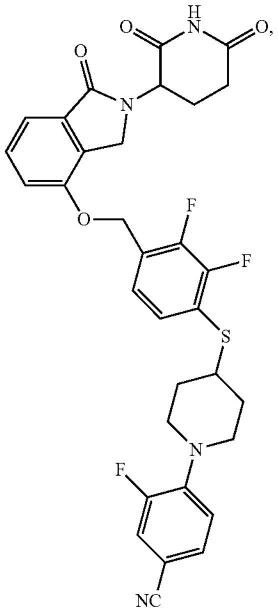
11′
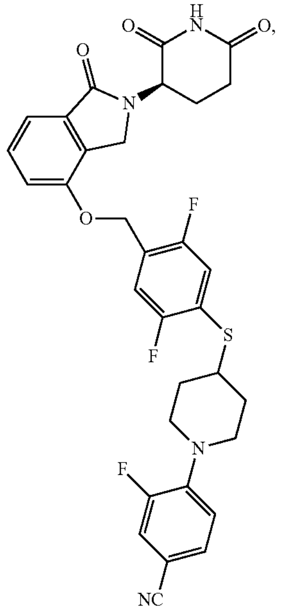

-continued
11′a
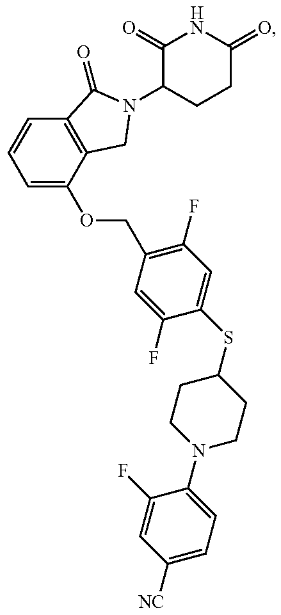
12′
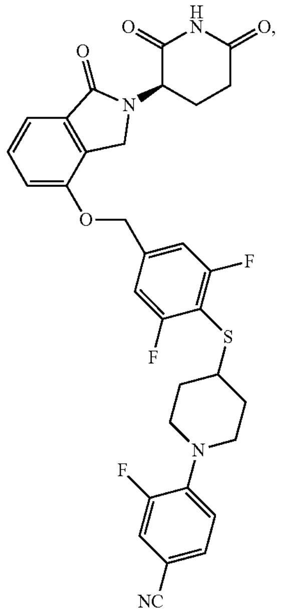
12
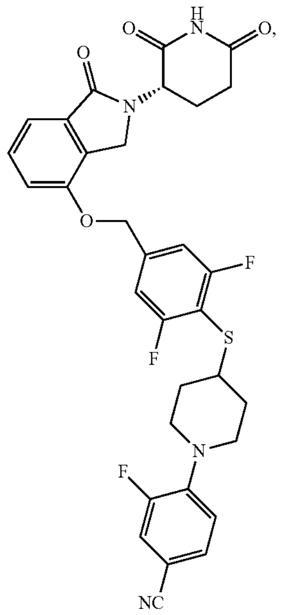
12′a
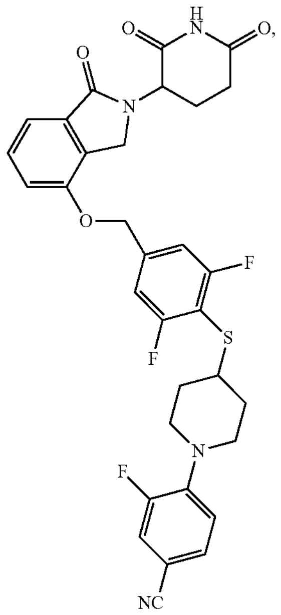

-continued
13
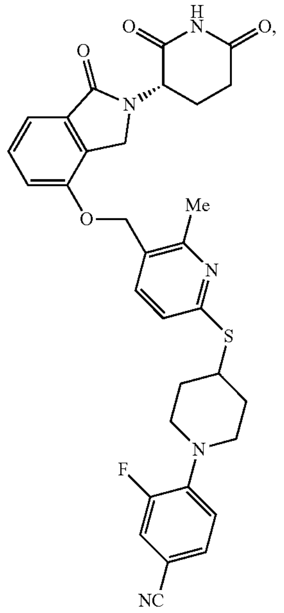
13′
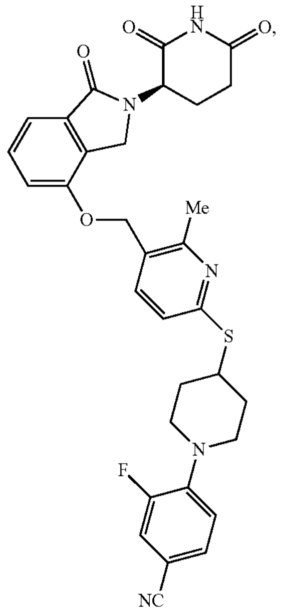
-continued
13′a
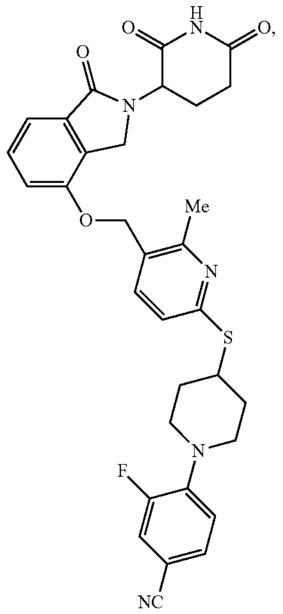
14
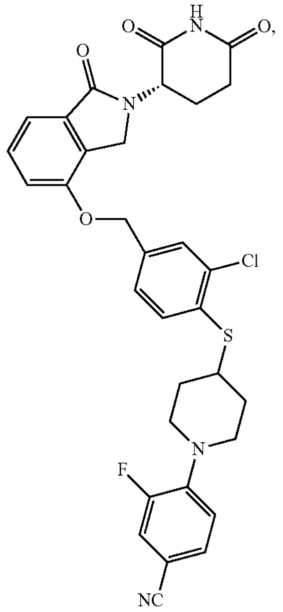

-continued
14′
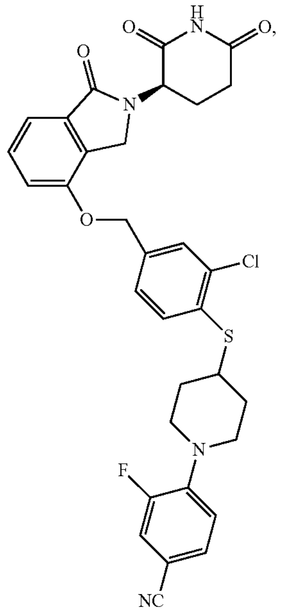
14′a
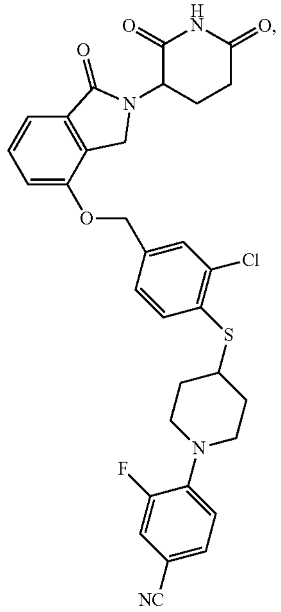
-continued
15
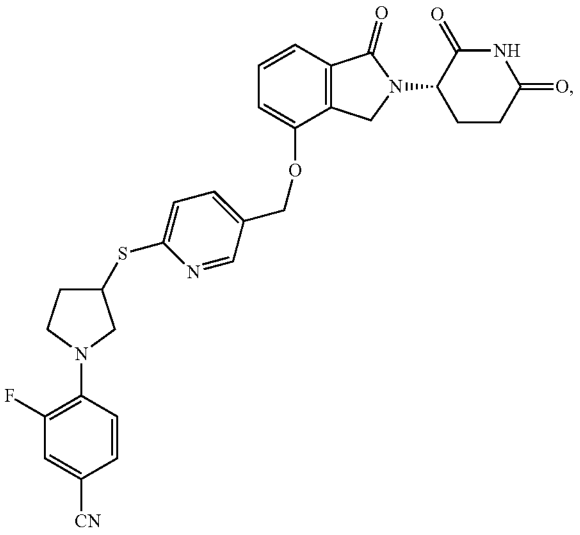
15′
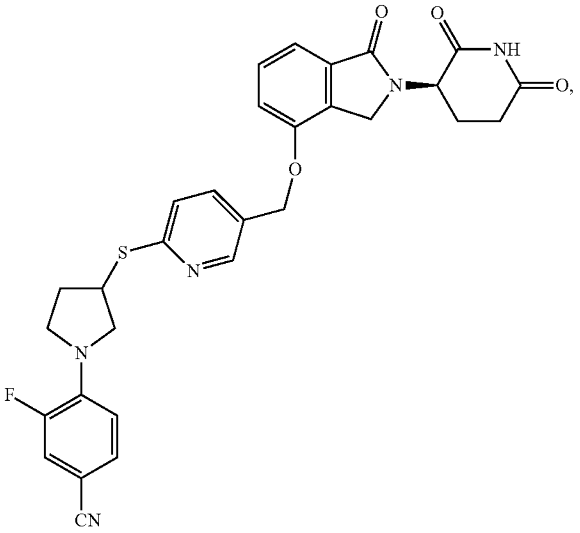
15′a
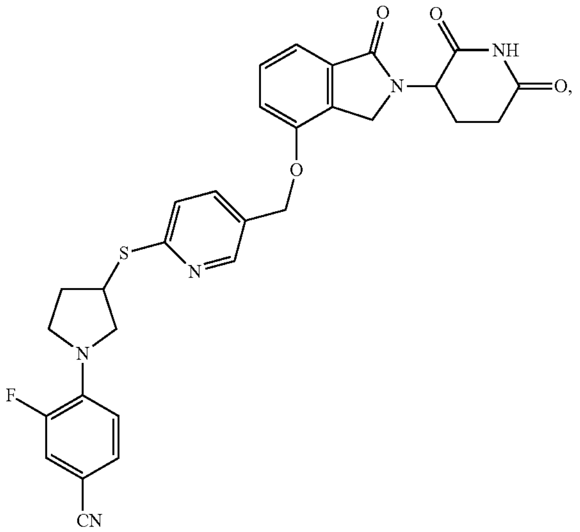

-continued
16
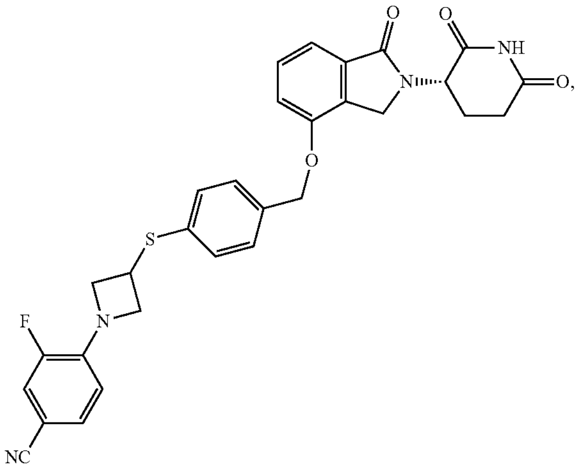
16′
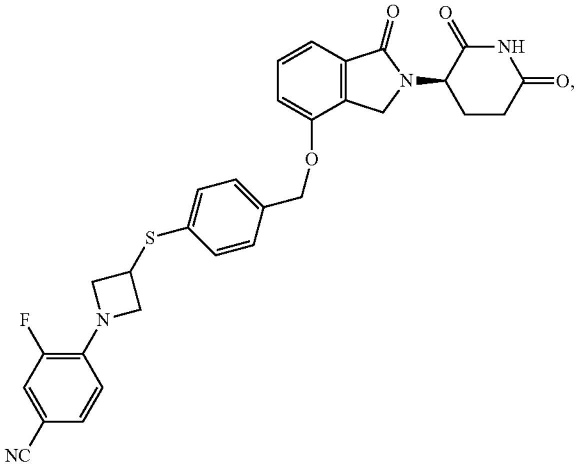
16′a
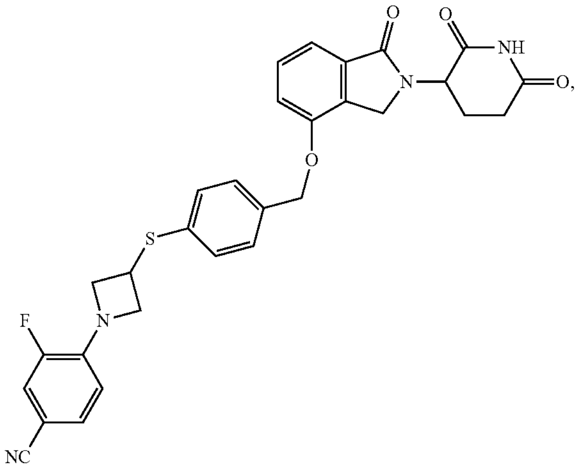
-continued
17
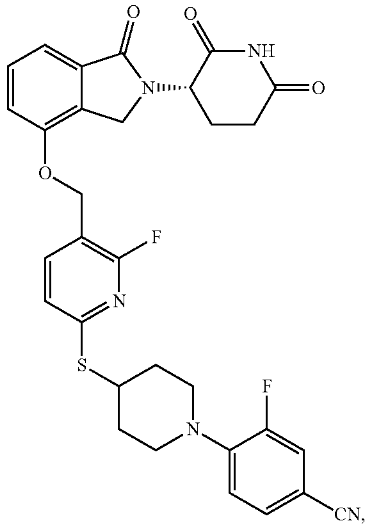
17′
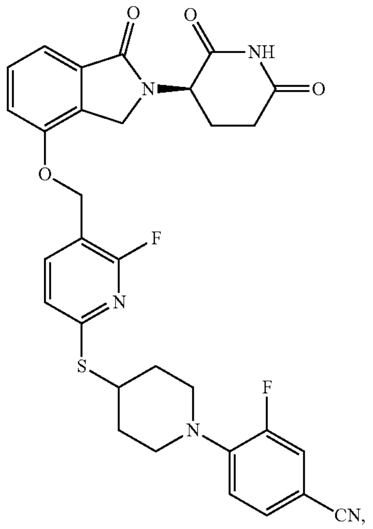
17′a
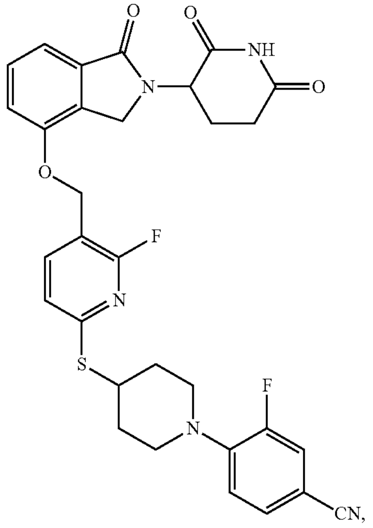

-continued
18
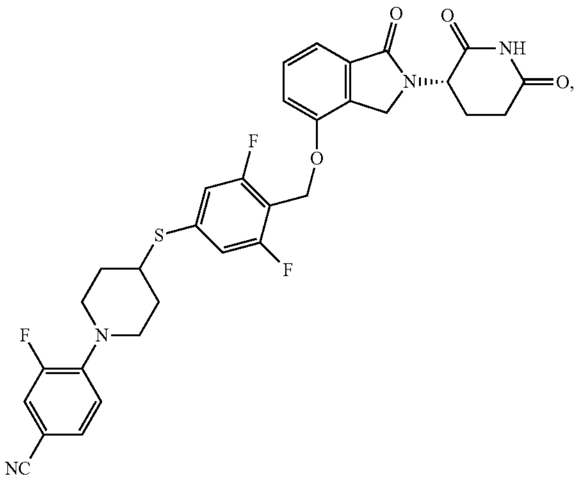
18'
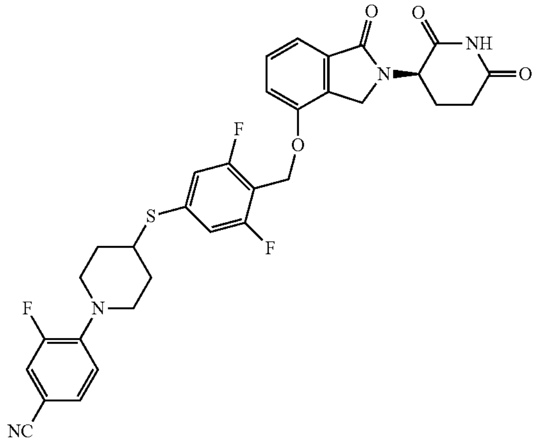
and
-continued
18'a
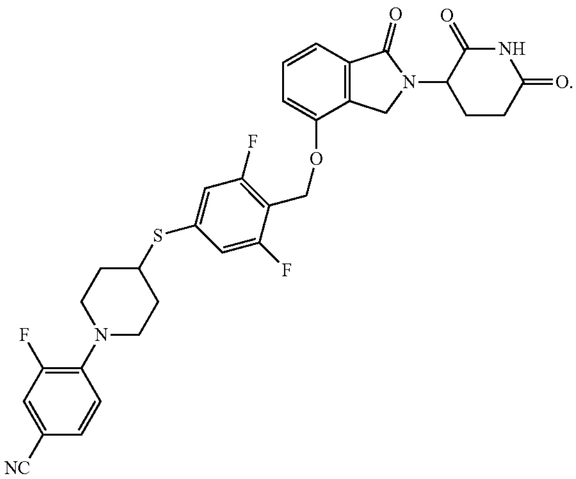
4. A pharmaceutical composition, comprising the compound of general formula (IIG) or the tautomer, mesomer, racemate, enantiomer or diastereomer thereof or the mixture thereof, or the pharmaceutically acceptable salt thereof according to claim 1, and one or more pharmaceutically acceptable carriers, diluents or excipients.
* * * * *